(12) United States Patent
Irvine et al.

(10) Patent No.: US 9,149,432 B2
(45) Date of Patent: *Oct. 6, 2015

(54) LIPID VESICLE COMPOSITIONS AND METHODS OF USE

(75) Inventors: Darrell J. Irvine, Arlington, MA (US); Jaehyun Moon, Ann Arbor, MI (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/400,076

(22) Filed: Feb. 19, 2012

(65) Prior Publication Data

US 2012/0177724 A1    Jul. 12, 2012

Related U.S. Application Data

(63) Continuation-in-part of application No. 13/052,067, filed on Mar. 19, 2011, now Pat. No. 8,747,869.

(60) Provisional application No. 61/315,485, filed on Mar. 19, 2010, provisional application No. 61/319,709, filed on Mar. 31, 2010.

(51) Int. Cl.

| A61K 9/127 | (2006.01) |
|---|---|
| A61K 47/44 | (2006.01) |
| A61P 33/06 | (2006.01) |
| C12N 5/071 | (2010.01) |
| A61K 39/015 | (2006.01) |
| A61K 39/21 | (2006.01) |
| A61K 39/39 | (2006.01) |
| A61K 47/48 | (2006.01) |
| C07K 14/005 | (2006.01) |
| C12N 15/88 | (2006.01) |
| A61K 39/00 | (2006.01) |

(52) U.S. Cl.
CPC .............. *A61K 9/1273* (2013.01); *A61K 39/015* (2013.01); *A61K 39/21* (2013.01); *A61K 39/39* (2013.01); *A61K 47/48815* (2013.01); *C07K 14/005* (2013.01); *C12N 15/88* (2013.01); *A61K 39/00* (2013.01); *A61K 2039/55511* (2013.01); *A61K 2039/55555* (2013.01); *A61K 2039/55572* (2013.01); *A61K 2039/575* (2013.01); *C12N 2740/15034* (2013.01)

(58) Field of Classification Search
CPC .......... A61K 2039/55555; A61K 2039/55572; A61K 47/48815; A61K 9/1273
USPC .................. 424/400, 191.1, 450; 554/154
See application file for complete search history.

(56) References Cited

U.S. PATENT DOCUMENTS

| 5,460,831 | A | 10/1995 | Kossovsky et al. |
|---|---|---|---|
| 5,464,629 | A | 11/1995 | Monshipouri et al. |
| 5,532,133 | A * | 7/1996 | Barnwell ............. 435/7.22 |
| 5,534,259 | A | 7/1996 | Zalipsky et al. |
| 5,753,261 | A | 5/1998 | Fernandez et al. |
| 6,120,751 | A * | 9/2000 | Unger ................... 424/9.51 |
| 6,143,305 | A * | 11/2000 | Stevens ................ 424/195.11 |
| 6,194,388 | B1 | 2/2001 | Krieg et al. |
| 6,544,549 | B1 | 4/2003 | Boni et al. |
| 6,589,940 | B1 | 7/2003 | Raz et al. |
| 6,693,086 | B1 | 2/2004 | Dow et al. |
| 7,790,186 | B2 | 9/2010 | Yadava et al. |
| 2002/0040203 | A1 | 4/2002 | Sen et al. |
| 2003/0054027 | A1 | 3/2003 | Unger |
| 2003/0235619 | A1 | 12/2003 | Allen et al. |
| 2004/0247624 | A1 | 12/2004 | Unger et al. |
| 2005/0042298 | A1 | 2/2005 | Pardridge et al. |
| 2005/0266067 | A1 | 12/2005 | Sengupta et al. |
| 2006/0275371 | A1 | 12/2006 | Dai et al. |
| 2007/0059318 | A1 | 3/2007 | Balu-Iyer et al. |
| 2007/0298093 | A1 | 12/2007 | Konur et al. |
| 2008/0014144 | A1 | 1/2008 | Saltzman et al. |
| 2008/0267986 | A1 | 10/2008 | Pfeifer et al. |
| 2008/0317787 | A1 * | 12/2008 | Cohen .................. 424/272.1 |
| 2009/0196883 | A1 | 8/2009 | Yadava et al. |
| 2010/0226973 | A1 | 9/2010 | Fujii et al. |
| 2010/0323018 | A1 | 12/2010 | Irvine et al. |
| 2010/0324124 | A1 | 12/2010 | Irvine et al. |
| 2011/0177156 | A1 | 7/2011 | Szoka et al. |
| 2011/0229529 | A1* | 9/2011 | Irvine et al. ............. 424/400 |
| 2011/0229556 | A1 | 9/2011 | Irvine et al. |
| 2011/0293705 | A1 | 12/2011 | Irvine et al. |
| 2012/0003295 | A1 | 1/2012 | Jiang et al. |
| 2012/0121688 | A1 | 5/2012 | Ishii et al. |

FOREIGN PATENT DOCUMENTS

| CA | 2600220 | 3/2008 |
|---|---|---|
| EP | 0 160 266 | 11/1985 |

(Continued)

OTHER PUBLICATIONS

Li et al. (Nature Structural & Molecular Biology; vol. 14, No. 10, Oct. 2007).*
Acharya et al., Synthetic vaccines: Immunity without harm. Nat Mater. Mar. 2011;10(3):166-8.
Ancsin et al., A binding site for highly sulfated heparan sulfate is identified in the N. terminus of the circumsporozoite protein: significance for malarial sporozoite attachment to hepatocytes. J Biol Chem. May 21, 2004;279(21):21824-32. Epub Mar. 7, 2004.
Bell et al., Process development for the production of an *E. coli* produced clinical grade recombinant malaria vaccine for Plasmodium vivax. Vaccine. Feb. 25, 2009;27(9):1448-53. Epub Jan. 10, 2009.
Bershteyn et al., Polymer-supported lipid shells, onions, and flowers. Soft Matter. 2008;4(9):1787-1791.
Bershteyn et al., Robust IgG responses to nanograms of antigen using a biomimetic lipid-coated particle vaccine. J Control Release. Feb. 10, 2012;157(3):354-65. Epub Jul. 24, 2011.

(Continued)

*Primary Examiner* — Anna Falkowitz
(74) *Attorney, Agent, or Firm* — Wolf, Greenfield & Sacks, P.C.

(57) ABSTRACT

The invention provides delivery systems comprised of stabilized multilamellar vesicles, as well as compositions, methods of synthesis, and methods of use thereof. The stabilized multilamellar vesicles comprise terminal-cysteine-bearing antigens or cysteine-modified antigens, at their surface and/or internally.

16 Claims, 26 Drawing Sheets

(56) References Cited

FOREIGN PATENT DOCUMENTS

| | | |
|---|---|---|
| JP | 2002-500165 | 1/2002 |
| WO | WO 00/28972 | 5/2000 |
| WO | WO 00/64413 | 11/2000 |
| WO | WO 03/075977 | 9/2003 |
| WO | WO 2006/119121 A2 | 11/2006 |

OTHER PUBLICATIONS

Bilsborough et al., Fine epitope specificity of antibodies to region II of the Plasmodium vivax circumsporozoite protein correlates with ability to bind recombinant protein and sporozoites. Acta Trop. May 15, 1997;65(2):59-80. Abstract only.

Düzgüneş et al., Calcium- and magnesium-induced fusion of mixed phosphatidylserine/phosphatidylcholine vesicles: effect of ion binding. J Membr Biol. Apr. 15, 1981;59(2):115-25.

Genbank Submission; Accession No. AAB59956.1; Woo et al.; Mar. 29, 2007. 1 page.

Genbank Submission; Accession No. AJ278611.1; Lim et al.; Nov. 14, 2006. 2 pages.

Krishnamachari et al., Innovative strategies for co-delivering antigens and CpG oligonucleotides. Adv Drug Deliv Rev. Mar. 28, 2009;61(3):205-17. Epub Jan. 19, 2009.

Lachman et al., Cytokine-containing liposomes as vaccine adjuvants. Eur Cytokine Netw. Dec. 1996;7(4):693-8.

Lavelle et al., The stability and immunogenicity of a protein antigen encapsulated in biodegradable microparticles based on blends of lactide polymers and polyethylene glycol. Vaccine. Feb. 12, 1999;17(6):512-29.

Martínez Gómez et al., A protective allergy vaccine based on CpG- and protamine-containing PLGA microparticles. Pharm Res. Oct. 2007;24(10):1927-35. Epub May 31, 2007.

Moon et al., Enhancing humoral responses to a malaria antigen with nanoparticle vaccines that expand Tfh cells and promote germinal center induction. Proc Natl Acad Sci U S A. Jan. 24, 2012;109(4):1080-5. Epub Jan. 12, 2012.

Moon et al., Interbilayer-crosslinked multilamellar vesicles as synthetic vaccines for potent humoral and cellular immune responses. Nat Mater. Mar. 2011;10(3):243-51. Epub Feb. 20, 2011.

O'Hagan et al., Microparticles as potentially orally active immunological adjuvants. Vaccine. Oct. 1989;7(5):421-4.

O'Hagan et al., Microparticles as vaccine adjuvants and delivery systems. Expert Rev Vaccines. Apr. 2003;2(2):269-83.

Singh et al., Anionic microparticles are a potent delivery system for recombinant antigens from Neisseria meningitidis serotype B. J Pharm Sci. Feb. 2004;93(2):273-82.

Singh et al., Charged polylactide co-glycolide microparticles as antigen delivery systems. Expert Opin Biol Ther. Apr. 2004;4(4):483-91.

Singh et al., Nanoparticles and microparticles as vaccine-delivery systems. Expert Rev Vaccines. Oct. 2007;6(5):797-808.

Singh et al., Polylactide-co-glycolide microparticles with surface adsorbed antigens as vaccine delivery systems. Curr Drug Deliv. Jan. 2006;3(1):115-20.

Verma et al., Surface-structure-regulated cell-membrane penetration by monolayer-protected nanoparticles. Nat Mater. Jul. 2008;7(7):588-95. Epub May 25, 2008.

Yadava et al., A novel chimeric Plasmodium vivax circumsporozoite protein induces biologically functional antibodies that recognize both VK210 and VK247sporozoites. Infect Immun. Mar. 2007;75(3):1177-85. Epub Dec. 11, 2006.

Zhang et al., Potent antigen-specific immune responses stimulated by codelivery of CpG ODN and antigens in degradable microparticles. J Immunother. Jul.-Aug. 2007;30(5):469-78.

Agrawal et al., Cutting edge: different Toll-like receptor agonists instruct dendritic cells to induce distinct Th responses via differential modulation of extracellular signal-regulated kinase-mitogen-activated protein kinase and c-Fos. J Immunol. Nov. 15, 2003;171(10):4984-9.

Allen et al., Anti-CD19-targeted liposomal doxorubicin improves the therapeutic efficacy in murine B-cell lymphoma and ameliorates the toxicity of liposomes with varying drug release rates. Clin Cancer Res. May 1, 2005;11(9):3567-73.

Allen et al., Drug delivery systems: entering the mainstream. Science. Mar. 19, 2004;303(5665):1818-22.

Alving, Lipopolysaccharide, lipid A, and liposomes containing lipid A as immunologic adjuvants. Immunobiology. Apr. 1993;187(3-5):430-46.

Alving, Liposomes as carriers of antigens and adjuvants. J Immunol Methods. Jun. 24, 1991;140(1):1-13.

Bhowmick et al., Comparison of liposome based antigen delivery systems for protection against Leishmania donovani. J Controlled Release. Jan. 25, 2010;141(2):199-207. Epub Oct. 7, 2009.

Cashion et al., Biomimetic design and performance of polymerizable lipids. Acc Chem Res. Aug. 18, 2009;42(8):1016-25. Epub May 19, 2009. doi: 10.1021/ar800191s.

Collins et al., Processing of exogenous liposome-encapsulated antigens in vivo generates class I MHC-restricted T cell responses. J Immunol. Jun. 1, 1992;148(11):3336-41.

Davis et al., Liposomes as adjuvants with immunopurified tetanus toxoid: influence of liposomal characteristics. Immunology. Jun. 1987;61(2):229-34.

Davis et al., Liposomes as adjuvants with immunopurified tetanus toxoid: the immune response. Immunol Lett. Apr. 1987;14(4):341-8.

Davis et al., Nanoparticle therapeutics: an emerging treatment modality for cancer. Nat Rev Drug Discov. Sep. 2008;7(9):771-82. Doi: 10.1038/nrd2614. Abstract only.

Demento et al, Inflammasome-activating nanoparticles as modular systems for optimizing vaccine efficacy. Vaccine. May 18, 2009;27(23):3013-21. doi: 10.1016/j.vaccine.2009.03.034. Epub Apr. 3, 2009. Author manuscript available in PMC May 18, 2010 is provided.

Diwan et al., Dose sparing of CpG oligodeoxynucleotide vaccine adjuvants by nanoparticle delivery. Curr Drug Deliv. Oct. 2004;1(4):405-12. Abstract only.

Drummond et al., Optimizing liposomes for delivery of chemotherapeutic agents to solid tumors. Pharmacol Rev. Dec. 1999;51(4):691-743.

Fifis et al., Size-dependent immunogenicity: therapeutic and protective properties of nano-vaccines against tumors. J Immunol. Sep. 1, 2004;173(5):3148-54.

Fischer et al., Nanotoxicity: the growing need for in vivo study. Curr Opin Biotechnol. Dec. 2007;18(6):565-71. Epub Dec. 21, 2007.

Friede et al., Induction of immune response against a short synthetic peptide antigen coupled to small neutral liposomes containing monophosphoryl lipid A. Mol Immunol. Apr. 1993;30(6):539-47.

Gabizon et al., Prolonged circulation time and enhanced accumulation in malignant exudates of doxorubicin encapsulated in polyethylene-glycol coated liposomes. Cancer Res. Feb. 15, 1994;54(4):987-92.

Glenn et al., Murine IgG subclass antibodies to antigens incorporated in liposomes containing lipid A. Immunol Lett. Jul.-Aug. 1995;47(1-2):73-8. Abstract only.

Gregoriadis et al., Liposomes as immunological adjuvants and vaccine carriers. J Control Release. Aug. 1996;41(1-2):49-56.

Halter et al., Engineered lipids that cross-link the inner and outer leaflets of lipid bilayers. Langmuir. Mar. 16, 2004;20(6):2416-23. Epub Feb. 14, 2004.

Hamdy et al., Enhanced antigen-specific primary CD4+ and CD8+ responses by codelivery of ovalbumin and toll-like receptor ligand monophosphoryl lipid A in poly(D,L-lactic-co-glycolic acid) nanoparticles. J Biomed Mater Res A. Jun. 1, 2007;81(3):652-62. Epub Dec. 22, 2006.

Heffernan et al., The stimulation of CD8+ T cells by dendritic cells pulsed with polyketal microparticles containing ion-paired protein antigen and poly(inosinic acid)-poly(cytidylic acid). Biomaterials. Feb. 2009;30(5):910-8. doi: 10.1016/j.biomaterials.2008.10.034. Epub Nov. 25, 2008.

Heit et al., Antigen co-encapsulated with adjuvants efficiently drive protective T cell immunity. Eur J Immunol. Aug. 2007;37(8):2063-74.

(56) References Cited

OTHER PUBLICATIONS

Hori et al., Injectable dendritic cell-carrying alginate gels for immunization and immunotherapy. Biomaterials. Sep. 2008;29(27):3671-82. doi: 10.1016/j.biomaterials.2008.05.033. Epub Jun. 20, 2008.

Hotz et al., Vesicle-templated polymer hollow spheres. Langmuir. Mar. 1998;14(5):1031-6. Epub Feb. 3, 1998.

Hu et al., Cytosolic delivery of membrane-impermeable molecules in dendritic cells using pH-responsive core-shell nanoparticles. Nano Lett. Oct. 2007;7(10):3056-64. Epub Sep. 21, 2007. Abstract only.

Iden et al., In vitro and in vivo comparison of immunoliposomes made by conventional coupling techniques with those made by a new post-insertion approach. Biochim Biophys Acta. Aug. 6, 2001;1513(2):207-16.

Irvine, Engineering nanomaterials as vaccine adjuvants and agents for cancer immunotherapy. Seminar at Scripps Res Institute Apr. 28, 2011. 57 slides.

Ishida et al., A combinatorial approach to producing sterically stabilized (Stealth) immunoliposomal drugs. FEBS Lett. Oct. 22, 1999;460(1):129-33.

Jeong et al., Enhanced adjuvantic property of polymerized liposome as compared to a phospholipid liposome. J Biotechnol. Apr. 11, 2002; 94(3):255-263.

Kipper et al., Single dose vaccine based on biodegradable polyanhydride microspheres can modulate immune response mechanism. J Biomed Mater Res A. Mar. 15, 2006;76(4):798-810. Epub Dec. 12, 2005.

Kirby et al., Dehydration-rehydration vesicles: a simple method for high yield drug entrapment in liposomes. Nat Biotechnol. Nov. 1984;2(11):979-84.

Kwon et al., In vivo targeting of dendritic cells for activation of cellular immunity using vaccine carriers based on pH-responsive microparticles. Proc Natl Acad Sci U S A. Dec. 20, 2005;102(51):18264-8. Epub Dec. 12, 2005.

Li et al., Energetics and dynamics of SNAREpin folding across lipid bilayers. Nat Structural Molec Biol. Oct. 2007;14(10):890-6. Epub Sep. 30, 2007.

Lutsiak et al., Analysis of poly(D,L-lactic-co-glycolic acid) nanosphere uptake by human dendritic cells and macrophages in vitro. Pharm Res. Oct. 2002;19(10):1480-7.

Mata-Haro et al., The vaccine adjuvant monophosphoryl lipid A as a TRIF-biased agonist of TLR4. Science. Jun. 15, 2007;316(5831):1628-32. With Erratum.

McKee et al., How do adjuvants work? Important considerations for new generation adjuvants. Immunity. Nov. 2007;27(5):687-90.

Moghimi et al., Long-circulating and target-specific nanoparticles: theory to practice. Pharmacol Rev. Jun. 2001;53(2):283-318.

Mohammed et al., Lyophilisation and sterilisation of liposomal vaccines to produce stable and sterile products. Methods. Sep. 2006;40(1):30-8.

Moon et al., Engineering nano- and microparticles to tune immunity. Adv Mater. Jul. 24, 2012;24(28):3724-46. doi: 10.1002/adma.201200446. Epub May 29, 2012. Abstract only.

Mundargi et al., Nano/micro technologies for delivering macromolecular therapeutics using poly(D,L-lactide-co-glycolide) and its derivatives. J Control Release. Feb. 11, 2008;125(3):193-209. Epub Oct. 22, 2007.

Nixon et al., Synthetic peptides entrapped in microparticles can elicit cytotoxic T cell activity. Vaccine. Nov. 1996;14(16):1523-30.

O'Hagan et al., Induction of potent immune responses by cationic microparticles with adsorbed human immunodeficiency virus DNA vaccines. J Virol. Oct. 2001;75(19):9037-43.

Owens et al., Opsonization, biodistribution, and pharmacokinetics of polymeric nanoparticles. Int J Pharm. Jan. 3, 2006;307(1):93-102. Epub Nov. 21, 2005. Abstract only.

Papahadjopoulos et al., Molecular mechanisms of calcium-induced membrane fusion. J Bioenerg Biomembr. Apr. 1990;22(2):157-79.

Popescu et al., A novel proteoliposomal vaccine elicits potent antitumor immunity in mice. Blood. Jun. 15, 2007;109(12):5407-10. Epub Mar. 9, 2007.

Reddy et al., Exploiting lymphatic transport and complement activation in nanoparticle vaccines. Nature Biotechnology. Oct. 2007;25(10):1159-64. Epub Sep. 16, 2007.

Reddy et al., In vivo cytotoxic T lymphocyte induction with soluble proteins administered in liposomes. J Immunol. Mar. 1, 1992;148(5):1585-9.

Reed et al., New horizons in adjuvants for vaccine development. Trends Immunol. Jan. 2009;30(1):23-32. doi:10.1016/j.it.2008.09.006. Epub Dec. 6, 2008.

Ross et al., Planar supported lipid bilayer polymers formed by vesicle fusion. 1. Influence of diene monomer structure and polymerization method on film properties†. Langmuir. Mar. 2003;19(5):1752-65. Epub Jan. 11, 2003.

Schlosser et al., TLR ligands and antigen need to be coencapsulated into the same biodegradable microsphere for the generation of potent cytotoxic T lymphocyte responses. Vaccine. Mar. 20, 2008;26(13):1626-37. doi: 10.1016/j.vaccine.2008.01.030. Epub Feb. 6, 2008.

Singh et al., Cationic microparticles are an effective delivery system for immune stimulatory cpG DNA. Pharm Res. Oct. 2001;18(10):1476-9.

Singh et al., Cationic microparticles: A potent delivery system for DNA vaccines. Proc Natl Acad Sci U S A. Jan. 18, 2000;97(2):811-6.

Singh et al., Recent advances in vaccine adjuvants. Pharm Res. Jun. 2002;19(6):715-28.

Steers et al., Liposome-encapsulated HIV-1 Gag p24 containing lipid A induces effector CD4+ T-cells, memory CD8+ T-cells, and pro-inflammatory cytokines. Vaccine. Nov. 16, 2009;27(49):6939-49. Epub Sep. 11, 2009.

Takasaki et al., Micelles as intermediates in the preparation of protein-liposome conjugates. Bioconjug Chem. Mar.-Apr. 2006;17(2):438-50. Epub Jan. 12, 2006.

Tamauchi et al., Enhancement of immunogenicity by incorporation of lipid A into liposomal model membranes and its application to membrane-associated antigens. Immunology. Dec. 1983;50(4):605-12.

Torchilin, Recent advances with liposomes as pharmaceutical carriers. Nat Rev Drug Disc. Feb. 2005;4(2):145-60.

Vangala et al., Comparison of vesicle based antigen delivery systems for delivery of hepatitis B surface antigen. J Controlled Release. May 14, 2007;119(1):102-10. Epub Jan. 27, 2007.

Vasir et al., Biodegradable nanoparticles for cytosolic delivery of therapeutics. Adv Drug Deliv Rev. Aug. 10, 2007;59(8):718-28. Epub Jun. 26, 2007. Author manuscript available in PMC Aug. 10, 2008 is provided.

Vonarbourg et al., Parameters influencing the stealthiness of colloidal drug delivery systems. Biomaterials. Aug. 2006;27(24):4356-73. Epub May 2, 2006. Abstract only.

Wakita et al., An indispensable role of type-1 IFNs for inducing CTL-mediated complete eradication of established tumor tissue by CpG-liposome co-encapsulated with model tumor antigen. Int Immunol. Mar. 2006;18(3):425-34. Advance access publication Jan. 13, 2006.

Walker et al., Toward an AIDS vaccine. Science. May 9, 2008;320(5877):760-4. doi: 10.1126/science.1152622.

Wilson-Welder et al., Vaccine adjuvants: current challenges and future approaches. J Pharm Sci. Apr. 2009;98(4):1278-316. doi: 10.1002/jps.21523.

Yoshina-Ishii et al., General method for modification of liposomes for encoded assembly on supported bilayers. J Am Chem Soc. Feb. 9, 2005;127(5):1356-7. Epub Jan. 12, 2005.

Yue et al., Enhanced resistance to coxsackievirus B3-induced myocarditis by intranasal co-immunization of lymphotactin gene encapsulated in chitosan particle. Virology. Apr. 10, 2009;386(2):438-47. doi:10.1016/j.virol.2009.01.029. Epub Feb. 23, 2009.

Zauner et al., In vitro uptake of polystyrene microspheres: effect of particle size, cell line and cell density. J Control Release. Mar. 12, 2001;71(1):39-51.

Zhu et al., Stabilization of proteins encapsulated in injectable poly (lactide-co-glycolide). Nat Biotechnol. Jan. 2000;18(1):52-7.

(56) References Cited

OTHER PUBLICATIONS

Akagi et al., [Development of vaccine adjuvants using polymeric nanoparticles and their potential applications for anti-HIV vaccine]. Yakugaku Zasshi. Feb. 2007;127(2):307-17.

Bershteyn et al. Lipid-coated nano-and microparticles for vaccine design. Materials Research Society fall meeting. 2009. 7 pages Bershteyn et al., Versatile lipid-based vaccine carriers elicit CTL and antibody responses to surface-conjugated or encapsulated antigen. Keystone Symposium. 2010. 1 page.

Berstheyn et al., Versatile lipid-bases vaccine carriers elicit CTL and antibody responses to surface-conjugated or encapsulated antigen. Keystone Symposium abstract. 2010. 1 page.

Haining et al., pH-triggered microparticles for peptide vaccination. J Immunol. Aug. 15, 2004;173(4):2578-85. Erratum in: J Immunol. Nov. 15, 2004;173(10):following 6489. von Berwelt Baildon, MS [corrected to von Bergwelt-Baildon, MS].

Irvine, Engineering naonparticle delivery for vaccines and immunotherapy. Nanotechnology in Infectious Disease meeting, Atlanta, GA. 2010. 33 pages.

Ratnayaka et al., Preparation and characterization of asymmetric planar supported bilayers composed of poly(bis-sorbylphosphatidylcholine) on n-octadecyltrichlorosilane SAMs. J Colloid Interface Sci. Nov. 1, 2008;327(1):63-74. Epub Aug. 9, 2008.

Singh et al., Immunogenicity and protection in small-animal models with controlled-release tetanus toxoid microparticles as a single-dose vaccine. Infect Immun. May 1997;65(5):1716-21.

\* cited by examiner

SEQUENCE LISTING

```
<160> NUMBER OF SEQ ID NOS: 8

<210> SEQ ID NO 1
<211> LENGTH: 257
<212> TYPE: PRT
<213> ORGANISM: Artificial Sequence
<220> FEATURE:
<223> OTHER INFORMATION: VMP Amino Acid Sequence

<400> SEQUENCE: 1

Thr His Cys Gly His Asn Val Asp Leu Ser Lys Ala Ile Asn Leu Asn
1               5                   10                  15

Gly Val Asn Phe Asn Asn Val Asp Ala Ser Ser Leu Gly Ala Ala His
            20                  25                  30

Val Gly Gln Ser Ala Ser Arg Gly Arg Gly Leu Gly Glu Asn Pro Asp
        35                  40                  45

Asp Glu Glu Gly Asp Ala Lys Lys Lys Asp Gly Lys Lys Ala Glu
    50                  55                  60
```

Pro Lys Asn Pro Arg Glu Asn Lys Leu Lys Gln Pro Gly Asp Arg Ala
65                  70                  75                  80

Asp Gly Gln Ala Ala Gly Asn Gly Ala Gly Gly Gln Pro Ala Gly Asp
                85                  90                  95

Arg Ala Ala Gly Gln Pro Ala Gly Asp Arg Ala Ala Gly Gln Pro Ala
            100                 105                 110

Gly Asp Gly Ala Ala Gly Gln Pro Ala Gly Asp Arg Ala Asp Gly Gln
        115                 120                 125

Pro Ala Gly Asp Arg Ala Asp Gly Gln Pro Ala Gly Asp Arg Ala Ala
    130                 135                 140

Gly Gln Ala Ala Gly Asn Gly Ala Gly Gly Gln Ala Ala Ala Asn Gly
145                 150                 155                 160

Ala Gly Asn Gln Pro Gly Gly Gly Asn Ala Ala Asn Lys Lys Ala Glu
                165                 170                 175

Asp Ala Gly Gly Asn Ala Gly Gly Asn Ala Gly Gln Gly Gln Asn
            180                 185                 190

Asn Glu Gly Ala Asn Ala Pro Asn Glu Lys Ser Val Lys Glu Tyr Leu
195                 200                 205

Asp Lys Val Arg Ala Thr Val Gly Thr Glu Trp Thr Pro Cys Ser Val
    210                 215                 220

Thr Cys Gly Val Gly Val Arg Val Arg Arg Val Asn Ala Ala Asn
225                 230                 235                 240

Lys Lys Pro Glu Asp Leu Thr Leu Asn Asp Leu Glu Thr Asp Val Cys
                245                 250                 255

Thr

<210> SEQ ID NO 2
<211> LENGTH: 771
<212> TYPE: DNA
<213> ORGANISM: Artificial Sequence
<220> FEATURE:
<223> OTHER INFORMATION: VMP Nucleotide Sequence

<400> SEQUENCE: 2
acacattgcg gacataatgt agatttatct aaagctataa atttaaatgg tgtaaacttc      60
aataacgtag acgctagttc actcggggct gcgcacgtag gtcagtctgc tagcagggg     120 cgcggtctcg gggaaaaccc agacgacgaa gaaggtgatg ctaaaaagaa aaaggacggt    180
aaaaaagcgg aaccaaaaaa tccaagggaa aataaattaa acagcccgg ggatcgcgcg     240 gatggtcaag cggcgggtaa tggggcgggg ggtcaaccag cggggatcg cgcggctggt    300 cagccagcgg gggatcgcgc ggctggtcag ccagcggggg atggtgcggc tggccaacca    360 gcggggatc gcgcggatgg tcagccagcg gggatcgcg cggatggtca accagccggt     420
gatcgcgcgg ctggccaagc ggccggtaat ggggcggggg gtcaagcggc gcgaacgga    480 gcggggaacc agccaggcgg cggtaacgct gcgaataaaa aagcggaaga tgcgggtggt    540
aacgcgggcg gtaatgcggg cggccaaggt cagaacaacg aaggggctaa tgcaccaaac    600
gaaaaatctg tcaaagaata tctcgataaa gtccgcgcta cagtagggac agaatggacg    660

```
ccatgctctg taacatgtgg tgtcggggta cgcgtgcgcc gccgtgtcaa tgcggctaac    720
aaaaaaccag aagatctcac gttaaatgat ctcgaaacgg atgtctgcac a             771
```

<210> SEQ ID NO 3
<211> LENGTH: 18
<212> TYPE: PRT
<213> ORGANISM: Artificial Sequence
<220> FEATURE:
<223> OTHER INFORMATION: VMP Type I repeat peptide fragment

<400> SEQUENCE: 3

Gly Asp Arg Ala Ala Gly Gln Pro Ala Gly Asp Arg Ala Asp Gly Gln
1               5                   10                  15

Pro Ala

<210> SEQ ID NO 4
<211> LENGTH: 20
<212> TYPE: PRT
<213> ORGANISM: Artificial Sequence
<220> FEATURE:
<223> OTHER INFORMATION: VMP AGDRx5 peptide fragment

<400> SEQUENCE: 4

Ala Gly Asp Arg Ala Gly Asp Arg Ala Gly Asp Arg Ala Gly Asp Arg
1               5                   10                  15

Ala Gly Asp Arg
            20

<210> SEQ ID NO 5
<211> LENGTH: 10
<212> TYPE: PRT
<213> ORGANISM: Artificial Sequence
<220> FEATURE:
<223> OTHER INFORMATION: VMP Region I peptide fragment

<400> SEQUENCE: 5

Asn Pro Arg Glu Asn Lys Leu Lys Gln Pro
1               5                   10

<210> SEQ ID NO 6
<211> LENGTH: 18
<212> TYPE: PRT
<213> ORGANISM: Artificial Sequence
<220> FEATURE:
<223> OTHER INFORMATION: VMP Region II peptide fragment

<400> SEQUENCE: 6

Glu Trp Thr Pro Cys Ser Val Thr Cys Gly Val Gly Val Arg Val Arg
1               5                   10                  15

Arg Arg

<210> SEQ ID NO 7
<211> LENGTH: 12
<212> TYPE: PRT
<213> ORGANISM: Artificial Sequence
<220> FEATURE:
<223> OTHER INFORMATION: VMP C-terminus peptide fragment

<400> SEQUENCE: 7

Pro Asn Glu Lys Ser Val Lys Glu Tyr Leu Asp Lys
1               5                   10

<210> SEQ ID NO 8
<211> LENGTH: 11

```
<212> TYPE: PRT
<213> ORGANISM: Artificial Sequence
<220> FEATURE:
<223> OTHER INFORMATION: scrambled control

<400> SEQUENCE: 8

Lys Pro Leu Asp Val Glu Lys Asn Ser Glu Tyr
1               5                   10
```

LIPID VESICLE COMPOSITIONS AND METHODS OF USE

RELATED APPLICATIONS

This application is a continuation-in-part of U.S. Non-Provisional application Ser. No. 13/052,067, filed on Mar. 19, 2011 and entitled LIPID VESICLE COMPOSITIONS AND METHODS OF USE, which claims the benefit under 35 U.S.C. §119(e) of U.S. Provisional Application Ser. No. 61/315,485, entitled "MICRO- AND NANOPARTICLES WITH SELF-ASSEMBLED LIPID COATINGS FOR SURFACE DISPLAY OF DRUGS SUCH AS VACCINE ANTIGENS AND ADJUVANTS" filed on Mar. 19, 2010, and U.S. Provisional Application Ser. No. 61/319,709, entitled "INTERBILAYER CROSSLINKED MULTILAMELLAR VESICLES" filed on Mar. 31, 2010, both of which are incorporated by reference herein in their entireties.

FEDERALLY SPONSORED RESEARCH

This invention was made with Government support under Grant No. CA140476 from the NIH, and Grant No. W911NF-07-D-0004 from the Department of Defense. The Government has certain rights in the invention.

BACKGROUND OF INVENTION

Liposomes have been widely used as a delivery vehicle for small molecules; however, it remains difficult to achieve high levels of encapsulation for many macromolecular drugs within liposomes and many drug formulations leak from liposomes too quickly to maintain useful drug delivery kinetics. While drug delivery by micro- and nanoparticles can encapsulate proteins and small-molecule drugs, this still typically yields very low total mass encapsulated drug per mass of particles, typically on the order of ~10 μg drug/mg particles. In addition, the organic solvents used in polymer particle synthesis and hydrophobic/acidic environment within these particles can lead to destruction of therapeutics. (See Zhu et al. Nat. Biotechnol. 2000 18:52-57.)

SUMMARY OF INVENTION

The invention generally provides novel and inventive drug delivery systems with higher loading capability, a capacity to sequester high levels of both hydrophobic and hydrophilic agents simultaneously, and longer release profiles. Some aspects of these delivery systems comprise stabilized multilamellar lipid vesicles having crosslinked lipid bilayers (referred to herein as interbilayer-crosslinked multilamellar vesicles or ICMV).

As shown in the Examples, the vesicles of the invention have unexpected enhanced encapsulation efficiency (e.g., in some instances, 100-fold more efficient than simple liposomes), and they are able to release encapsulated (or otherwise entrapped) agents via slow and sustained kinetics even in the presence of serum, making them highly desirable as sustained delivery vehicles in vivo. Moreover, as described in greater detail herein, the vesicles of the invention may be synthesized in aqueous environments, thereby avoiding the harsh conditions that are common in various prior art methods including the use of organic solvents and/or acidic environments. As a result, these synthesis methods are more suitable for a variety of agents including those that would typically be compromised structurally and/or functionally using such prior art methods. The resultant vesicles are therefore free of organic solvent and may be comprised solely of the lipids, including biodegradable lipids, and any agent encapsulated therein or therethrough.

The invention is based in part on these and other surprising and unexpected characteristics of the vesicles of the invention, as described in greater detail herein. Accordingly, the invention provides these stabilized vesicles, compositions comprising these vesicles, methods of making these vesicles, and methods of use thereof.

Thus, in one aspect, the invention provides a multilamellar lipid vesicle having crosslinks between lipid bilayers, or a plurality or population of multilamellar lipid vesicle having crosslinks between lipid bilayers. The plurality may be but is not limited to $1\text{-}10^3$, $1\text{-}10^4$, $1\text{-}10^5$, $1\text{-}10^6$, $1\text{-}10^7$, $1\text{-}10^8$, or $1\text{-}10^9$. Various aspects of the vesicles are described below and it is to be understood that these aspects apply equally to the plurality or population of vesicles, unless otherwise stated. It is to be understood that the vesicles of the invention comprise linkages between components of internal adjacent (or apposed) bilayers, and not simply crosslinks between components of the external (or outermost) bilayer or bilayer surface.

In some embodiments, the vesicle comprises a functionalized lipid. In some embodiments, the functionalized lipid is a maleimide functionalized lipid. The functionalized lipid may be a phosphoethanolamine but it is not so limited. In some embodiments, the vesicle comprises a lipid bilayer component that is functionalized, and preferably directly functionalized. In some embodiments, the vesicle comprises phosphocholine such as but not limited to DOPC. In some embodiments, the vesicle comprises phosphoglycerol such as but not limited to DOPG. In some embodiments, the vesicle comprises DOPC, DOPG and a functionalized lipid such as but not limited to a functionalized phosphoethanolamine. The functionalized lipid may be maleimide containing. In some embodiments, the vesicles comprise DOPC, DOPG and a maleimide functionalized lipid. The functionalized lipid may be a maleimide functionalized phosphoethanolamine such as but not limited to MPB. In some embodiments, the molar ratio of DOPC:DOPG:functionalized lipid is 40:10:50. In some embodiments, the vesicle may comprise DOPC and MPB. In some embodiments, the vesicles may comprise DOPC, DOTAP and MPB. In some embodiments, the molar ratio of DOPC:DOTAP:functionalized lipid is 40:10:50. In some embodiments, the functionalized lipid is present in a molar percentage of at least 25%.

In some embodiments, the vesicle comprises an agent, including one or more agents. As used herein, one or more agents intends one or more agents that are different from each other. In some embodiments, the agent is a prophylactic agent, a therapeutic agent, or a diagnostic agent. In some embodiments, the agent is an antigen. In some embodiments, the agent is a protein antigen, including a whole protein antigen. In some embodiments, the agent is an antigenic fragment of a whole protein antigen. In some embodiments, the antigen is a malarial antigen. In some embodiments, the antigen is vivax malaria protein (VMP) antigen. VMP, referred to interchangeably herein as VMP001, has an amino acid sequence of SEQ ID NO:1 and is encoded by a nucleotide sequence of SEQ ID NO:2. In some embodiments, the agent is an adjuvant. The adjuvant may be but is not limited to a TLR agonist such as TLR 4, TLR7, TLR8 and TLR9 agonists. In some embodiments, the vesicles comprise an antigen and at least two adjuvants such as a TLR4 and a TLR7 agonist. In some embodiments, the adjuvant is MPLA. In some embodiments, the agent is a protein.

In some embodiments, the vesicles comprise in excess of 300 µg of agent per mg of lipid (or particle), or in excess of 400 µg of agent per mg of lipid (or particle). In some embodiments, the vesicles comprise 300-400 µg of agent per mg of lipid (or particle). In some embodiments, the vesicles comprise 325 µg of agent per mg of lipid (or particle), or 407 µg of agent per mg of lipid (or particle). In related embodiments, the agent may be protein antigen.

In some embodiments, the agent is encapsulated within the vesicle. In some embodiments, the agent is present in the core of the vesicle. In some embodiments, the agent is present between lipid bilayers.

In some embodiments, the vesicles comprise an agent in the core and another agent in between lipid bilayers. In some embodiments, the agent in the core may be an antigen such as a protein antigen, and the agent in between the lipid bilayers may be an adjuvant such as but not limited to MPLA. In some embodiments, an antigen is in the core and two adjuvants are in between the internal lipid bilayers. The two adjuvants, in some embodiments, are MPLA and R-848. In some embodiments, the antigen is VMP.

In some embodiments, the vesicles comprise an agent in the core and another agent in the external bilayer. In some embodiments, the agent in the core may be an antigen such as a protein antigen, and the agent in the external bilayer may be an adjuvant such as but not limited to MPLA. In some embodiments, an antigen is in the core and two adjuvants are in the external bilayer. In some embodiments, an antigen is in the core and one or more adjuvants are in between the internal bilayers and/or on the external bilayer surface. The two adjuvants, in some embodiments, are MPLA and R-848. In some embodiments, the antigen is VMP.

In some embodiments, the vesicles are conjugated to polyethylene glycol (PEG). In some embodiments, the vesicles may be surface conjugated to PEG.

In another aspect, the invention provides a composition comprising any of the foregoing multilamellar lipid vesicles (or vesicle populations) and a pharmaceutically acceptable carrier.

In another aspect, the invention provides a composition comprising any of the foregoing multilamellar lipid vesicles (or vesicle populations) and an excipient suitable for lyophilization. In some embodiments, the excipient suitable for lyophilization comprises sucrose. The vesicles may be used as a stand alone or may be combined with other agents, including any of the agents described herein. In some embodiments, they will not be administered together with cells and nor will they be conjugated (or otherwise physically attached) to cells, for example prior to administration to a subject. The vesicles however may be conjugated to targeting ligands in order to target them to particular cells or sites in the body.

In another aspect, the invention provides a method comprising contacting liposomes comprising a functionalized lipid with a multivalent (e.g., divalent) cation to form fused liposomes, and contacting the fused liposomes with a crosslinker to form multilamellar lipid vesicles having crosslinks between lipid bilayers, including any of the foregoing vesicles.

In some embodiments, the functionalized lipid is a maleimide-functionalized lipid. In some embodiments, the functionalized lipid is a functionalized phosphoethanolamine. In some embodiments, the functionalized lipid is a maleimide functionalized lipid. In some embodiments, the functionalized lipid is maleimide functionalized phosphoethanolamine. In some embodiments, the liposomes comprise phosphocholine such as but not limited to DOPC. In some embodiments, the liposomes comprise phosphoglycerol such as but not limited to DOPG. In some embodiments, the liposomes comprise a maleimide-functionalized lipid, phosphocholine and phosphoglycerol. In some embodiments, the liposomes comprise DOPC, DOPG and a maleimide functionalized lipid (such as MPB) at a molar ratio of 40:10:50. In some embodiments, the liposomes comprise DOPC and a maleimide functionalized lipid such as MPB. In some embodiments, the liposomes comprise DOPC, DOTAP and a maleimide functionalized lipid (such as MPB), optionally at a molar ratio of 40:10:50.

In some embodiments, the linker is a membrane permeable linker. In some embodiments, the crosslinker is a dithiol crosslinker. In some embodiments, the crosslinker is dithiolthrietol (DTT). In some embodiments, dithiol crosslinker to maleimide functionalized lipid molar ratio is 1:2.

In some embodiments, the method further comprises conjugating polyethylene glycol (PEG) to the surface of the multilamellar lipid vesicles having crosslinks between lipid bilayers.

In some embodiments, the multivalent cations are divalent cations such as but not limited to $Ca^{2+}$ or $Mg^{2+}$. These may be used alone or in combination.

In some embodiments, the contacting occurs in an aqueous buffer.

In some embodiments, the liposomes comprise an agent. In some embodiments, the agent is a prophylactic agent, a therapeutic agent, or a diagnostic agent.

In another aspect, the invention provides a method comprising contacting a multilamellar lipid vesicle comprising a functionalized lipid bilayer component, such as a functionalized lipid, with a crosslinker to form multilamellar lipid vesicles having crosslinks between lipid bilayers.

In another aspect, the invention provides a method comprising administering to a subject a multilamellar lipid vesicle having crosslinked lipid bilayers and that comprises an agent, in an effective amount. The multilamellar lipid vesicle having crosslinked lipid bilayers may be any of the foregoing multilamellar lipid vesicles having crosslinked lipid bilayers or any of those described herein. In some embodiments, the agent is an antigen that is VMP.

In some embodiments, the multilamellar lipid vesicle comprises a biodegradable lipid. In some embodiments, the multilamellar lipid vesicle comprises a phospholipid. In some embodiments, the multilamellar lipid vesicle comprises phosphocholine, phosphoglycerol, and/or phosphoethanolamine. In some embodiments, the multilamellar lipid vesicle comprises a functionalized lipid. In some embodiments, the functionalized lipid is a maleimide functionalized lipid. In some embodiments, the maleimide functionalized lipid is a maleimide functionalized phosphoethanolamine.

In some embodiments, the agent is a prophylactic agent. In some embodiments, the agent is a therapeutic agent. In some embodiments, the agent is an antigen. In some embodiments, the antigen is VMP. In some embodiments, the agent is an adjuvant. In some embodiments, the adjuvant is MPLA. In some embodiments, the vesicles comprise two or more agents. In some embodiments, the vesicles comprise an antigen and an adjuvant. In some embodiments, the vesicles comprise an antigen and two adjuvants. In some embodiments, the vesicles comprise a protein antigen and a TLR4 agonist and a TLR7 agonist. In some embodiments, the antigen such as the protein antigen is present in the core of the vesicle and the adjuvant(s) are present in between the internal bilayers of the vesicle.

In some embodiments, the multilamellar lipid vesicle is conjugated to PEG on its external surface.

In some embodiments, the subject has or is at risk of developing cancer. In some embodiments, the subject has or is at risk of developing an infection such as but not limited to a malarial infection. In some embodiments, the subject has or is at risk of developing allergy or asthma or is experiencing or at risk of experiencing an asthmatic attack.

In some embodiments, the effective amount is an amount to stimulate an immune response in the subject. The immune response may be a humoral response, or a cellular response, or it may be a combined humoral and cellular response. The cellular response may involve stimulation of CD8 T cells.

In another aspect, the invention provides a method comprising stimulating an immune response in a subject, in need thereof, by administering multilamellar lipid vesicles having crosslinked lipid bilayers and comprising an antigen, wherein an effective amount of the antigen is administered to the subject. The multilamellar lipid vesicles having crosslinked lipid bilayers may be any of the foregoing such vesicles or any of those described herein. The vesicles may further comprise one or more adjuvants. In some embodiments, the vesicles comprise antigen, including protein antigen, in their cores and adjuvants in between their lipid bilayers. The protein antigen may be a whole protein antigen. The antigen may be VMP. The adjuvants may be but are not limited to TLR4 agonists such as MPLA and TLR7 agonists such as R-848. In some embodiments, the vesicles comprise 300-400 µg of antigen per mg of lipid. In some embodiments, the vesicles are administered only once (i.e., a priming dose is sufficient). In some embodiments, the vesicles are administered more than once (e.g., a prime and boost dose). In some embodiments, the antigen is a bacterial antigen, a viral antigen, a fungal antigen, a parasitic (e.g., malarial) antigen, or a mycobacterial antigen. In some embodiments, the antigen is a cancer antigen. In some embodiments, the immune response is a synergistic immune response.

In another aspect, the invention provides a method comprising contacting a multilamellar lipid vesicle having crosslinked lipid bilayers and that comprises an agent, with a cell, or cell population, in vitro. The cell or cell population may be dendritic cells or other antigen presenting cells. The multilamellar lipid vesicle having crosslinked lipid bilayers may be any of the foregoing multilamellar lipid vesicles having crosslinked lipid bilayers or any of those described herein. The agent may be an antigen such as VMP.

In another aspect, the invention provides a multilamellar lipid vesicle having crosslinks between functionalized lipid bilayers and comprising a terminal-cysteine-bearing antigen or a cysteine-modified antigen.

In some embodiments, the vesicle comprises phosphocholine. In some embodiments, the vesicle comprises phosphoglycerol. In some embodiments, the vesicle comprises a maleimide functionalized lipid.

In some embodiments, the antigen is present at the surface of the vesicle (and thus is presented externally). In some embodiments, the antigen is present internally. In some embodiments, the antigen is encapsulated between lipid bilayers. In some embodiments, the antigen is present in the core of the vesicle. In some embodiments, the antigen is present in the core of the vesicle and is encapsulated between the lipid bilayers of the vesicle.

In some embodiments, the antigen is present internally and at the surface of the vesicle. In some embodiments, the antigen is present at the surface of the vesicle and in the core of the vesicle. In some embodiments, the antigen is present at the surface of the vesicle and is encapsulated between the lipid bilayers of the vesicle. In some embodiments, the antigen is present at the surface of the vesicle and in the core of the vesicle and is encapsulated between the lipid bilayers of the vesicle.

In some embodiments, the antigen is a whole protein antigen. In some embodiments, the antigen is an antigenic fragment of a whole protein antigen.

In some embodiments, the antigen comprises a cysteine residue within 10 (including within 9, 8, 7, 6, 5, 4, 3 or 2 residues) of or at its amino and/or carboxy terminus. In some embodiments, the antigen comprises a cysteine residue within 5 residues of its amino terminus. In some embodiments, the antigen comprises a cysteine residue within 3 residues of its amino terminus. In some embodiments, the antigen comprises a cysteine residue within 2 residues of its amino terminus. In some embodiments, the antigen comprises a cysteine residue within 5 residues of its carboxyl terminus. In some embodiments, the antigen comprises a cysteine residue within 2 residues of its carboxyl terminus. In some embodiments, the antigen comprises a cysteine residue within 5 residues of its amino terminus and a cysteine residue within 5 residues of its carboxyl terminus.

In some embodiments, the antigen is naturally occurring. In some embodiments, the antigen is non-naturally occurring, such as for example a recombinant antigen. An example of a recombinant antigen is an antigen that has been modified to comprise one or more cysteine residues at or near it amino and/or carboxy terminus. The cysteine residue may be present at position 1, 2, 3, 4, 5, 6, 7, 8, 9 and/or 10 (where 1 is the residue at the amino terminus) and/or at position n, n−1, n−2, n−3, n−4, n−5, n−6, n−7, n−8, n−9 and/or n−10 (where n is the residue at the carboxy terminus).

In some embodiments, the antigen is a microbial antigen. In some embodiments, the antigen is VMP. In some embodiments, the antigen is not VMP.

In some embodiments, 5-15% of the antigen is surface-conjugated. In some embodiments, the vesicle comprises about 40-50 µg of antigen per mg of lipid. In some embodiments, the vesicle comprises about 4-5 µg of surface-conjugated antigen per mg of lipid. In some embodiments, the vesicle has a hydrodynamic diameter in the range of 150-200 nm.

In some embodiments, the vesicle further comprises an adjuvant such as but not limited to MPLA.

In some embodiments, the vesicle is surface-conjugated to polyethylene glycol (PEG).

In another aspect, the invention provides a composition comprising any one or a combination of the foregoing multilamellar lipid vesicles having crosslinks between functionalized lipid bilayers and comprising a terminal-cysteine-bearing antigen or a cysteine-modified antigen. In some embodiments, the antigen is VMP. In some embodiments, the antigen is not VMP.

In another aspect, the invention provides a composition comprising a pharmaceutically acceptable carrier and any one or a combination of the foregoing multilamellar lipid vesicles having crosslinks between functionalized lipid bilayers and comprising a terminal-cysteine-bearing antigen or a cysteine-modified antigen. In some embodiments, the antigen is VMP. In some embodiments, the antigen is not VMP.

In another aspect, the invention provides a composition comprising an adjuvant and any one or a combination of the foregoing multilamellar lipid vesicles having crosslinks between functionalized lipid bilayers and comprising a terminal-cysteine-bearing antigen or a cysteine-modified antigen. In some embodiments, the antigen is VMP. In some embodiments, the antigen is not VMP.

In another aspect, the invention provides a composition comprising any one or a combination of the foregoing multilamellar lipid vesicles having crosslinks between functionalized lipid bilayers and comprising a terminal-cysteine-bearing antigen or a cysteine-modified antigen, wherein the vesicles are lyophilized. In some embodiments, the antigen is VMP. In some embodiments, the antigen is not VMP.

In another aspect, the invention provides a method comprising contacting a functionalized lipid and a non-functionalized lipid with a terminal-cysteine-bearing antigen to form liposomes, and contacting the liposomes with a thiol crosslinker and a divalent cation to form multilamellar lipid vesicles comprising a terminal-cysteine-bearing antigen or a cysteine-modified antigen.

In some embodiments, the functionalized lipid is a maleimide-functionalized lipid. In some embodiments, the functionalized lipid is a functionalized phosphoethanolamine. In some embodiments, the functionalized lipid is maleimide-functionalized phosphoethanolamine.

In some embodiments, the non-functionalized lipid is phosphocholine. In some embodiments, the non-functionalized lipid is phosphoglycerol. In some embodiments, the liposomes comprise a maleimide-functionalized lipid, phosphocholine and phosphoglycerol.

In some embodiments, the crosslinker is a dithiol crosslinker. In some embodiments, the crosslinker is dithiolthrietol (DTT).

In some embodiments, the method further comprises conjugating polyethylene glycol (PEG) to the surface of the multilamellar lipid vesicles.

In some embodiments, the divalent cation is $Ca^{2+}$. In some embodiments, the divalent cation is $Mg^{2+}$.

In some embodiments, the terminal-cysteine-bearing antigen is a whole protein antigen. In some embodiments, the terminal-cysteine-bearing antigen is an antigenic fragment of a whole protein antigen. In some embodiments, the cysteine-modified antigen comprises a whole protein antigen or an antigenic fragment of a whole protein antigen. In some embodiments, the terminal-cysteine-bearing antigen or the cysteine-modified antigen comprises a cysteine residue within 5 residues of its amino terminus. In some embodiments, the terminal-cysteine-bearing antigen or the cysteine-modified antigen comprises a cysteine residue within 3 residues of its amino terminus. In some embodiments, the terminal-cysteine-bearing antigen or the cysteine-modified antigen comprises a cysteine residue within 5 residues of its carboxyl terminus. In some embodiments, the terminal-cysteine-bearing antigen or the cysteine-modified antigen comprises a cysteine residue within 2 residues of its carboxyl terminus. In some embodiments, the terminal-cysteine-bearing antigen or the cysteine-modified antigen comprises a cysteine residue within 5 residues of its amino terminus and a cysteine residue within 5 residues of its carboxyl terminus. In some embodiments, the terminal-cysteine-bearing antigen is a microbial antigen. In some embodiments, the cysteine-modified antigen comprises a microbial antigen. In some embodiments, the terminal-cysteine-bearing antigen is naturally occurring. In some embodiments, the antigen is VMP. In some embodiments, the antigen is not VMP.

In another aspect, the invention provides a method comprising administering to a subject a multilamellar lipid vesicle with an adjuvant, in an effective amount to stimulate an immune response, wherein the vesicle has crosslinks between functionalized lipid bilayers and comprises a terminal-cysteine-bearing antigen or a cysteine-modified antigen. In some embodiments, the antigen is VMP. In some embodiments, the antigen is not VMP.

In some embodiments, the immune response is a balanced Th1/Th2 immune response. In some embodiments, the immune response is sustained for 1 year.

In some embodiments, the adjuvant is MPLA. In some embodiments, adjuvant dose is reduced up to 10-fold to 100-fold relative to adjuvant dose required with soluble antigen.

In some embodiments, antigen dose is reduced up to 10-fold relative to a dose required with a soluble antigen (i.e., a soluble antigen dose).

In some embodiments, the multilamellar lipid vesicle is administered as a prime dose.

In another aspect, the invention provides a method comprising contacting one or a combination of multilamellar lipid vesicles having crosslinks between functionalized lipid bilayers and comprising a terminal-cysteine-bearing antigen or a cysteine-modified antigen, with a cell in vitro.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF DRAWINGS

FIGS. 6A-B 6. OVA released from sonicated liposomes, MLVs fused by $Mg^{2+}$ and ICMVs formed by $Mg^{2+}$ and DTT in (A) PBS and (B) RPMI media with 10% serum.

DETAILED DESCRIPTION OF INVENTION

Figure 1A:
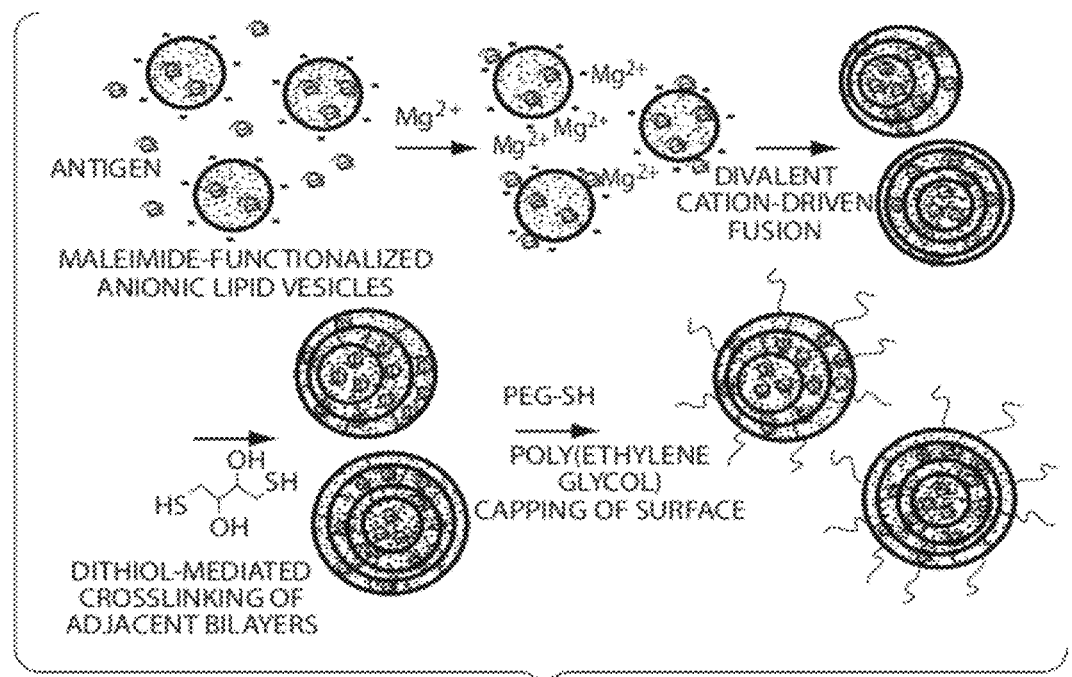
FIG. 1A. Schematic of synthesis of interbilayer-crosslinked multilamellar vesicles (ICMVs). Divalent cation-mediated fusion leads to formation of multilamellar vesicles, in which adjacent bilayers were crosslinked with DTT. The resulting ICMVs were PEGylated in a reaction with PEG-thiol.

The invention provides stabilized multilamellar lipid vesicles for use in, inter alia, delivery of agents. Prior art vaccines based on recombinant proteins avoid toxicity and anti-vector immunity associated with live vaccine (e.g., viral) vectors, but their immunogenicity is poor, particularly for CD8$^+$ T-cell (CD8T) responses. Synthetic particles carrying antigens and adjuvant molecules have been developed to enhance subunit vaccines, but in general these materials have failed to elicit CD8T responses comparable to live vectors in preclinical animal models. In contrast to these prior art compositions and methods, the invention provides stabilized multilamellar vesicles, such as interbilayer-crosslinked multilamellar vesicles (ICMVs) formed by crosslinking headgroups of adjacent lipid bilayers within multilamellar vesicles. These vesicles stably entrap, inter alia, protein antigens in the vesicle core and lipid-based immunostimulatory molecules in the vesicle walls under extracellular conditions, but exhibited rapid release in the presence of endolysosomal lipases. When used to deliver antigen alone or in the presence of adjuvant, the vesicles of the invention form an extremely potent vaccine (e.g., a whole-protein vaccine), eliciting endogenous T-cell and antibody responses comparable to the strongest vaccine vectors.

The vesicles are stabilized by internal linking (e.g., crosslinking) of their lipid bilayers. The stabilized nature of these vesicles allows them to incorporate higher amounts of agents and to retain such agents over a longer time period, as compared to simple liposomes or lipid coated nano- or microparticles. Their sustained release kinetics, particularly in the presence of serum, make them useful in in vivo delivery of agents for which a slow, steady and prolonged release is desirable or for which slow release in the extracellular environment but rapid release within cells is desirable. The invention contemplates using such vesicles with a number and variety of agents including prophylactic agents, therapeutic agents, and/or diagnostic agents, as described in greater detail herein. The invention therefore provides compositions comprising the afore-mentioned vesicles, methods for their synthesis, and methods for their use.

Stabilized Multilamellar Lipid Vesicles (MLV)

The invention provides MLV that are stabilized by linking adjacent (or apposed) lipid bilayers to one another. As used herein, a multilamellar vesicle is a nano- or microsphere having a shell that is comprised of two or more concentrically arranged lipid bilayers. As used herein, adjacent or apposed lipid bilayers (or lipid bilayer surfaces) intend bilayers or surfaces that are in close proximity to each other but that are otherwise distinct and typically physically separate. This term does not typically mean the relationship between the two monolayers of a single bilayer.

As used herein, "linking" means two entities stably bound to one another by any physiochemical means. Any linkage known to those of ordinary skill in the art may be employed including covalent or noncovalent linkage, although covalent linkage is preferred. In some important embodiments described herein, covalent linkage between adjacent (or apposed) lipid bilayers in MLV is achieved through the use of crosslinkers and functionalized components of the lipid bilayer. The invention however contemplates that linking, including covalent linking, may be effected in other ways. As an example, the invention contemplates methods in which complementary reactive groups reside on components of adjacent bilayer surfaces and linkage between the bilayer surfaces is effected by reacting those groups to each other even in the absence of a crosslinker. Suitable complementary reactive groups are known in the art and described herein.

The interior of the vesicle is typically an aqueous environment, and it may comprise an agent such as but not limited to a prophylactic, therapeutic or diagnostic agent. In some instances, the vesicles do not comprise a solid core, such as a solid polymer core (e.g., a synthetic polymer core). Instead, as discussed above, they may have a fluid core comprising agents of interest. The core may comprise monomers for polymerization into a hydrogel core in some instances. The vesicles may also be referred to herein as particles, including nano- or microparticles, although it is to be understood that such nano- or micro-particles have the attributes of the stabilized MLVs and interbilayer crosslinked multilamellar lipid vesicles (ICMVs) of the invention.

Figure 1B:
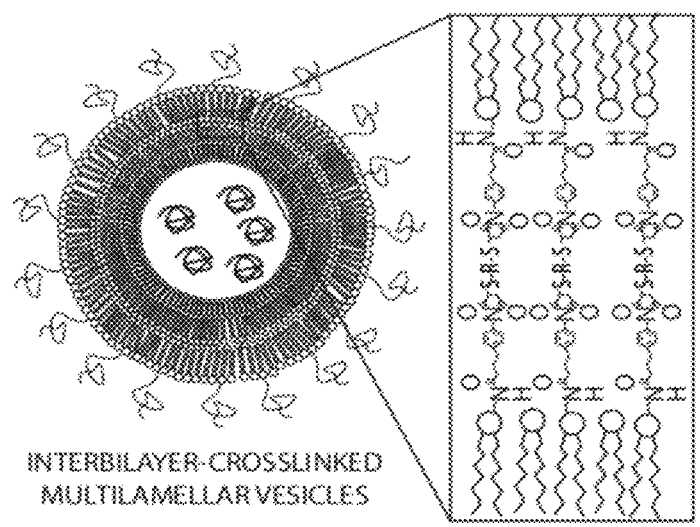
FIG. 1B. Illustration of ICMVs formed by conjugating two lipid headgroups together in multilamellar vesicles.
Figures 1, 2A:
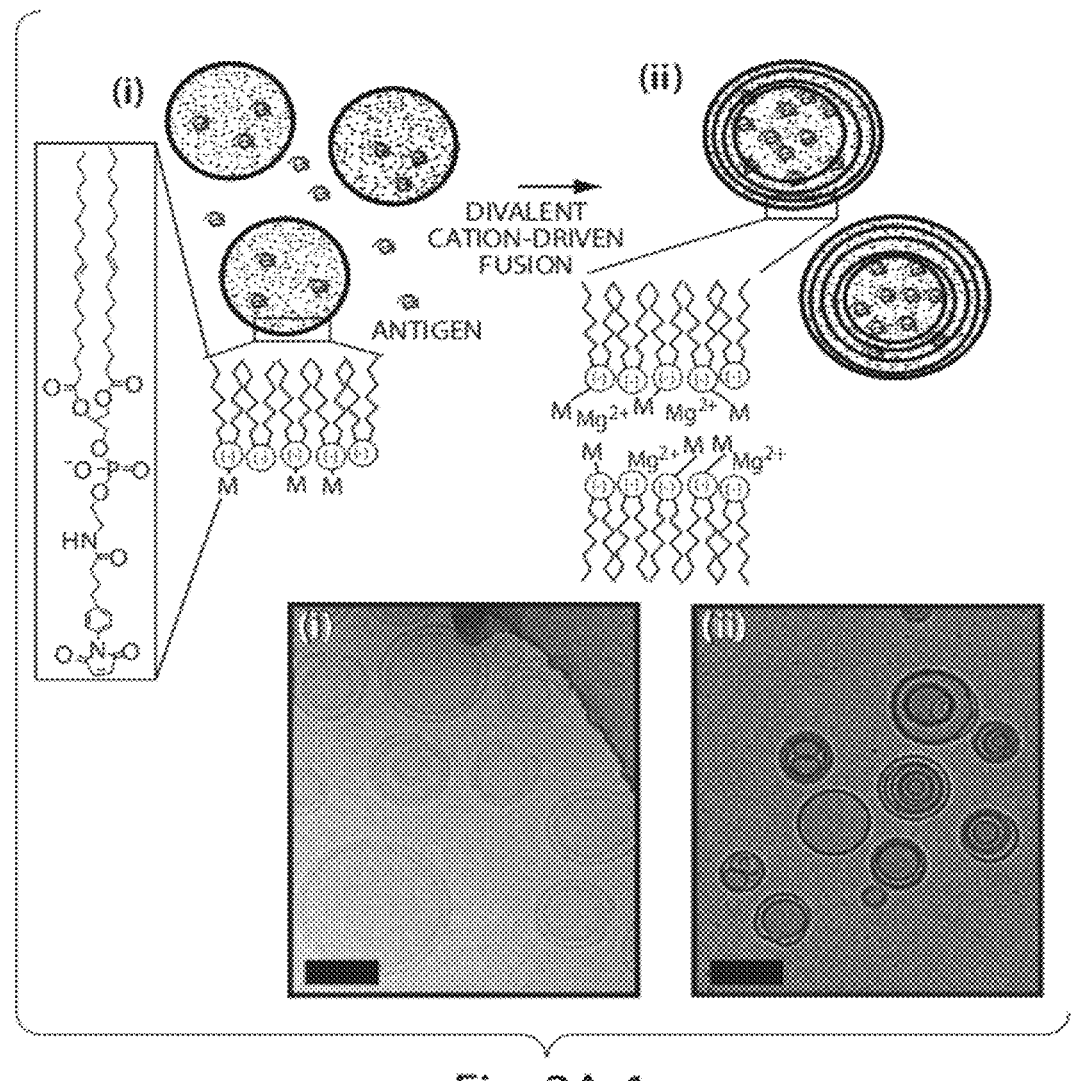
FIGS. 2A-D. Synthesis of ICMVs. (A) Schematic illustration of ICMV synthesis and cryoelectron microscope images: (i) Anionic, maleimide-functionalized liposomes are prepared from dried lipid films, (ii) divalent cations are added to induce fusion of liposomes and the formation of MLVs, (iii) membrane-permeable dithiols are added, which crosslink maleimide-lipids on apposed lipid bilayers in the vesicle walls, and (iv) the resulting lipid particles are PEGylated with thiol-terminated PEG. Cryo-EM images from each step of the synthesis show (i) initial liposomes, (ii) MLVs, and (iii) ICMVs with thick lipid walls. Scale bars=100 nm. Right-hand image of (iii) shows a zoomed image of an ICMV wall, where stacked bilayers are resolved as electron-dense striations; scale bar=20 nm. (B) ICMV particle size histogram measured by dynamic light scattering. (C, D) Histograms of ICMV properties from cryo-EM images show (C) the number of lipid bilayers per particle, and (D) the ratio of particle radius to lipid wall thickness. (n=165 particles analyzed).
Figures 2, 2A:
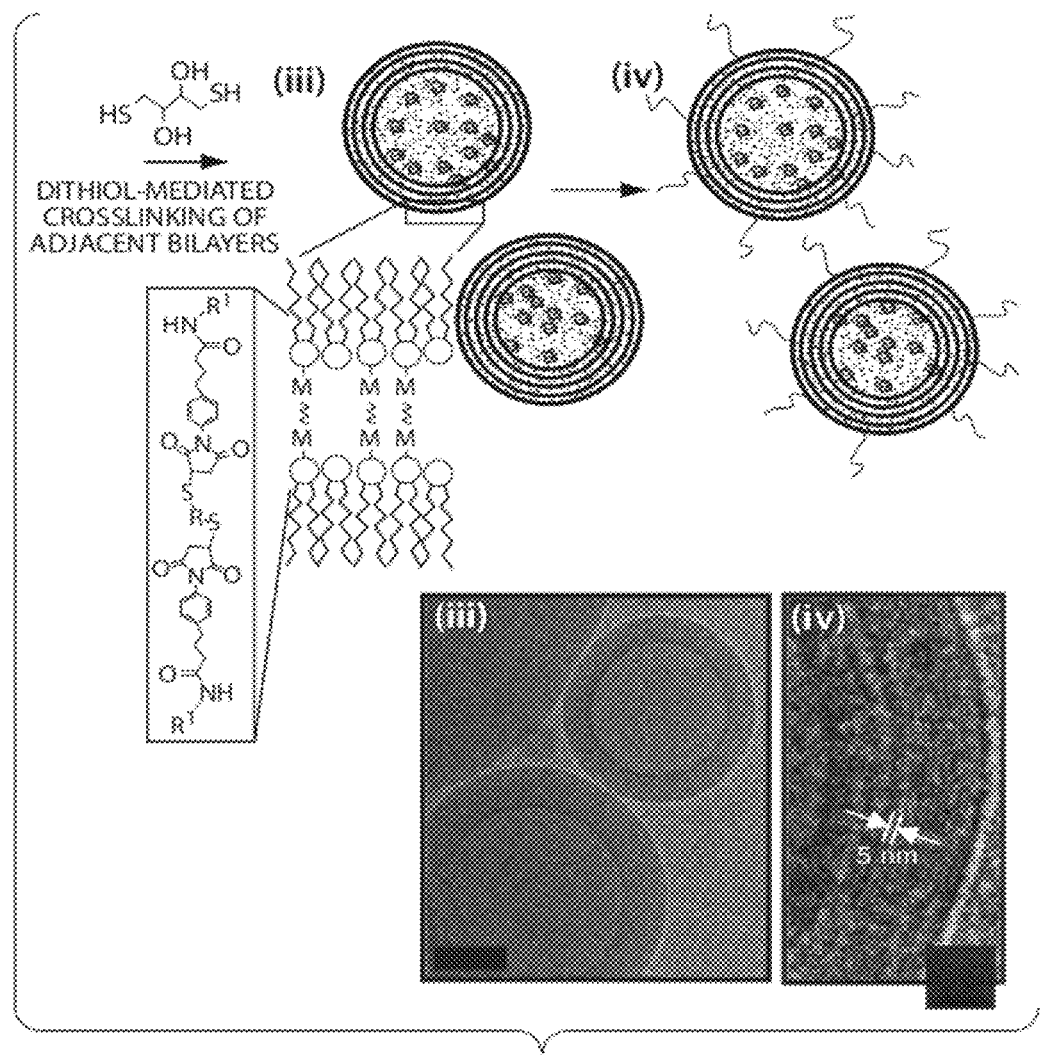

The vesicles may have a void volume at their core and/or they may comprise one or more agents in their core and/or between adjacent (or apposing) lipid bilayers, as shown in FIGS. 1A, 1B and 2A. The vesicles may also comprise one or more agents on their surface. Thus, in some instances, the vesicles may comprise agents on their surface, between their lipid bilayers, and in their core. The agents are typically included in the lipid solution during the synthesis process and in this manner are incorporated (e.g., by encapsulation) into the vesicles during synthesis. Lipophilic molecules may also be incorporated directly into the lipid bilayers as the vesicles are formed or molecules with lipophilic tails may be anchored to the lipid bilayers during vesicle formation. The vesicles may be produced in the absence of harsh solvents, such as organic solvents, and as a result they may be able to encapsulate a wide variety of agents including those that would be susceptible to organic solvents and the like.

The amount of agent in the vesicles may vary and may depend on the nature of the agent. As demonstrated in the Examples, 300-400 µg of protein agent per mg of lipid may be incorporated into the vesicles of the invention. In some embodiments, the vesicles may comprise about 100 µg of agent, or about 150 µg of agent, or about 200 µg of agent, or about 250 µg of agent, or about 300 µg of agent, or about 325

μg of agent, or about 350 μg of agent, or about 375 μg of agent, or about 400 μg of agent, or about 410 μg of agent, per mg of lipid. In some embodiments, the agent may be a protein such as a protein antigen.

The vesicles of the invention may also be characterized by their retention profiles. In some embodiments, the vesicles release agent at a rate of about 25% per week when placed in serum containing media (e.g., 10% serum) and maintained at 37° C. In some embodiments, the vesicles release about 25% of agent in the first week and up to about 90% after about 30 days under these conditions. In some embodiments, the vesicles maintain at least 80%, at least 85%, at least 90%, or at least 95% of their agent when stored in buffer (such as PBS) at 4° C. for 30 days.

The number of lipid bilayers in each vesicle may vary, with a typical range of at least 2 to about 50, or at least 2 to about 25, or at least 2 to about 15, or at least 2 to about 10, or at least 2 to about 5.

Figure 2B:
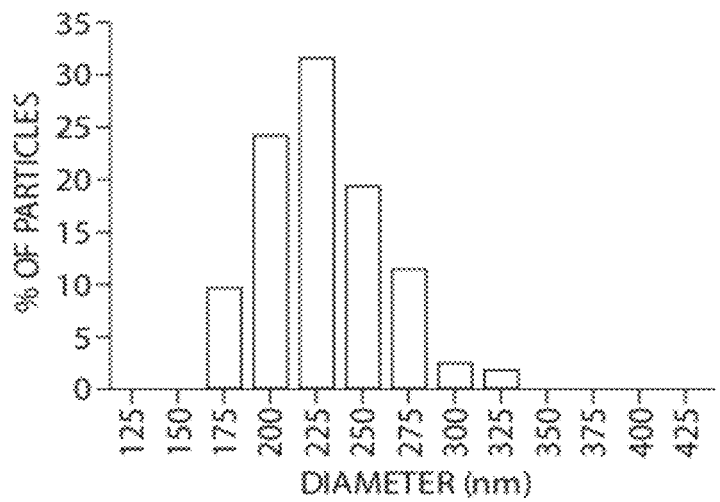
Figure 3A:
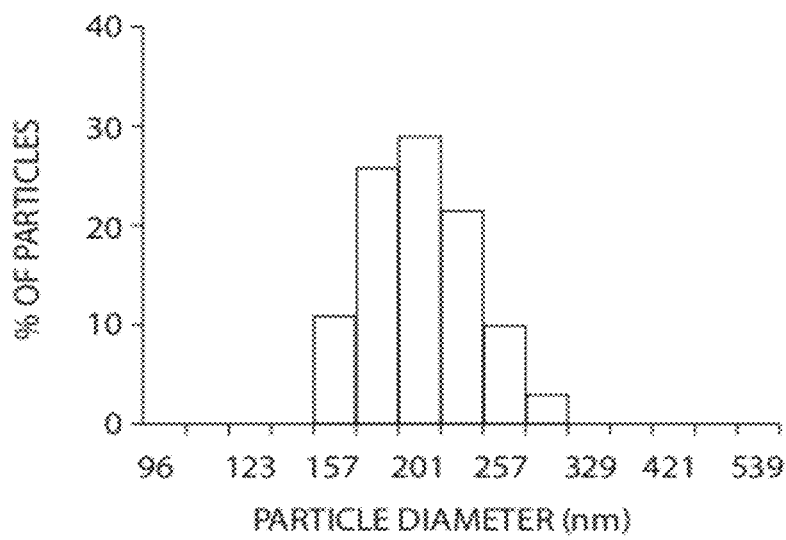
FIGS. 3A-B. (A) Histogram of particle diameters measured by dynamic light scattering. (B) Cryo-EM image of ICMV particle.

The diameter of the vesicles may vary. In some instances, the vesicles will have a diameter ranging from about 100 to about 500 nm, including from about 125 to about 300 nm, including from about 150 to about 300 nm, including from about 175 to about 275 nm. In some instances, the diameter ranges from about 150 to about 250 nm. The diameter profiles for ICMV prepared as described in the Examples is shown in FIGS. 2B and 3A. It will be understood that, in any preparation of vesicles, there will be heterogeneity between vesicles relating to vesicle diameter, number of lipid bilayers, amount of loaded agent, etc. Such distributions are shown in the Examples.

As used herein, the vesicles of the invention may also be referred to as liposomes (e.g., stabilized multilamellar liposomes or, as discussed below, interbilayer crosslinked multilamellar liposomes). Accordingly, the use of the term "vesicles" is not intended to convey source or origin of the vesicles. The vesicles of the invention are synthetic vesicles (i.e., they are produced in vitro), as will be discussed in greater detail below.

The vesicles may be isolated, intending that they are physically separated in whole or in part from the environment in which they are synthesized. As an example, vesicles comprising an agent (i.e., their "cargo" or "payload") may be separated in whole or in part from vesicles lacking agent (i.e., empty vesicles), and may then be referred to as "isolated vesicles." Separation may occur based on weight (or mass), density (including buoyant density), size, color and the like (e.g., where the cargo of the vesicle is detectable by its energy emission), etc. As described in the Examples, centrifugation can be used to separate vesicles of the invention from simple liposomes or MLVs of identical lipid composition that do not have crosslinked bilayers. Centrifugation at about 14,000 g for about 4 minutes is sufficient to separate the vesicles of the invention, which pellet, from these other particle types.

Interbilayer Crosslinked Multilamellar Lipid Vesicles

Figure 2C:
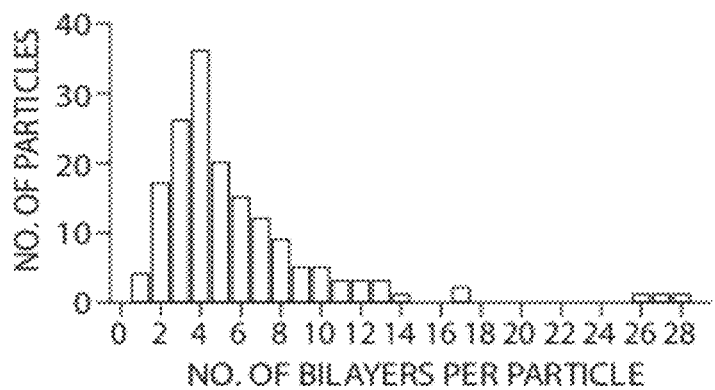
Figure 2D:
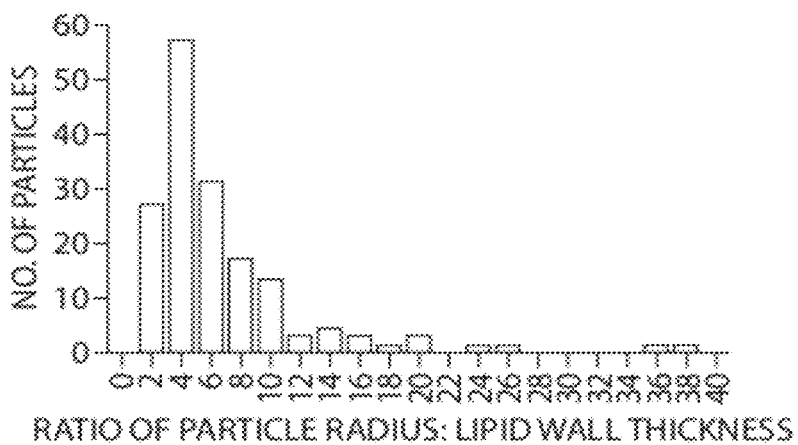

An example of the stabilized MLV of the invention is the interbilayer crosslinked multilamellar (lipid) vesicles (ICMV). Like the stabilized MLV described above, ICMV are nano- or microspheres having a shell that is comprised of two or more concentrically arranged lipid bilayers that are conjugated to each other as described herein. The number of lipid bilayers in the stabilized multilamellar vesicles, including the ICMV, may vary from about 2-30, but is more commonly in the range of 2-15. Accordingly, in various embodiments, the number of layers may be 2, 3, 4, 5, 6, 7, 8, 9, 10, 11, 12, 13, 14, 15 or more. The frequency distribution of bilayer numbers resulting from one exemplary synthesis of ICMV is shown in FIG. 2C. The bilayers are typically comprised of lipids having hydrophilic heads and hydrophobic tails that are arranged in a manner similar to a cell membrane (i.e., with the hydrophilic heads exposed to typically an aqueous environment and the hydrophobic tails buried in the bilayer).

The ICMV are stabilized via crosslinks between their lipid bilayers, and they are therefore referred to as "interbilayer crosslinked" MLV. As used herein, this means that at least two lipid bilayers in the shell of the vesicle are crosslinked to each other. The crosslinked bilayers are typically those that are apposed or adjacent to each other. Most or all of the lipid bilayers in the shell may be crosslinked to their apposing lipid bilayer in the shell. There may be one or more crosslinks between lipid bilayers. Typically, there will be numerous crosslinks between lipid bilayers. The arrangement and positioning of such crosslinks may be random or non-random. The degree of crosslinks (and thus the resultant stability of the vesicles) will depend upon the proportion of functionalized lipids (or other lipid bilayer components) used to make the vesicles and the crosslinking conditions (including, for example, time of incubation of the vesicles with a crosslinker). It will be understood that the higher the proportion of functionalized lipids (or other lipid bilayer components) in the vesicles, the more crosslinks that will be formed, all other factors and parameters being equal. Similarly, the more favorable the conditions towards crosslinking, the greater degree of crosslinking that will be achieved.

ICMV and Cysteine-Bearing Agents and Antigens

The invention contemplates ICMVs comprising cysteine-bearing agents including cysteine-bearing antigens. Such cysteine-bearing agents include terminal-cysteine-bearing agents such as terminal-cysteine-bearing antigens. It has been found in accordance with the invention that ICMVs comprising such antigens are able to induce robust and long-lived immune responses in vivo, as discussed in greater detail in the Examples. Terminal-cysteine-bearing antigens, as defined herein, are antigens that comprise one or more cysteine residues within 10 amino acid residues of the amino terminus (i.e., at amino acid positions 1 through 10) and/or within 10 amino acid residues of the carboxy terminus (i.e., at amino acids (n−10) through n, where n represents the number of amino acid residues in the antigen). Thus, cysteines may occupy positions 1, 2, 3, 4, 5, 6, 7, 8, 9, 10, n−10, n−9, n−8, n−7, n−6, n−5, n−4, n−3, n−2, n−1 and/or n, where 1 represents the residue at the amino terminus and n represents the residue at the carboxy terminus. In some instances, one or more cysteine residues may be present within 5 amino acid residues of the amino terminus and/or within 5 amino acid residues of the carboxy terminus. In some instances, the antigen may comprise a cysteine residue within four, three, or two amino acids of either or both ends of the antigen. In some instances, the antigen may comprise a cysteine residue at the amino and/or carboxy terminus. The antigen may also comprise internal cysteine residues (i.e., cysteine residues between amino acid positions 10 and (n−10) wherein n represents the number of amino acid residues in the antigen). The total number of cysteines in the antigen may vary. The antigen may comprise 2, 3, 4, 5 or more cysteine residues.

The terminal-cysteine-bearing antigens may be naturally occurring or they may be non-naturally occurring. An example of a non-naturally occurring antigen is a recombinant antigen.

The invention further contemplates cysteine-modified antigens and their use with the ICMVs of the invention. Cysteine-modified antigens, as defined herein, are antigens that have been modified by the addition of one or more cysteines at or near one or both of their termini. Such antigens may comprise naturally occurring amino acid sequence that is modified by the addition of one or more cysteines at one or both of its termini. Such modifications can be made using standard recombinant DNA techniques. Such modifications may also be made for example through the use of heterobifunctional crosslinkers that bind the pre-modified form of the antigen and the cysteine-bearing sequence being added. An example is the STAT-PEG crosslinker which has an NHS group that binds to free amines (such as those on peptides and proteins) and a protected thiols. In this manner such a crosslinker may be used to thiolate peptides and proteins. The cysteine-modified antigens may comprise one or more cysteines within 10 residues of the amino terminus (i.e., positions 1 through 10) and/or within 10 residues of the carboxy terminus (i.e., positions (n−10) through n, where n represents the number of amino acids in the cysteine-modified antigen. An antigen may be modified to comprise one or more cysteines within 10, 9, 8, 7, 6, 5, 4, 3 or 2 residues of the amino terminus (or at the amino terminus) and/or 10, 9, 8, 7, 6, 5, 4, 3 or 2 residues of the carboxy terminus (or at the carboxy terminus). The invention contemplates the modification of any of the antigens provided herein to include one or more cysteine residues within 10 residues of the amino terminus and/or within 10 residues of the carboxy terminus. In this manner, any antigen may be used with the ICMVs of the invention, and the immune response to such antigen may be enhanced. The ability of such modification to enhance the immune stimulating activity of an antigen to the degree shown herein was unexpected.

Synthesis Methods

An exemplary synthesis method is as follows: Lipids and optionally other bilayer components are combined to form a homogenous mixture. This may occur through a drying step in which the lipids are dried to form a lipid film. The lipids are then combined (e.g., rehydrated) with an aqueous solvent. The aqueous solvent may have a pH in the range of about 6 to about 8, including a pH of about 7. Buffers compatible with vesicle fusion are used, typically with low concentrations of salt. The solvent used in the Examples is a 10 mM bis-tris propane (BTP) buffer pH 7.0. The nature of the buffer may impact the length of the incubation, as shown in Table 1A. For example, a buffer such as PBS may require a longer incubation time as compared to a buffer such as BTP, all other things being equal. If the buffer is PBS, then the incubation times may be about 6-24 hours, or 8-16 hours, or 10-12 hours. If the buffer is BTP, then the incubation times may be shorter including 1-4 hours, or 1-2 hours. Accordingly a variety of aqueous buffers may be used provided that a sufficient incubation time is also used. This step may also include the presence of the agent(s) to be incorporated into the vesicles. The resultant liposomes are then incubated with one or more divalent cations in order to fuse them into multilamellar vesicles. Suitable divalent cations include $Mg^{2+}$, $Ca^{2+}$, $Ba^{2+}$, or $Sr^{2+}$. Multivalent or polymeric cations could also be employed for vesicle fusion. Vesicle fusion could also be achieved via the mixing of cationic vesicles with divalent or higher valency anions; an example would be fusion of cationic liposomes with DNA oligonucleotides or DNA plasmids. This may be done under agitation such as sonication, vortexing, and the like. If the liposomes were made in the presence of an agent, the MLVs will comprise the agent in their core and/or between the concentrically arranged lipid bilayers. The invention contemplates fusion of liposomes carrying different agents to form MLVs that comprise such agents.

Figure 12A:
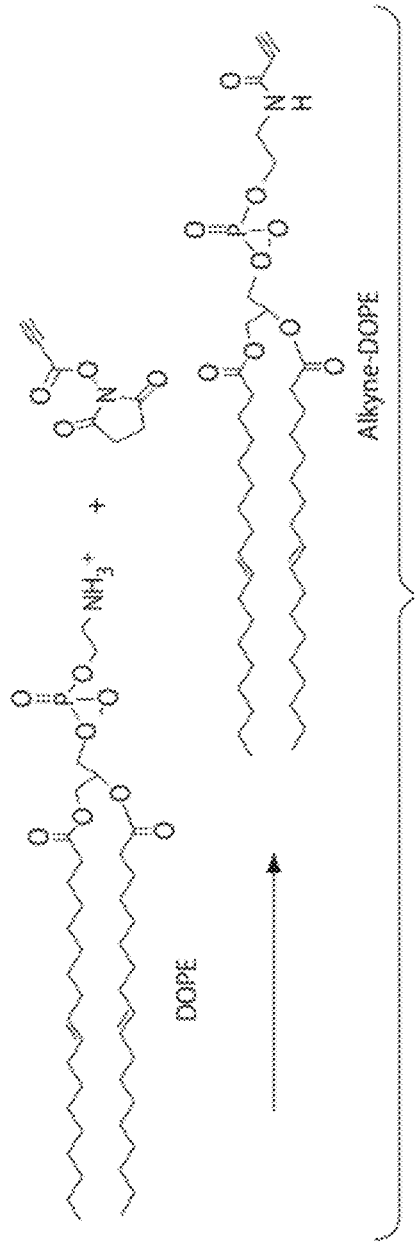
FIGS. 12A-B. Alternative interbilayer-crosslinked reaction using "click" chemistry. (A) An alkyne-headgroup lipid was synthesized from DOPE and an alkyne precursor. (B) Liposomes were formed with alkyne-terminated lipids and induced to form MLVs by $Mg^{2+}$. Subsequent incubation of the alkyne-bearing MLVs with diazide and catalyst as indicated led to successful formation of ICMVs with 83% particle yield, as measured after particle retrieval with low-speed centrifugation conditions.
Figure 12B:
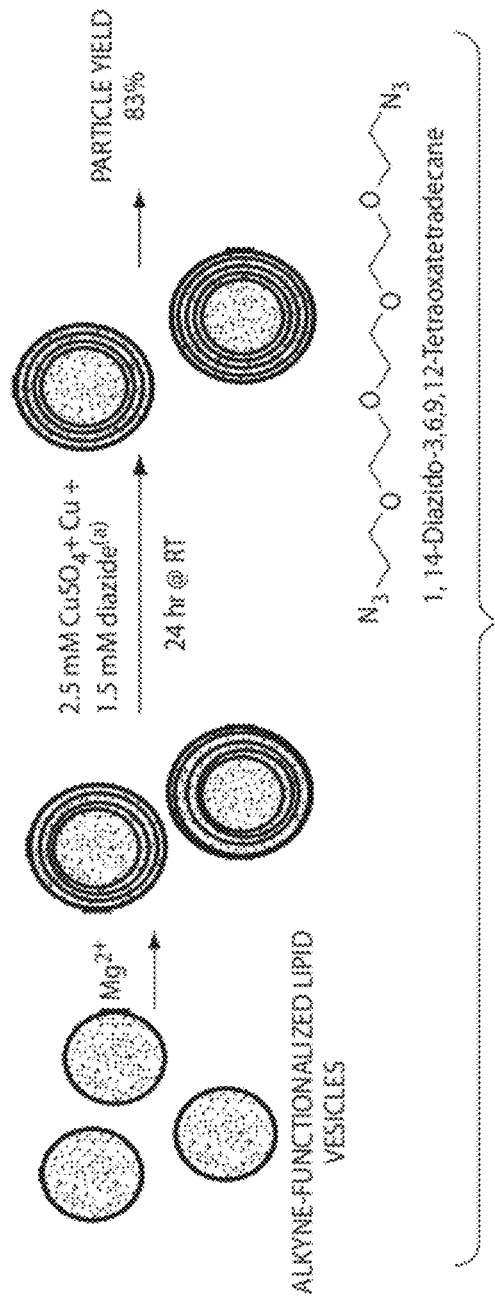

The resultant MLVs are then incubated with a crosslinker, and preferably a membrane-permeable crosslinker. As stated herein, the nature of the crosslinker will vary depending on the nature of the reactive groups being linked together. As demonstrated in the Examples, a dithiol-containing crosslinker such as DTT or (1,4-Di-[3'-(2'-pyridyldithio)-propionamido]butane) may be used to crosslink MLVs comprised of maleimide functionalized lipids (or other functionalized lipid bilayer components), or diazide crosslinkers could be used to crosslink alkyne headgroup lipids via "click" chemistry, as shown in FIG. 12. These various incubations are all carried out under aqueous conditions at a pH in the range of about 6 to about 8, or about 6.5 to about 7.5, or at about 7. The crosslinking step may be performed at room temperature (e.g., 20-25° C.) or at an elevated temperature including for example up to or higher than 37° C.

The resultant crosslinked vesicles may then be collected (e.g., by centrifugation or other pelleting means), washed and then PEGylated on their outermost or external surface (e.g., as used herein, the vesicles may be referred to "surface-PEGylated" or "surface-conjugated" to PEG) by incubation with a thiol-PEG. The PEG may be of any size, including but not limited to 0.1-10 kDa, 0.5-5 kDa, or 1-3 kDa. A 2 kDa PEG functionalized with thiol is used in the Examples. The incubation period may range from about 10 minutes to 2 hours, although it may be shorter or longer depending on other conditions such as temperature, concentration and the like. The PEGylation step may be performed at room temperature (e.g., 20-25° C.) or at an elevated temperature including for example up to or higher than 37° C. A 30 minute incubation period is used in the exemplary synthesis methods of the Examples. The vesicles then may be collected (e.g., by centrifugation or other pelleting means) and washed with water or other aqueous buffer.

The vesicles may be stored at 4° C. in a buffered solution such as but not limited to PBS or they may be lyophilized in the presence of suitable cryopreservants and then stored at −20° C. Suitable cryopreservants include those that include sucrose (e.g., a 1-5% sucrose, and preferably about 3% sucrose solution).

Crosslinking could also be achieved by coupling between a reactive group in one bilayer with a complementary reactive group in the adjacent bilayer. For example, fused vesicles containing succinimidyl ester-functionalized lipid (A) headgroups and primary-amine-containing (B) headgroups could achieve crosslinking by in situ reaction between the A and B lipids of adjacent bilayers. A variety of other complementary functionalized lipids familiar to those skilled in the art could be employed in a similar manner.

The molar ratio of functionalized lipid (or other functionalized component of the lipid bilayer) to crosslinker may vary depending on the conditions. In some instances, it may range from about 1 to about 5. In some embodiments, a molar ratio of 2 is sufficient (i.e., the molar ratio of functionalized lipid (or component) to crosslinker is 2:1). The Examples describe a synthesis method in which a 2:1 molar ratio of maleimide functionalized lipid to DTT is used to crosslink the lipid bilayers of the vesicles. The incubation time may range from 1 hour to 24 hours, from 2-18 hours, from 2 to 12 hours, or from 2 to 6 hours. In some instances, it may be about 2 hours. In other instances, it may be overnight (e.g., about 12 hours).

The molar % of the functionalized lipid in the vesicles may range from 1% to 100%, or from about 10% to about 60% in some instances, or from about 25% to about 55% in some instances. In some instances, the molar % of the functionalized lipid in the vesicles is typically at least 10%, preferably at least 15%, more preferably at least 20%, and even more preferably at least 25%. Tables 1A and 1B show that in the absence of functionalized lipid, no vesicles are formed.

Conversely, the non-functionalized lipids may be present at about 0% to 99% as a molar %. More typically, the non-functionalized lipids may be present at about 40%-75% or 40% to 60% as a molar %.

In one important embodiment, the vesicles are synthesized using DOPC, DOPG and maleimide-functionalized DSPE. The ratio of these lipids to each other may vary. Tables 1A and 1B show the effects of varying, the ratio of DOPC:DOPG:maleimide functionalized lipid on vesicle yield. The molar % of DOPC may range from 1-50%, the molar % of DOPG may range from 1-50%, and the molar % of the maleimide functionalized lipid may range from 1-80%. Some embodiments of the invention provide vesicles having a DOPC:DOPG:maleimide functionalized lipid ratio of 40:10:50. Some embodiments provide vesicles having a DOPC:DOPG:maleimide functionalized lipid ratio of 60:15:25. Some embodiments provide vesicles comprised of DOPG and a maleimide functionalized lipid.

Lipids

The vesicles are comprised of one or more lipids. The type, number and ratio of lipids may vary with the proviso that collectively they form spherical bilayers (i.e., vesicles). The lipids may be isolated from a naturally occurring source or they may be synthesized apart from any naturally occurring source.

At least one (or some) of the lipids is/are amphipathic lipids, defined as having a hydrophilic and a hydrophobic portion (typically a hydrophilic head and a hydrophobic tail). The hydrophobic portion typically orients into a hydrophobic phase (e.g., within the bilayer), while the hydrophilic portion typically orients toward the aqueous phase (e.g., outside the bilayer, and possibly between adjacent apposed bilayer surfaces). The hydrophilic portion may comprise polar or charged groups such as carbohydrates, phosphate, carboxylic, sulfato, amino, sulfhydryl, nitro, hydroxy and other like groups. The hydrophobic portion may comprise apolar groups that include without limitation long chain saturated and unsaturated aliphatic hydrocarbon groups and groups substituted by one or more aromatic, cyclo-aliphatic or heterocyclic group(s). Examples of amphipathic compounds include, but are not limited to, phospholipids, aminolipids and sphingolipids.

Typically, the lipids are phospholipids. Phospholipids include without limitation phosphatidylcholine, phosphatidylethanolamine, phosphatidylglycerol, phosphatidylinositol, phosphatidylserine, and the like. It is to be understood that other lipid membrane components, such as cholesterol, sphingomyelin, cardiolipin, etc. may be used.

The lipids may be anionic and neutral (including zwitterionic and polar) lipids including anionic and neutral phospholipids. Neutral lipids exist in an uncharged or neutral zwitterionic form at a selected pH. At physiological pH, such lipids include, for example, dioleoylphosphatidylglycerol (DOPG), diacylphosphatidylcholine, diacylphosphatidylethanolamine, ceramide, sphingomyelin, cephalin, cholesterol, cerebrosides and diacylglycerols. Examples of zwitterionic lipids include without limitation dioleoylphosphatidylcholine (DOPC), dimyristoylphosphatidylcholine (DMPC), and dioleoylphosphatidylserine (DOPS). An anionic lipid is a lipid that is negatively charged at physiological pH. These lipids include without limitation phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), and other anionic modifying groups joined to neutral lipids.

Collectively, anionic and neutral lipids are referred to herein as non-cationic lipids. Such lipids may contain phosphorus but they are not so limited. Examples of non-cationic lipids include lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidyl-ethanolamine (DSPE), palmitoyloleoyl-phosphatidylethanolamine (POPE) palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleoylphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), phosphatidylserine, phosphatidylinositol, sphingomyelin, cephalin, cardiolipin, phosphatidic acid, cerebrosides, dicetylphosphate, and cholesterol.

Additional nonphosphorous containing lipids include stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Lipids such as lysophosphatidylcholine and lysophosphatidylethanolamine may be used in some instances. Noncationic lipids also include polyethylene glycol-based polymers such as PEG 2000, PEG 5000 and polyethylene glycol conjugated to phospholipids or to ceramides (referred to as PEG-Cer).

In some instances, modified forms of lipids may be used including forms modified with detectable labels such as fluorophores. In some instances, the lipid is a lipid analog that emits signal (e.g., a fluorescent signal). Examples include without limitation 1,1'-dioctadecyl-3,3,3',3'-tetramethylindotricarbocyanine iodide (DiR) and 1,1'-dioctadecyl-3,3,3', 3'-tetramethylindodicarbocyanine (DiD).

Preferably, the lipids are biodegradable in order to allow release of encapsulated agent in vivo and/or in vitro. Biodegradable lipids include but are not limited to 1,2-dioleoyl-sn-glycero-3-phosphocholine (dioleoyl-phosphocholine, DOPC), anionic 1,2-di-(9Z-octadecenoyl)-sn-glycero-3-phospho-(1'-rac-glycerol) (dioleoyl-phosphoglycerol, DOPG), and 1,2-distearoyl-sn-glycero-3-phosphoethanolamine(distearoyl-phosphoethanolamine, DSPE). Non-lipid membrane components such as cholesterol may also be incorporated.

Functionalized Lipids or Bilayer Components

At least one component of the lipid bilayer must be functionalized (or reactive). As used herein, a functionalized component is a component that comprises a reactive group that can be used to crosslink adjacent bilayers of the multilamellar vesicle. The bilayer component may be modified to comprise the reactive group.

One or more of the lipids used in the synthesis of the vesicles may be functionalized lipids. As used herein, a functionalized lipid is a lipid having a reactive group that can be used to crosslink adjacent bilayers of the multilamellar vesicle. In some embodiments, the reactive group is one that will react with a crosslinker (or other moiety) to form crosslinks between such functionalized lipids (and thus between lipid bilayers in the vesicle). The reactive group may be located anywhere on the lipid that allows it to contact a crosslinker and be crosslinked to another lipid in an adjacent apposed bilayer. In some embodiments, it is in the head group of the lipid, including for example a phospholipid. An example of a reactive group is a maleimide group. Maleimide groups may be crosslinked to each other in the presence of dithiol crosslinkers such as but not limited to dithiolthrietol (DTT). An example of a functionalized lipid is 1,2-dioleoyl-sn-glycero-3-phosphoethanolamine-N-[4-(p-maleimidophenyl) butyramide, referred to herein as MPB. The Examples demonstrate use of this functionalized lipid in the synthesis of vesicles of the invention. Another example of a functionalized lipid is 1,2-distearoyl-sn-glycero-3-phosphoethanolamine-N-[maleimide(polyethylene glycol)2000] (also referred to as maleimide-PEG 2k-PE). Another example of a functionalized lipid is dioleoyl-phosphatidylethanolamine 4-(N-maleimidomethyl)-cyclohexane-1-carboxylate (DOPE-mal).

It is to be understood that the invention contemplates the use of other functionalized lipids, other functionalized lipid bilayer components, other reactive groups, and other crosslinkers. In addition to the maleimide groups, other examples of reactive groups include but are not limited to other thiol reactive groups, amino groups such as primary and secondary amines, carboxyl groups, hydroxyl groups, aldehyde groups, alkyne groups, azide groups, carbonyls, haloacetyl (e.g., iodoacetyl) groups, imidoester groups, N-hydroxysuccinimide esters, sulfhydryl groups, pyridyl disulfide groups, and the like.

Functionalized and non-functionalized lipids are available from a number of commercial sources including Avanti Polar Lipids (Alabaster, Ala.).

It is to be understood that the invention contemplates various ways to link adjacent bilayers in the multilamellar vesicles to each other. In some instances, crosslinkers are used to effect linkage between adjacent bilayers. The invention however is not so limited.

As an example, vesicles may be formed using click chemistry. An exemplary synthesis method uses alkyne-modified lipids and alkyne-azide chemistry, as follows. Alkyne-modified lipids were made by mixing the lipids such as 1,2-dioleoyl-sn-glycero-3-phosphoethanolamine (DOPE, 744 mg, 1 mmol) with N-hydroxysuccinimide ester of propiolic acid (167 mg, 1 mmol) and Et$_3$N (202 mg, 2 mmol) in 5 mL CDCl$_3$. The reaction was monitored by NMR. After 3 hours at room temperature, the reaction was completed. After the organic solution was washed with 5 mL 5% Na$_2$CO$_3$, 1% HCl and brine, dried under Na$_2$SO$_4$ and evaporated, and alkyne-modified DOPE was weighed. 1.26 µmol of lipid film with DOPC and alkyne-DOPE in 1:1 molar ratio was prepared, hydrated, sonicated, and induced to fuse with 10 mM Mg$^{2+}$ as described previously. MLVs with alkyne-functionalized lipids were incubated with 2.5 mM CuSO$_4$, copper wire, and 1.5 mM 1,14-diazido-3,6,9,12-tetraoxatetradecane for 24 hours at room temperature. Particle yield was measured after 3× washes with centrifugation.

Crosslinkers

The crosslinker may be a homobifunctional crosslinker or a heterobifunctional crosslinker, depending upon the nature of reactive groups in the lipid bilayers that are being linked to each other. The terms "crosslinker" and "crosslinking agent" are used interchangeably herein. Homobifunctional crosslinkers have two identical reactive groups. Heterobifunctional crosslinkers have two different reactive groups.

In one instance, adjacent bilayers are crosslinked to each other using the same functionalized lipid (or other bilayer component) and a crosslinker (such as a homobifunctional crosslinker). In another instance, adjacent bilayers are crosslinked to each other using different functionalized lipids (or other bilayer components) and a crosslinker (such as a heterobifunctional crosslinker).

Various types of commercially available crosslinkers are reactive with one or more of the following groups: maleimides, primary amines, secondary amines, sulphydryls, carboxyls, carbonyls and carbohydrates. Examples of amine-specific crosslinkers are bis(sulfosuccinimidyl) suberate, bis[2-(succinimidooxycarbonyloxy)ethyl]sulfone, disuccinimidyl suberate, disuccinimidyl tartarate, dimethyl adipimate.2HCl, dimethyl pimelimidate.2HCl, dimethyl suberimidate.2HCl, and ethylene glycolbis-[succinimidyl-[succinate]]. Crosslinkers reactive with sulfhydryl groups include bismaleimidohexane, 1,4-di-[3'-(2'-pyridyldithio)-propionamido)]butane, 1-[p-azidosalicylamido]-4-[iodoacetamido]butane, and N-[4-(p-azidosalicylamido)butyl]-3'-[2'-pyridyldithio]propionamide. Crosslinkers preferentially reactive with carbohydrates include azidobenzoyl hydrazine. Crosslinkers preferentially reactive with carboxyl groups include 4-[p-azidosalicylamido]butylamine. Dithiol crosslinkers such as dithiolthietol (DTT), 1,4-di-[3'-(2'-pyridyldithio)-propionamido]butane (DPDPB), and in some instances thiol containing polymers such as (PEG)-SH2 can be used to crosslink maleimide reactive groups. The structure of DTT is

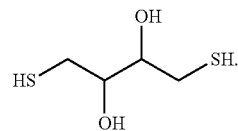

The structure of DPDPB is

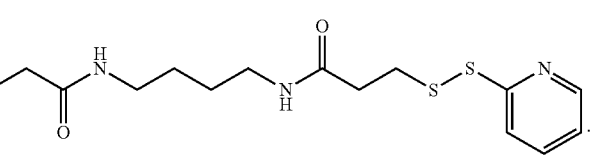

Crosslinkers reactive with alkyne groups include diazides, such as 1,14-Diazido-3,6,9,12-Tetraoxatetradecane, and other groups compatible with "click" chemistry.

Heterobifunctional crosslinkers that react with amines and sulfhydryls include N-succinimidyl-3-[2-pyridyldithio]propionate, succinimidyl[4-iodoacetyl]aminobenzoate, succinimidyl 4-[N-maleimidomethyl]cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional cross-linkers that react with carboxyl and amine groups include 1-ethyl-3-[3-dimethylaminopropyl]-carbodiimide hydrochloride. Heterobifunctional crosslinkers that react with carbohydrates and sulfhydryls include 4-[N-maleimidomethyl]-cyclohexane-1-carboxylhydrazide.2HCl, 4-(4-N-maleimidophenyl)-butyric acid hydrazide.2HCl, and 3-[2-pyridyldithio]propionyl hydrazide. Other crosslinkers are bis-[β-4-azidosalicylamido)ethyl]disulfide and glutaraldehyde.

Crosslinkers are also preferably membrane permeable (or lipid soluble) so that they may diffuse through one or more bilayers of the MLVs to effect crosslinking between various adjacent layers. Any weakly polar/uncharged bifunctional or heterobifunctional small molecule may be an effective membrane permeable crosslinker, particularly if such molecule comprises a reactive group such as but not limited to maleimides, succinimidyl esters, azides, thiols, and the like. Examples of membrane permeable crosslinkers include but are not limited to DTT and 1,4-di-[3'-(2'-pyridyldithio)-propionamido]butane (DPDPB).

PEGylation

The ICMVs may be further modified. As described in the Examples, the ICMV may be conjugated to polyethylene glycol (PEG) on their surface. PEGylation is used clinically to increase the half-life of various agents including STEALTH liposomes. PEGylation may be accomplished by reacting functionalized lipids on the surface of the stabilized MLVs with a complementary functionalized PEG. The lipids are preferably not conjugated to PEG prior to ICMV synthesis, and rather PEG is conjugated to the ICMV external surface post-synthesis or PEG-lipid conjugates are introduced into the external membrane layer of the particles by "post-insertion" processes.

Reactive groups to be used to PEGylate the ICMVs may be the same as those used to crosslink the bilayers, in which case no additional functionalized lipids (or other functionalized components) are required. As an example, if the ICMVs comprise maleimide functionalized lipids, then the functionalized PEG may be thiol-PEG. Alternatively, the reactive groups used to stabilize the vesicles may be different from those used to conjugate PEG to the external surface. Those of ordinary skill in the art will appreciate that other modified versions of PEG may be used depending on the nature of the reactive group in the functionalized lipid (or component) in the lipid bilayer of the vesicles. Suitable reactive groups include without limitation amino groups such as primary and secondary amines, carboxyl groups, sulfhydryl groups, hydroxyl groups, aldehyde groups, azide groups, carbonyls, maleimide groups, haloacetyl (e.g., iodoacetyl) groups, imidoester groups, N-hydroxysuccinimide esters, and pyridyl disulfide groups.

Table 2 illustrates the effect of PEGylation on the ICMV diameter immediately after synthesis and after 7 days in PBS. Immediately after synthesis, the PEGylated ICMVs have a slightly larger diameter than non-PEGylated ICMVs (e.g., 272+/−39 nm for the PEGylated ICMVs versus 234+/−45 nm for the non-PEGylated in one experiment).

Various tests may be performed on the resultant stabilized vesicles in order to determine, inter alia, size and surface charge (e.g., by dynamic light scattering), fraction of lipids on their external surface (e.g., by lamellarity assay), amount of agent incorporated therein or therethrough (e.g., by FACS), and the like. Other tests that may be performed on the vesicles include confocal microscopy and cryo-tunneling electron microscopy (TEM).

The following Tables provide the results of various tests performed on the stabilized vesicles.

TABLE 1A

ICMV yield with varying synthesis conditions.

| Yield % | Lipid composition | Buffer | Cation | DTT | Incubation |
|---|---|---|---|---|---|
| 40 | DOPC/G/MPB (40:10:50) | 10 mM BTP pH 7.0 | 10 mM MgCl2 | 1.5 mM | 2 hr |
| 45 | DOPC/G/MPB (40:10:50) | 10 mM BTP pH 7.0 | 10 mM CaCl2 | 1.5 mM | 2 hr |
| 0 | DOPC/G/MPB (40:10:50) | 10 mM BTP pH 7.0 | 10 mM MgCl2 | | 2 hr |
| 5 | DOPC/G/MPB (40:10:50) | 10 mM BTP pH 7.0 | | 15 mM | 2 hr |
| 5 | DOPC/G/MPB (40:10:50) | 10 mM BTP pH 7.0 | | 1.5 mM | 2 hr |
| 0 | DOPC/G/MPB (40:10:50) | 10 mM BTP pH 7.0 | 20 mM NaCl | 1.5 mM | 2 hr |
| 0 | DOPC/G/MPB (40:10:50) | PBS pH7.0 | 10 mM MgCl2 | 1.5 mM | 2 hr |
| 40 | DOPC/G/MPB (40:10:50) | PBS pH7.0 | 10 mM MgCl2 | 1.5 mM | O/N |
| 45 | DOPC/G/MPB (40:10:50) | 10 mM BTP pH 7.0 | 10 mM MgCl2 | 1.5 mM | 2 hr |
| 15 | DOPC/G/MPB (60:15:25) | 10 mM BTP pH 7.0 | 10 mM MgCl2 | 1.5 mM | 2 hr |
| 0 | DOPC/G/MPB (72:18:10) | 10 mM BTP pH 7.0 | 10 mM MgCl2 | 1.5 mM | 2 hr |
| 0 | DOPC/DOPG (80:20) | 10 mM BTP pH 7.0 | 10 mM MgCl2 | 1.5 mM | 2 hr |
| 0 | DOPC | 10 mM BTP pH 7.0 | 10 mM MgCl2 | 1.5 mM | 2 hr |

TABLE 1B

ICMV yield with varying synthesis conditions.

| Entry | Lipid composition (molar ratio)[a] | Cation[b] | Crosslinker[c] | Yield[d] |
|---|---|---|---|---|
| 1 | DOPC/DOPG/MPB (40:10:50) | MgCl$_2$ | DTT | 45 |
| 2 | DOPC/DOPG/MPB (40:10:50) | CaCl$_2$ | DTT | 50 |
| 3 | DOPC/DOPG/MPB (40:10:50) | 20 mM NaCl | DTT | 0 |
| 4 | DOPC/DOPG/MPB (40:10:50) | MgCl$_2$ | — | 0 |
| 5 | DOPC/DOPG/MPB (40:10:50) | — | DTT | 7 |
| 6 | DOPC/DOPG/MPB (40:10:50) | — | 15 mM DTT | 4 |
| 7 | DOPC/DOPG/MPB (60:15:25) | MgCl$_2$ | DTT | 15 |
| 8 | DOPC/DOPG/MPB (72:18:10) | MgCl$_2$ | DTT | 0 |
| 9 | DOPC/DOPG (80:20) | MgCl$_2$ | DTT | 0 |
| 10 | DOPC/DOPG/MPB (40:10:50) | MgCl$_2$ | DPDPB[e] | 48 |
| 11 | DOPC/DOPG/MPB (40:10:50) | MgCl$_2$ | (PEG)-SH$_2$[f] | 3 |

[a] hydrated with 10 mM bis-tris propane at pH 7.0;
[b] at 10 mM unless noted otherwise;
[c] at 1.5 mM unless noted otherwise
[d] percentage of lipid mass recovered after synthesis and centrifugation at 14,000 × g for 4 min
[e] 1,4-Di[3'-(2'pyridyldithio)-propionamido]butane (MW 482);
[f] MW 2000

TABLE 2

Vesicle characterization at each step in synthesis process.

| Synthesis step (FIG. 2A) | Samples | Hydrodynamic diameter[a] (nm) | Polydispersity index | Zeta potential (mV) | Diameter after 7 days in 4°C (nm) | Diameter after lyophilization (nm) | Diameter after lyophilization with 3% sucrose (nm) |
|---|---|---|---|---|---|---|---|
| (i) | Liposomes | 192 ± 39 | 0.385 ± 0.11 | −0.141 ± 0.44 | N/A | N/A | N/A |
| (ii) | $Mg^{2+}$-fused MLVs | 220 ± 26 | 0.217 ± 0.053 | −0.151 ± 0.67 | N/A | N/A | N/A |
| (iii) | ICMVs | 244 ± 17 | 0.223 ± 0.11 | −0.415 ± 0.33 | 1610 ± 570 | N/A | N/A |
| (iv) | PEGylated ICMVs | 263 ± 20 | 0.183 ± 0.025 | −2.34 ± 0.44 | 265 ± 27 | 2960 ± 1800 | 269 ± 41 |

[a]measured by dynamic light scattering (DLS)
[b]Fraction of lipid exposed on the external surface of vesicles decreased after interbilayer-crosslinked as measured by lamellarity assay (see Lutsiak et al. *Pharm Res* 19, 1480-1487 (2002))
*all values with mean ± SD Agents The invention contemplates the delivery, including in some instances sustained delivery, of agents to regions, tissues or cells in vivo or in vitro using the stabilized lipid vesicles, including the ICMV, of the invention. As used herein, an agent is any atom or molecule or compound that can be used to provide benefit to a subject (including without limitation prophylactic or therapeutic benefit) or that can be used for diagnosis and/or detection (for example, imaging) in vivo or that has use in in vitro applications.

Any agent may be delivered using the compositions (e.g., the stabilized MLVs such as the ICMVs, and compositions thereof including pharmaceutical compositions thereof) and methods of the invention provided that it can be encapsulated into (including throughout) or otherwise carried on (e.g., attached to the surface of) the stabilized MLVs such as the ICMVs provided herein. For example, the agent must be able to withstand the synthesis and optionally storage process for these vesicles. The vesicles may be synthesized and stored in, for example, a lyophilized form, preferably with a sucrose based excipient. The agents, if incorporated into the vesicles during synthesis, should be stable during such storage procedures and times.

The agent may be without limitation a protein, a polypeptide, a peptide, a nucleic acid, a small molecule (e.g., chemical, whether organic or inorganic) drug, a virus-like particle, a steroid, a proteoglycan, a lipid, a carbohydrate, and analogs, derivatives, mixtures, fusions, combinations or conjugates thereof. The agent may be a prodrug that is metabolized and thus converted in vivo to its active (and/or stable) form.

The agents may be naturally occurring or non-naturally occurring. Naturally occurring agents include those capable of being synthesized by the subjects to whom the vesicles are administered. Non-naturally occurring are those that do not exist in nature normally, whether produced by plant, animal, microbe or other living organism.

In accordance with the invention, the agents may be cysteine-modified, similar to the cysteine-modified antigens discussed herein, particularly if surface presentation of the agent is desired. Accordingly, cysteine-modified agents, as defined herein, are agents that have been modified through the addition of one or more cysteine residues at or near their termini. If the agent is a protein or peptide, one or more cysteine residues may be added to the amino and/or carboxy terminus such that after modification one or more cysteines are present within 10 residues of the amino terminus and/or within 10 residues of the carboxy terminus.

One class of agents is peptide-based agents such as (single or multi-chain) proteins and peptides. Examples include antibodies, single chain antibodies, antibody fragments, enzymes, co-factors, receptors, ligands, transcription factors and other regulatory factors, some antigens (as discussed below), cytokines, chemokines, and the like. These peptide-based agents may or may not be naturally occurring but they are capable of being synthesized within the subject, for example, through the use of genetically engineered cells.

Another class of agents that can be delivered using the vesicles of the invention includes those agents that are not peptide-based. Examples include chemical compounds that are non-naturally occurring, or chemical compounds that are not naturally synthesized by mammalian (and in particular human) cells.

A variety of agents that are currently used for therapeutic or diagnostic purposes can be delivered according to the invention and these include without limitation imaging agents, immunomodulatory agents such as immunostimulatory agents and immunoinhibitory agents, antigens, adjuvants, cytokines, chemokines, anti-cancer agents, anti-infective agents, nucleic acids, antibodies or fragments thereof, fusion proteins such as cytokine-antibody fusion proteins, Fc-fusion proteins, and the like.

Imaging Agents.

As used herein, an imaging agent is an agent that emits signal directly or indirectly thereby allowing its detection in vivo. Imaging agents such as contrast agents and radioactive agents that can be detected using medical imaging techniques such as nuclear medicine scans, magnetic resonance imaging (MRI), positron-emission tomography (PET), and in vivo fluorescence imaging. Examples of such imaging agents are provided in published U.S. patent application US 2011-0229529, and such examples are incorporated by reference herein. In other embodiments, the agent to be delivered is conjugated, or fused to, or mixed or combined with an imaging agent.

Immunostimulatory Agents.

As used herein, an immunostimulatory agent is an agent that stimulates an immune response (including enhancing a pre-existing immune response) in a subject to whom it is administered, whether alone or in combination with another agent. Examples include antigens, adjuvants (e.g., TLR ligands such as imiquimod and resiquimod, imidazoquinolines, nucleic acids comprising an unmethylated CpG dinucleotide, monophosphoryl lipid A (MPLA) or other lipopolysaccharide derivatives, single-stranded or double-stranded RNA, flagellin, muramyl dipeptide), cytokines including interleukins (e.g., IL-2, IL-7, IL-15 (or superagonist/mutant forms of these cytokines), IL-12, IFN-gamma, IFN-alpha, GM-CSF, FLT3-ligand, etc.), immunostimulatory antibodies (e.g., anti-CTLA-4, anti-CD28, anti-CD3, or single chain/antibody fragments of these molecules), and the like.

Antigens.

The antigen may be without limitation a cancer antigen, a self or autoimmune antigen, a microbial antigen, an allergen, or an environmental antigen. The antigen may be peptide, lipid, or carbohydrate in nature, but it is not so limited.

Cancer Antigens.

A cancer antigen is an antigen that is expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell. The cancer antigen may be MART-1/Melan-A, gp100, adenosine deaminase-binding protein (ADAbp), FAP, cyclophilin b, colorectal associated antigen (CRC)—C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05). The cancer antigen may be selected from the group consisting of GAGE-1, GAGE-2, GAGE-3, GAGE-4, GAGE-5, GAGE-6, GAGE-7, GAGE-8, GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100$^{Pmel117}$, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, and c-erbB-2.

Microbial Antigens.

Microbial antigens are antigens derived from microbial species such as without limitation bacterial, viral, fungal, parasitic and mycobacterial species. As such, microbial antigens include bacterial antigens, viral antigens, fungal antigens, parasitic antigens, and mycobacterial antigens. Examples of bacterial, viral, fungal, parasitic and mycobacterial species are provided herein. The microbial antigen may be part of a microbial species or it may be the entire microbe.

Allergens.

An allergen is an agent that can induce an allergic or asthmatic response in a subject. Allergens include without limitation pollens, insect venoms, animal dander dust, fungal spores and drugs (e.g. penicillin). Examples of natural, animal and plant allergens include but are not limited to proteins specific to the following genera: *Canine* (*Canis familiaris*); *Dermatophagoides* (e.g. *Dermatophagoides farinae*); *Felis* (*Felis domesticus*); *Ambrosia* (*Ambrosia artemiisfolia*; *Lolium* (e.g. *Lolium perenne* or *Lolium multiflorum*); *Cryptomeria* (*Cryptomeria japonica*); *Alternaria* (*Alternaria alternata*); *Alder*; *Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens*, *Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

Adjuvants.

The adjuvant may be without limitation alum (e.g., aluminum hydroxide, aluminum phosphate); saponins purified from the bark of the *Q. saponaria* tree such as QS21 (a glycolipid that elutes in the 21st peak with HPLC fractionation; Antigenics, Inc., Worcester, Mass.); poly[di(carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-, AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic)

Adjuvants may be TLR ligands. Adjuvants that act through TLR3 include without limitation double-stranded RNA. Adjuvants that act through TLR4 include without limitation derivatives of lipopolysaccharides such as monophosphoryl lipid A (MPLA; Ribi ImmunoChem Research, Inc., Hamilton, Mont.) and muramyl dipeptide (MDP; Ribi) andthreonyl-muramyl dipeptide (t-MDP; Ribi); OM-174 (a glucosamine disaccharide related to lipid A; OM Pharma SA, Meyrin, Switzerland). Adjuvants that act through TLR5 include without limitation flagellin. Adjuvants that act through TLR7 and/or TLR8 include single-stranded RNA, oligoribonucleotides (ORN), synthetic low molecular weight compounds such as imidazoquinolinamines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

Immunoinhibitory Agents.

As used herein, an immunoinhibitory agent is an agent that inhibits an immune response in a subject to whom it is administered, whether alone or in combination with another agent. Examples include steroids, retinoic acid, dexamethasone, cyclophosphamide, anti-CD3 antibody or antibody fragment, and other immunosuppressants.

Anti-Cancer Agents.

As used herein, an anti-cancer agent is an agent that at least partially inhibits the development or progression of a cancer, including inhibiting in whole or in part symptoms associated with the cancer even if only for the short term. Several anti-cancer agents can be categorized as DNA damaging agents and these include topoisomerase inhibitors, DNA alkylating agents, DNA strand break inducing agents, anti-microtubule agents, anti-metabolic agents, anthracyclines, vinca alkaloids. or epipodophyllotoxins. Examples of each of the foregoing classes of anti-cancer agents, as well as others, are provided in published U.S. patent application US 2011-0229529, and such examples are incorporated by reference herein.

The anti-cancer agent may be an enzyme inhibitor including without limitation tyrosine kinase inhibitor, a CDK inhibitor, a MAP kinase inhibitor, or an EGFR inhibitor. Examples of each of these classes are provided in published U.S. patent application US 2011-0229529, and such examples are incorporated by reference herein.

The anti-cancer agent may be a VEGF inhibitor including without limitation bevacizumab (AVASTIN), ranibizumab (LUCENTIS), pegaptanib (MACUGEN), sorafenib, sunitinib (SUTENT), vatalanib, ZD-6474 (ZACTIMA), anecortave (RETAANE), squalamine lactate, and semaphorin.

The anti-cancer agent may be an antibody or an antibody fragment including without limitation an antibody or an antibody fragment including but not limited to bevacizumab (AVASTIN), trastuzumab (HERCEPTIN), alemtuzumab (CAMPATH, indicated for B cell chronic lymphocytic leukemia,), gemtuzumab (MYLOTARG, hP67.6, anti-CD33, indicated for leukemia such as acute myeloid leukemia), rituximab (RITUXAN), tositumomab (BEXXAR, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX, indicated for ovarian cancer), edrecolomab (PANOREX), daclizumab (ZENAPAX), palivizumab (SYNAGIS, indicated for respiratory conditions such as RSV infection), ibritumomab tiuxetan (ZEVALIN, indicated for Non-Hodgkin's lymphoma), cetuximab (ERBITUX), MDX-447, MDX-22, MDX-220 (anti-TAG-72), IOR-C5, IOR-T6 (anti-CD1), IOR EGF/R3, celogovab (ONCOSCINT OV103), epratuzumab (LYMPHOCIDE), pemtumomab (THERAGYN), and Gliomab-H (indicated for brain cancer, melanoma).

Hematopoietic Differentiating Agents.

The agent may be one that stimulates the differentiation of hematopoietic progenitor cells towards one or more lineages. Examples include without limitation IL-3, G-CSF, GM-CSF, M-CSF, thrombopoeitin, erythropoietin, Wnt5A, Wnt11A, and the like.

Hematopoietic Self-Renewing Agents.

The agent may be one that stimulates the self-renewal of hematopoietic progenitor cells. Examples are provided in published U.S. patent application US 2011-0229529, and such examples are incorporated by reference herein.

Anti-Infective Agents.

The agent may be an anti-infective agent including without limitation an anti-bacterial agent, an anti-viral agent, an anti-parasitic agent, an anti-fungal agent, and an anti-mycobacterial agent.

Anti-bacterial agents may be without limitation β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, sulfonamides and trimethoprim, or quinolines.

Examples of other anti-bacterials are provided in published U.S. patent application US 2011-0229529, and such examples are incorporated by reference herein.

Anti-viral agents may be without limitation amantidine and rimantadine, ribivarin, acyclovir, vidarabine, trifluorothymidine, ganciclovir, zidovudine, retinovir, and interferons. Examples of anti-viral agents are provided in published U.S. patent application US 2011-0229529, and such examples are incorporated by reference herein Anti-fungal agents may be without limitation imidazoles and triazoles, polyene macrolide antibiotics, griseofulvin, amphotericin B, and flucytosine.

Examples of antiparasites are provided in published U.S. patent application US 2011-0229529, and such examples are incorporated by reference herein.

Examples of other anti-infective agents are provided in published U.S. patent application US 2011-0229529, and such examples are incorporated by reference herein.

Nucleic Acid Agents.

Nucleic acids that can be delivered to a subject according to the invention include naturally or non-naturally occurring DNA (including cDNA, genomic DNA, nuclear DNA, mitochondrial DNA), RNA (including mRNA, rRNA, tRNA), oligonucleotides, a triple-helix forming molecule, immunostimulatory nucleic acids such as those described in U.S. Pat. No. 6,194,388 (the teachings of which relating to immunostimulatory CpG nucleic acids are incorporated herein by reference), small interfering RNA (siRNA) or microRNAs (miRNA) used to modulate gene expression, antisense oligonucleotides used to modulate gene expression, aptamers, ribozymes, a gene or gene fragment, a regulatory sequence, including analogs, derivatives, and combinations thereof. These nucleic acids may be administered neat or complexed to another entity, for example in order to facilitate their binding to and/or uptake by target tissues and/or cells.

Anti-Inflammatory Agents.

Anti-inflammatory agents are agents that reduce or eliminate inflammation. Examples of anti-inflammatory agents are provided in published U.S. patent application US 2011-0229529, and such examples are incorporated by reference herein.

Other Agents.

The agent may be any one of those agents provided in published U.S. patent application US 2011-0229529, and such agents are incorporated by reference herein.

In still other embodiments, an agent of the invention, including an antigen of the invention, may be linked to an ICMV using click chemistry to an azide on a peptide or a protein, or carbodiimide coupling to free amines on peptides or proteins to carboxylates on the ICMV.

Subjects

The invention can be practiced in virtually any subject type that is likely to benefit from delivery of agents as contemplated herein. Human subjects are preferred subjects in some embodiments of the invention. Subjects also include animals such as household pets (e.g., dogs, cats, rabbits, ferrets, etc.), livestock or farm animals (e.g., cows, pigs, sheep, chickens and other poultry), horses such as thoroughbred horses, laboratory animals (e.g., mice, rats, rabbits, etc.), and the like. Subjects also include fish and other aquatic species.

The subjects to whom the agents are delivered may be normal subjects. Alternatively they may have or may be at risk of developing a condition that can be diagnosed or that can benefit from delivery of one or more particular agents.

Such conditions include cancer (e.g., solid tumor cancers or non-solid cancer such as leukemias), infections (including infections localized to particular regions or tissues in the body), autoimmune disorders, allergies or allergic conditions, asthma, transplant rejection, and the like.

Tests for diagnosing various of the conditions embraced by the invention are known in the art and will be familiar to the ordinary medical practitioner. These laboratory tests include without limitation microscopic analyses, cultivation dependent tests (such as cultures), and nucleic acid detection tests. These include wet mounts, stain-enhanced microscopy, immune microscopy (e.g., FISH), hybridization microscopy, particle agglutination, enzyme-linked immunosorbent assays, urine screening tests, DNA probe hybridization, serologic tests, etc. The medical practitioner will generally also take a full history and conduct a complete physical examination in addition to running the laboratory tests listed above.

A subject having a cancer is a subject that has detectable cancer cells. A subject at risk of developing a cancer is a subject that has a higher than normal probability of developing cancer. These subjects include, for instance, subjects having a genetic abnormality that has been demonstrated to be associated with a higher likelihood of developing a cancer, subjects having a familial disposition to cancer, subjects exposed to cancer causing agents (i.e., carcinogens) such as tobacco, asbestos, or other chemical toxins, and subjects previously treated for cancer and in apparent remission.

Subjects having an infection are those that exhibit symptoms thereof including without limitation fever, chills, myalgia, photophobia, pharyngitis, acute lymphadenopathy, splenomegaly, gastrointestinal upset, leukocytosis or leukopenia, and/or those in whom infectious pathogens or byproducts thereof can be detected.

A subject at risk of developing an infection is one that is at risk of exposure to an infectious pathogen. Such subjects include those that live in an area where such pathogens are known to exist and where such infections are common. These subjects also include those that engage in high risk activities such as sharing of needles, engaging in unprotected sexual activity, routine contact with infected samples of subjects (e.g., medical practitioners), people who have undergone surgery, including but not limited to abdominal surgery, etc.

The subject may have or may be at risk of developing an infection such as a bacterial infection, a viral infection, a fungal infection, a parasitic infection or a mycobacterial infection. In these embodiments, the vesicles may comprise an anti-microbial agent such as an anti-bacterial agent, an anti-viral agent, an anti-fungal agent, an anti-parasitic agent, or an anti-mycobacterial agent and the cell carriers (e.g., the T cells) may be genetically engineered to produce another agent useful in stimulating an immune response against the infection, or potentially treating the infection.

Cancer

The invention contemplates administration of agents to subjects having or at risk of developing a cancer including for example a solid tumor cancer, using the vesicles of the invention. The agents may be anti-cancer agents, including chemotherapeutics, antibody based therapeutics, hormone based therapeutics, and enzyme inhibitory agents, and/or they may be immunostimulatory agents such as antigens (e.g., cancer antigens) and/or adjuvants, and/or they may be diagnostic agents (e.g., imaging agents), or any of the other agents described herein. The invention contemplates that the vesicles of the invention are able to deliver higher quantities of these agents, alone or in combination, to these subjects, and/or to allow prolonged exposure of the subject to these agents via a slow steady release profile.

The cancer may be carcinoma, sarcoma or melanoma. Carcinomas include without limitation to basal cell carcinoma, biliary tract cancer, bladder cancer, breast cancer, cervical cancer, choriocarcinoma, CNS cancer, colon and rectum cancer, kidney or renal cell cancer, larynx cancer, liver cancer, small cell lung cancer, non-small cell lung cancer (NSCLC, including adenocarcinoma, giant (or oat) cell carcinoma, and squamous cell carcinoma), oral cavity cancer, ovarian cancer, pancreatic cancer, prostate cancer, skin cancer (including basal cell cancer and squamous cell cancer), stomach cancer, testicular cancer, thyroid cancer, uterine cancer, rectal cancer, cancer of the respiratory system, and cancer of the urinary system.

Sarcomas are rare mesenchymal neoplasms that arise in bone (osteosarcomas) and soft tissues (fibrosarcomas). Sarcomas include without limitation liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal (i.e., not bone) Ewing's sarcoma, and primitive neuroectodermal tumor), synovial sarcoma, angiosarcomas, hemangiosarcomas, lymphangiosarcomas, Kaposi's sarcoma, hemangioendothelioma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) (also known as GI stromal sarcoma), and chondrosarcoma.

Melanomas are tumors arising from the melanocytic system of the skin and other organs. Examples of melanoma include without limitation lentigo maligna melanoma, superficial spreading melanoma, nodular melanoma, and acral lentiginous melanoma.

The cancer may be a solid tumor lymphoma. Examples include Hodgkin's lymphoma, Non-Hodgkin's lymphoma, and B cell lymphoma.

The cancer may be without limitation bone cancer, brain cancer, breast cancer, colorectal cancer, connective tissue cancer, cancer of the digestive system, endometrial cancer, esophageal cancer, eye cancer, cancer of the head and neck, gastric cancer, intra-epithelial neoplasm, melanoma neuroblastoma, Non-Hodgkin's lymphoma, non-small cell lung cancer, prostate cancer, retinoblastoma, or rhabdomyosarcoma.

Infection

The invention contemplates administration of agents to subjects having or at risk of developing an infection such as a bacterial infection, a viral infection, a fungal infection, a parasitic infection or a mycobacterial infection, using the vesicles of the invention. The agents may be anti-infective agents including anti-bacterial agents, anti-viral agents, anti-fungal agents, anti-parasitic agents, and anti-mycobacterial agents), immunostimulatory agents such as antigens (e.g., microbial antigens such as bacterial antigens, viral antigens, fungal antigens, parasitic antigens, and mycobacterial antigens) and/or adjuvants, diagnostic agents (e.g., imaging agents), or any of the other agents described herein. The invention contemplates that the vesicles of the invention are able to deliver higher quantities of these agents, alone or in combination, to these subjects, and/or to allow prolonged exposure of the subject to these agents via a slow steady release profile.

The bacterial infection may be without limitation an *E. coli* infection, a *Staphylococcal* infection, a Streptococcal infection, a *Pseudomonas* infection, *Clostridium difficile* infection, *Legionella* infection, *Pneumococcus* infection, *Haemophilus* infection, *Klebsiella* infection, *Enterobacter* infection, *Citro-*

*bacter* infection, *Neisseria* infection, *Shigella* infection, *Salmonella* infection, *Listeria* infection, *Pasteurella* infection, *Streptobacillus* infection, *Spirillum* infection, *Treponema* infection, *Actinomyces* infection, *Borrelia* infection, *Corynebacterium* infection, *Nocardia* infection, *Gardnerella* infection, *Campylobacter* infection, *Spirochaeta* infection, *Proteus* infection, *Bacteriodes* infection, *H. pylori* infection, or anthrax infection.

The mycobacterial infection may be without limitation tuberculosis or leprosy respectively caused by the *M. tuberculosis* and *M. leprae* species.

The viral infection may be without limitation a Herpes simplex virus 1 infection, a Herpes simplex virus 2 infection, cytomegalovirus infection, hepatitis A virus infection, hepatitis B virus infection, hepatitis C virus infection, human papilloma virus infection, Epstein Barr virus infection, rotavirus infection, adenovirus infection, influenza virus infection, influenza A virus infection, H1N1 (swine flu) infection, respiratory syncytial virus infection, varicella-zoster virus infections, small pox infection, monkey pox infection, SARS infection or avian flu infection.

The fungal infection may be without limitation candidiasis, ringworm, histoplasmosis, blastomycosis, paracoccidioidomycosis, crytococcosis, aspergillosis, *chromomycosis*, mycetoma infections, pseudallescheriasis, or tinea versicolor infection.

The parasite infection may be without limitation amebiasis, *Trypanosoma cruzi* infection, Fascioliasis, Leishmaniasis, *Plasmodium* infections, Onchocerciasis, Paragonimiasis, *Trypanosoma brucei* infection, *Pneumocystis* infection, *Trichomonas vaginalis* infection, *Taenia* infection, *Hymenolepsis* infection, *Echinococcus* infections, Schistosomiasis, neurocysticercosis, *Necator americanus* infection, or *Trichuris trichuria* infection.

Allergy and Asthma

The invention contemplates administration of agents to subjects having or at risk of developing an allergy or asthma. The agents may be allergens, immunostimulatory agents including agents that stimulate a Th1 response, immunoinhibitory or immunosuppressant agents including agents that inhibit a Th2 response, anti-inflammatory agents, leukotriene antagonists, IL-4 muteins, soluble IL-4 receptors, anti-IL-4 antibodies, IL-4 antagonists, anti-IL-5 antibodies, soluble IL-13 receptor-Fc fusion proteins, anti-IL-9 antibodies, CCR3 antagonists, CCR5 antagonists, VLA-4 inhibitors, and other downregulators of IgE such as but not limited to anti-IgE, cytokines such as Th1 cytokines such as IL-12 and IFN-gamma, steroids including corticosteroids such as prednisolone, and/or they may be diagnostic agents (e.g., imaging agents), or any of the other agents described herein. The invention contemplates that the vesicles of the invention are able to deliver higher quantities of these agents, alone or in combination, to these subjects, and/or to allow prolonged exposure of the subject to these agents via a slow steady release profile.

An allergy is an acquired hypersensitivity to an allergen. Allergic conditions include but are not limited to eczema, allergic rhinitis or coryza, hay fever, bronchial asthma, urticaria (hives) and food allergies, and other atopic conditions. Allergies are generally caused by IgE antibody generation against harmless allergens. Asthma is a disorder of the respiratory system characterized by inflammation, narrowing of the airways and increased reactivity of the airways to inhaled agents. Asthma is frequently, although not exclusively, associated with atopic or allergic symptoms.

Autoimmune Disease

The invention contemplates administration of agents to subjects having or at risk of developing an autoimmune disease or disorder. The agents may be immunoinhibitory or immunosuppressant agents including those that inhibit a Th1 response, immunostimulatory agents that stimulate a Th2 response, cytokines such as IL-4, IL-5 and IL-10, anti-inflammatory agents, and/or they may be diagnostic agents (e.g., imaging agents), or any of the other agents described herein. The invention contemplates that the vesicles of the invention are able to deliver higher quantities of these agents, alone or in combination, to these subjects, and/or to allow prolonged exposure of the subject to these agents via a slow steady release profile.

Autoimmune disease is a class of diseases in which a subject's own antibodies react with host tissue or in which immune effector T cells are autoreactive to endogenous self peptides and cause destruction of tissue. Thus an immune response is mounted against a subject's own antigens, referred to as self antigens. Autoimmune diseases are generally considered to be Th1 biased. As a result, induction of a Th2 immune response or Th2 like cytokines can be beneficial.

Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus.

Transplant Therapy

The invention contemplates administration of agents to subjects undergoing a cell or organ transplant. The agents may be immunoinhibitory or immunosuppressant agents, anti-inflammatory agents, and/or they may be diagnostic agents (e.g., imaging agents), or any of the other agents described herein. The invention contemplates that the vesicles of the invention are able to deliver higher quantities of these agents, alone or in combination, to these subjects, and/or to allow prolonged exposure of the subject to these agents via a slow steady release profile.

The compositions and methods provided herein may also be used to modulate immune responses following transplant therapy. Transplant success is often limited by rejection of the transplanted tissue by the body's immune system. As a result, transplant recipients are usually immunosuppressed for extended periods of time in order to allow the transplanted tissue to survive. The invention contemplates delivery of immunomodulators, and particularly immunoinhibitory agents, to transplant sites in order to minimize transplant rejection. Thus, the invention contemplates administration to subjects that are going to undergo, are undergoing, or have undergone a transplant.

The foregoing lists are not intended to be exhaustive but rather exemplary. Those of ordinary skill in the art will identify other examples of each condition type that are amenable to prevention and treatment using the methods of the invention.

Effective Amounts, Regimens, Formulations

The agents are administered in the form of stabilized MLVs and in effective amounts. An effective amount is a dosage of the agent sufficient to provide a medically desirable result. The effective amount will vary with the desired outcome, the particular condition being treated or prevented, the age and physical condition of the subject being treated, the severity of the condition, the duration of the treatment, the nature of the concurrent or combination therapy (if any), the specific route of administration and like factors within the knowledge and expertise of the health practitioner. It is preferred generally that a maximum dose be used, that is, the highest safe dose according to sound medical judgment.

For example, if the subject has a tumor, an effective amount may be that amount that reduces the tumor volume or load (as for example determined by imaging the tumor). Effective amounts may also be assessed by the presence and/or frequency of cancer cells in the blood or other body fluid or tissue (e.g., a biopsy). If the tumor is impacting the normal functioning of a tissue or organ, then the effective amount may be assessed by measuring the normal functioning of the tissue or organ.

In some instances the effective amount is the amount required to lessen or eliminate one or more, and preferably all, symptoms. For example, in a subject having an allergy or experiencing an asthmatic attack, an effective amount of an agent may be that amount that lessens or eliminates the symptoms associated with the allergy or the asthmatic attack. They may include sneezing, hives, nasal congestion, and labored breathing. Similarly, in a subject having an infection, an effective amount of an agent may be that amount that lessens or eliminate the symptoms associated with the infection. These may include fever and malaise. If the agent is a diagnostic agent, an effective amount may be an amount that allows visualization of the body region or cells of interest. If the agent is an antigen, the effective amount may be that amount that triggers an immune response against the antigen and preferably provides short and even more preferably long term protection against the pathogen from which the antigen derives. It will be understood that in some instances the invention contemplates single administration of an agent and in some instances the invention contemplates multiple administrations of an agent. As an example, an antigen may be administered in a prime dose and a boost dose, although in some instances the invention provides sufficient delivery of the antigen, and optionally an adjuvant, that no boost dose is required.

The invention provides pharmaceutical compositions. Pharmaceutical compositions are sterile compositions that comprise the vesicles of the invention and preferably agent(s), preferably in a pharmaceutically-acceptable carrier. The term "pharmaceutically-acceptable carrier" means one or more compatible solid or liquid filler, diluents or encapsulating substances which are suitable for administration to a human or other subject contemplated by the invention.

The term "carrier" denotes an organic or inorganic ingredient, natural or synthetic, with which vesicles and preferably agent(s) are combined to facilitate administration. The components of the pharmaceutical compositions are commingled in a manner that precludes interaction that would substantially impair their desired pharmaceutical efficiency.

Suitable buffering agents include acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); and parabens (0.01-0.25% W/V).

Unless otherwise stated herein, a variety of administration routes are available. The particular mode selected will depend, of course, upon the particular active agent selected, the particular condition being treated and the dosage required for therapeutic efficacy. The methods provided, generally speaking, may be practiced using any mode of administration that is medically acceptable, meaning any mode that produces effective levels of a desired response without causing clinically unacceptable adverse effects. One mode of administration is a parenteral route. The term "parenteral" includes subcutaneous injections, intravenous, intramuscular, intraperitoneal, intra sternal injection or infusion techniques. Other modes of administration include oral, mucosal, rectal, vaginal, sublingual, intranasal, intratracheal, inhalation, ocular, transdermal, etc.

For oral administration, the compounds can be formulated readily by combining the vesicles with pharmaceutically acceptable carriers well known in the art. Such carriers enable formulation as tablets, pills, dragees, capsules, liquids, gels, syrups, slurries, films, suspensions and the like, for oral ingestion by a subject to be treated. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). Optionally the oral formulations may also be formulated in saline or buffers for neutralizing internal acid conditions or may be administered without any carriers.

Pharmaceutical preparations which can be used orally include push-fit capsules made of gelatin, as well as soft, sealed capsules made of gelatin and a plasticizer, such as glycerol or sorbitol. The push-fit capsules can contain the vesicles suspended in suitable liquids, such as aqueous solutions, buffered solutions, fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compositions may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

When it is desirable to deliver the compositions of the invention systemically, they may be formulated for parenteral administration by injection, e.g., by bolus injection or continuous infusion. Formulations for injection may be presented in unit dosage form, e.g., in ampoules or in multi-dose containers. Pharmaceutical parenteral formulations include aqueous solutions of the ingredients. Aqueous injection suspensions may contain substances which increase the viscosity of the suspension, such as sodium carboxymethyl cellulose, sorbitol, or dextran. Alternatively, suspensions of vesicles may be prepared as oil-based suspensions. Suitable lipophilic solvents or vehicles include fatty oils such as sesame oil, or synthetic fatty acid esters, such as ethyl oleate or triglycerides.

Alternatively, the vesicles may be in powder form or lyophilized form for constitution with a suitable vehicle, e.g., sterile pyrogen-free water, before use.

The compositions may also be formulated in rectal or vaginal compositions such as suppositories or retention enemas, e.g., containing conventional suppository bases such as cocoa butter or other glycerides.

In Vitro Use

The invention further contemplates in vitro applications such as cell culturing and tissue engineering, that require or for which it would be more convenient to have a constant source of one or more agents such as but not limited to cell growth factors, and the like.

Kits

The invention further contemplates kits comprising the vesicles of the invention. The vesicles may comprise one or more agents of interest. The kits may further comprise one or more agents of interest to be incorporated into the vesicles. These kits may also include written materials such as instructions for use of the vesicles. The vesicles may be provided in a buffer or in a lyophilized form, preferably with a sucrose-containing excipient.

The invention also contemplates kits comprising the various substrates, reagents and catalysts required for synthesizing the vesicles of the invention. Such kits may include for example lipids such as those described herein, functionalized components of a lipid bilayer such as functionalized lipids, one or more crosslinkers such as membrane permeable crosslinkers, multivalent cations such as divalent cations, and the like. These kits may also include written materials such as instructions for synthesizing the vesicles. The kits may also include the agents of interest.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Figure 5A:
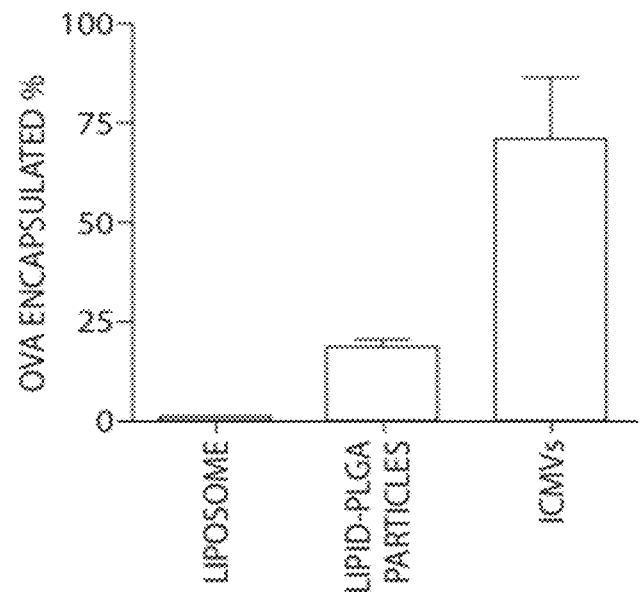
FIGS. 5A-B. Comparison of OVA encapsulation in traditional liposomes, lipid-coated PLGA particles, and ICMVs, showing (A) fraction of OVA encapsulated in particles and (B) the amount of OVA encapsulated per total particle mass.
Figure 5B:
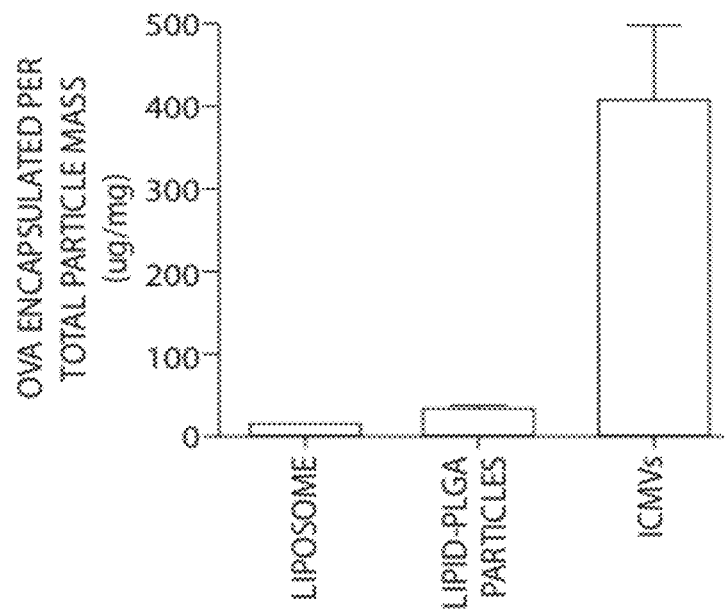
Figure 6A:
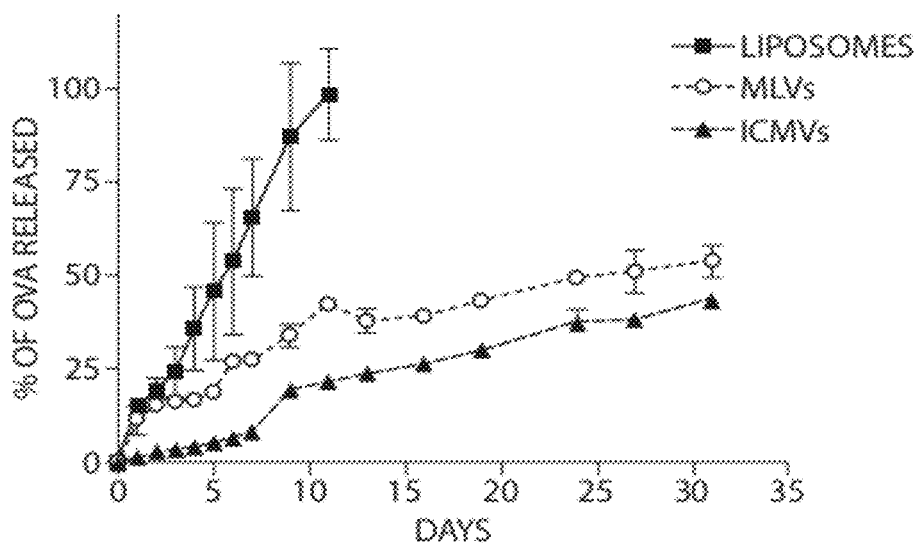
Figure 6B:
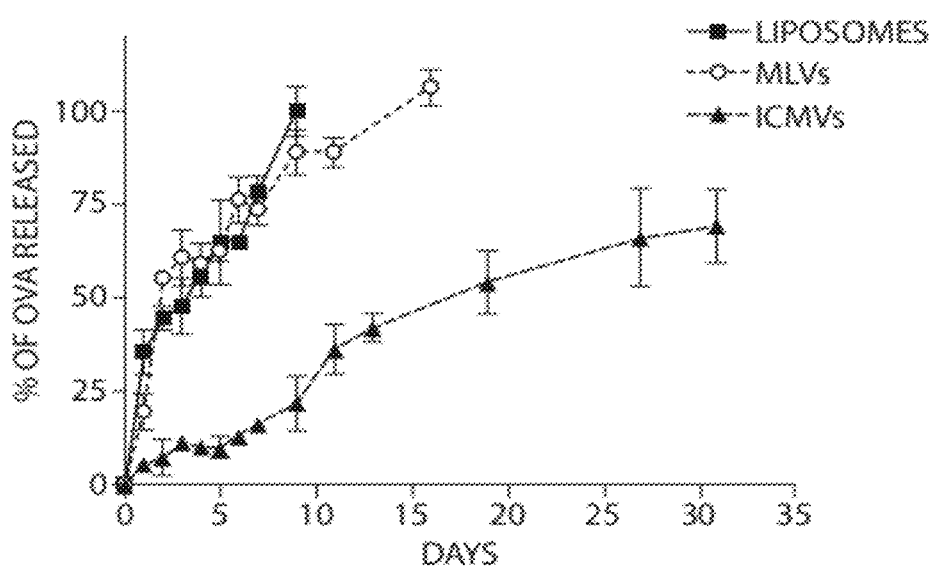

To address limitations in prior art methods, we envisioned the synthesis of lipid particles stabilized by forming crosslinks connecting the headgroups of adjacent lipid layers within multilamellar vesicles (MLVs). Divalent cations are known to induce fusion of liposomes into MLVs. (See Duzgunes et al., J Membrane Biol. 1981; 59:115-125.) We modified this process by introducing maleimide-functionalized lipids (e.g., MPB) into vesicles and crosslinking layers of MPB using dithiol-crosslinkers (e.g., synthesis schematics shown in FIG. 1A). The resulting interbilayer-crosslinked multilamellar lipid vesicles (ICMVs) exhibited attractive features, such as greatly enhanced protein encapsulation efficiency (100-fold relative to simple liposomes, FIG. 5), protein loading per mass of particles (20-fold relative to simple liposomes, FIG. 5), and sustained retention of entrapped cargos in the presence of serum with slow, sustained release kinetics (FIG. 6). The synthesis is carried entirely in aqueous buffers friendly to the entrapment of fragile protein cargos, and generates particles composed only of biodegradable lipids. As a test-bed for biomedical applications of this new class of particles, we examined ICMVs as a delivery vehicle for antigens and adjuvants. Specifically, we used ovalbumin (OVA) as a model antigen and tested co-delivery of toll-like receptor agonists (TLRa) in vivo for vaccine applications.

Materials and Methods

Lipids (DOPC:DOPG:maleimide-functionalized lipids in molar ratios of 40:10:50) were dried to form lipid films, and rehydrated in 10 mM bis-tris propane (BTP) at pH 7.0 for 1 hr in the presence of cargo molecules. As shown in FIG. 1A, the resulting liposomes were sonicated and induced to undergo fusion by addition of divalent cations such as $Mg^{2+}$ and $Ca^{2+}$. The resulting MLVs were incubated with DTT (maleimide: DTT ratio of 2:1) to conjugate apposing layers of maleimide-functionalized lipids and form crosslinked ICMVs. The resulting structures were centrifuged, washed, and then PEGylated by incubation with 2 kDa PEG-thiol for 30 min. The final products were centrifuged and washed 3× with deionized water. Particle size and surface charge was determined by dynamic light scattering (DLS) using a 90Plus particle size analyzer (Brookhaven Instruments). The particles were analyzed with confocal microscopy and cryo-TEM. To quantify the fraction of lipids exposed on the external surfaces of particles, lamellarity assay was performed as described previously. (See Girard et al., Biophysical journal 2004; 87:419-429.) For encapsulation studies, ovalbumin (OVA) modified with alexa-fluor 555 were used to measure the amount encapsulated in PEGylated liposomes, lipid-coated PLGA particles (as previously described by Bershteyn et al., Soft Matter 2008; 4:1787-1791), and ICMVs. SIV-Gag and FLT-3 ligand modified with alexa-fluor 555 were used in some assays. Release of OVA from these particles was performed in dialysis membranes with MW cutoff of 100 kDa.

For in vitro dendritic cell (DC) activation studies, bone marrow-derived or splenic DCs were incubated with ICMVs encapsulating OVA in combination with monophorsphoryl lipid A (MPLA) and R-848, TLR4 and TLR7 agonists, respectively. Cells were stained and analyzed by flow cytometry to examine the extent of DC activation and particle internalization. The culture media were analyzed for IL12p70 expression by ELISA (R&D Systems). For analysis of the in vivo function of ICMVs as vaccine carriers, groups of C57Bl/6 mice were immunized s.c. in the flank with either 70 μg of OVA delivered in bolus injection or in ICMVs (with or without TLR agonists) and boosted 21 days later. Frequencies of OVA-specific T-cells and interferon-gamma producing T-cells elicited by immunization were determined by flow cytometry analysis of peripheral blood mononuclear cells. Anti-OVA titers were determined by ELISA analysis of sera from immunized mice. Animals were cared for following NIH, state, and local guidelines.

Results and Discussion

The traditional protocol for forming MLVs was modified to synthesize stable ICMVs (FIG. 1A). First, liposomes containing up to 50 mol % MPB were formed by rehydrating lipid films with sonication in the presence of protein or drug cargo solutions. Fusion among the resulting liposomes was induced by the addition of divalent cations to form MLVs as reported previously. (See Duzgunes et al., J Membrane Biol. 1981; 59:115-125). We then introduced DTT as a membrane-permeable reagent to form covalent crosslinks between maleimide headgroups of apposing lipid membranes within the MLVs (FIG. 1B). As shown in Tables 1A and 1B, both divalent cation and DTT were required to form stable ICMVs with significant yield greater than 40%; MLVs formed with either of $Mg^{2+}$ or DTT alone did not produce significant amount of lipid particles that were centrifuged with 10K×g. The presence of 20 mM sodium chloride interfered with particle formation, as monovalent cation is known to inhibit fusion of vesicles mediated by divalent cations. (See Duzgunes et al., J Membrane Biol. 1981; 59:115-125.) At least 25 mol % or higher MPB were required to achieve a significant yield of particles, and we subsequently chose to work with a lipid composition of DOPC:DOPG:MPB in 40:10:50 molar ratio.

Figure 3B:
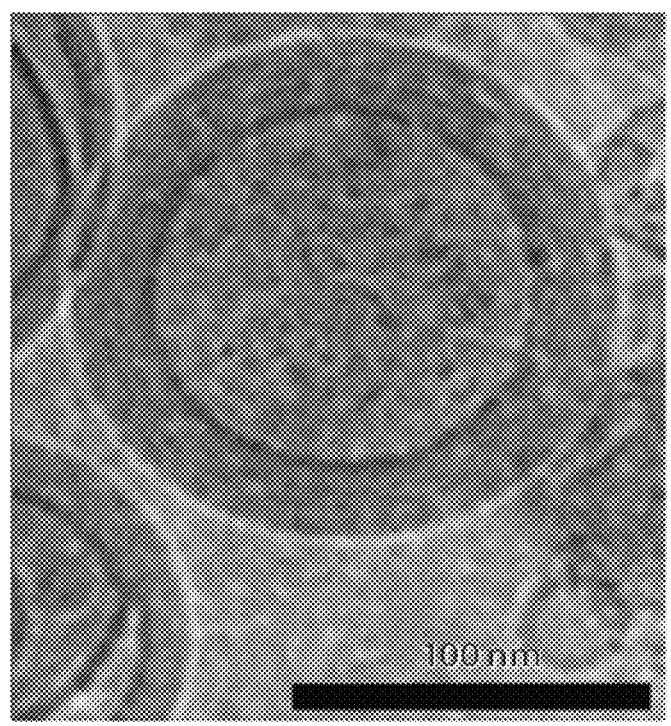

The resulting ICMVs had typical mean diameters of 250±40 nm with polydispersity indices of ~0.08 (FIG. 3A). CryoEM images of the particles revealed multilamellar structures comprised of electron dense bands thicker than single lipid bilayers, suggesting multilayers of lipids conjugated across the lipid membranes (FIG. 3B). The fraction of lipids displayed on the external surfaces of particles was measured with lamellarity assay. Sonicated liposomes had 37±2.3% of lipids on the external surface, whereas the value decreased to 19±1.0% in ICMVs formed after modifying the liposomes with $Mg^{2+}$ and DTT, suggesting their multilayered structures. The ICMVs were PEGylated by reacting surface-displayed MPB with PEG-thiol (2 kDa MW). PEGylation increased the diameter of ICMVs to 272±40 nm, and the particles stored in PBS for 7 days maintained their original sizes (Table 2, and some data not shown). The ICMVs were amenable to lyophilization with 3% sucrose added as an excipient as the particles resuspended in buffered solution after lyophilization maintained their overall morphologies and size characteristics (Table 2).

Figure 4A:
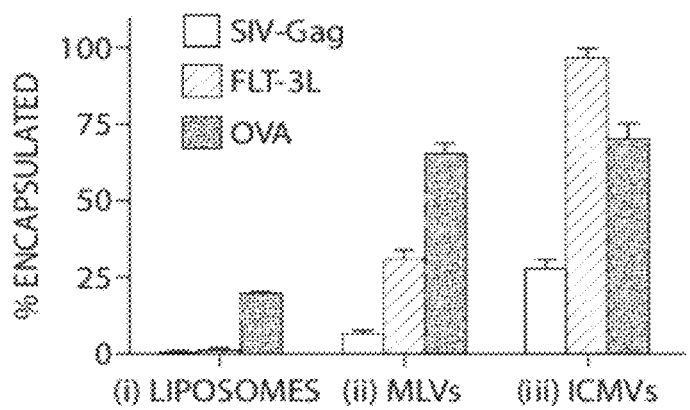
FIGS. 4A-E. Protein encapsulation and release from ICMVs. (A) Encapsulation efficiency of the globular proteins SIV-gag, FLT-3L, or OVA in lipid vesicles collected at each step of ICMV synthesis. (B, C) Comparison of OVA encapsulation efficiency (B), and total protein loading per particle mass (C) in ICMVs vs. dehydration-rehydration vesicles (DRVs) or PLGA nanoparticles. (D) Kinetics of OVA release from simple liposomes, MLVs, or ICMVs (all with base lipid composition 4:5:1 DOPC:MPB:DOPG) incubated in RPMI medium with 10% serum at 37° C. measured over 30 days in vitro. Also shown for comparison are release kinetics for liposomes stabilized with cholesterol and PEG-lipid (38:57:5 DOPC:chol:PEG-DOPE). (E) Release of OVA from ICMVs was measured in buffers simulating different aspects of the endolysomal environment: reducing buffer, 100 mM beta-mercaptoethanol (beta-ME) in PBS; acidic buffer, 50 mM sodium citrate pH 5.0; lipase-containing buffer, 500 ng/mL lipase A in PBS. Data represent the mean±s.e.m of at least three experiments with n=3.

Liposomes and PLGA particles have been widely used for vehicles of protein delivery; therefore, we compared protein encapsulation in these vehicles to ICMVs. As shown in FIG. 5, ICMVs exhibited superior OVA encapsulation efficiency compared to traditional PEGylated stealth liposomes and lipid-coated PLGA particles (108 and 4 fold increases, respectively). Similarly, the amount of OVA encapsulated per total particle mass was enhanced in ICMVs by 21 and 10 fold, respectively. We next examined the amount of various proteins encapsulated in ICMV over the course of its synthesis (FIG. 4A). The amount of SW-gag, FLT-3 ligand, and OVA encapsulated progressively increased from sonicated liposomes, MLVs formed by $Mg^{2+}$-mediated fusion, to ICMVs formed by $Mg^{2+}$ and DTT. In particular, more than 70% of OVA initially loaded was encapsulated in the ICMVs at 407.5±18.7 μg OVA per mg of lipid. Using OVA as a model protein, cargo release from these vesicles was compared (FIG. 6). OVA was released from ICMVs in a slow, continuous manner, whereas OVA was burst-released from liposomes and MLVs in media with serum.

Figure 8A:
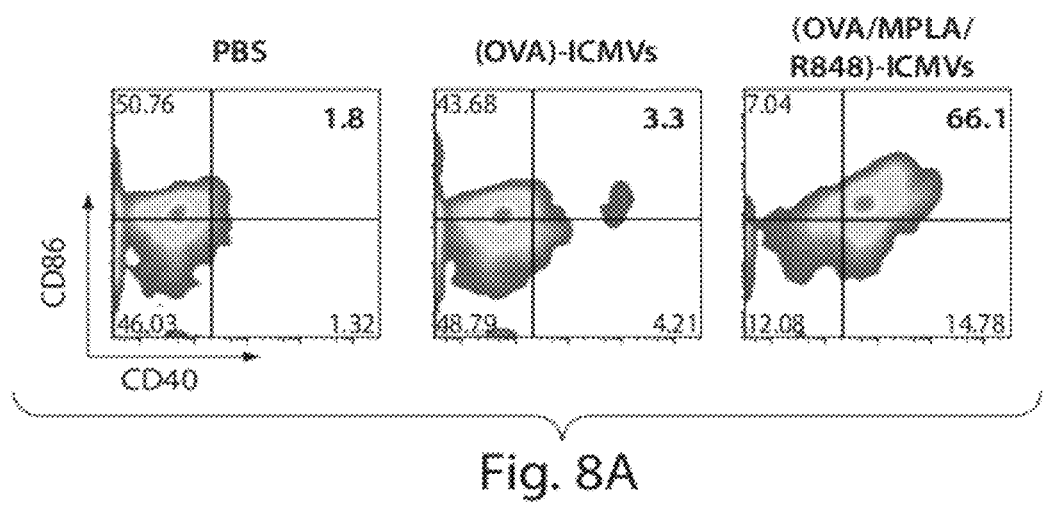
FIGS. 8A-B. (A) DC maturation and (B) activation in response to ICMV-incorporated with MPLA and/or R-848.
Figure 8B:
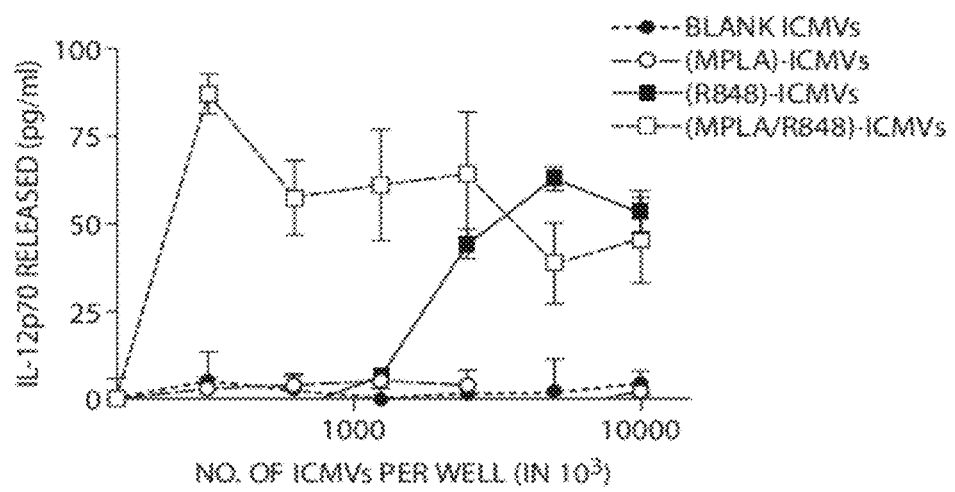

Using OVA as a model vaccine antigen, we examined ICMVs as a platform for vaccine delivery. ICMVs were loaded with OVA and Toll-like receptor agonists, MPLA (TLR4 ligand) and/or resiquimod (TLR7/8 ligand). Dendritic cells (DCs) incubated with OVA-loaded ICMVs in vitro avidly endocytosed the particles. OVA-loaded ICMVs alone did not activate DCs in vitro, but particles bearing TLR agonists (TLRa) triggered upregulation of costimulatory molecules (e.g. CD40, CD80, CD86, and MHC II), and IL-12p70 secretion by DCs in vitro; particles carrying both TLR4 and TLR7 agonists promoted synergistic DC activation (FIG. 8).

Figure 10A:
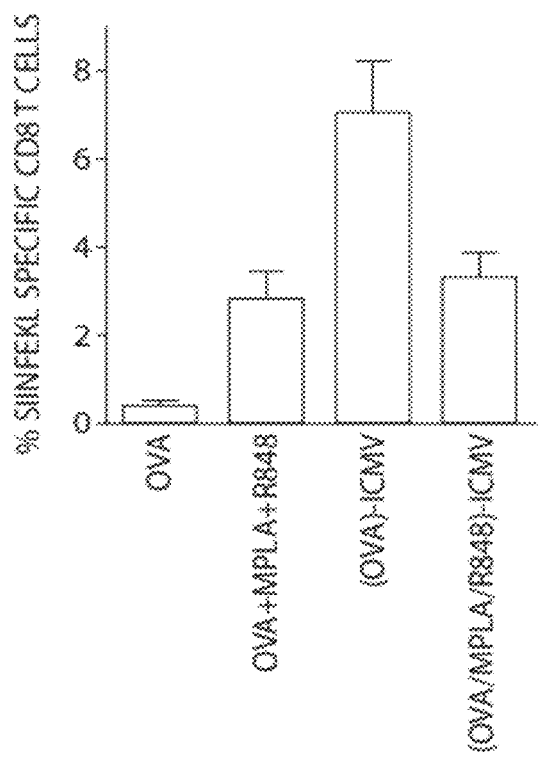
FIGS. 10A-B. (A) OVA-specific CD8+ T cells in peripheral blood after 7 days of boost, as assessed by flow cytometry analysis of cells stained with antibodies against CD8 and peptide-MHC tetramers complexed with the OVA-derived peptide SINFEKL. (B) Anti-OVA antibody titers measured on day 21 of immunization by ELISA.
Figure 10B:
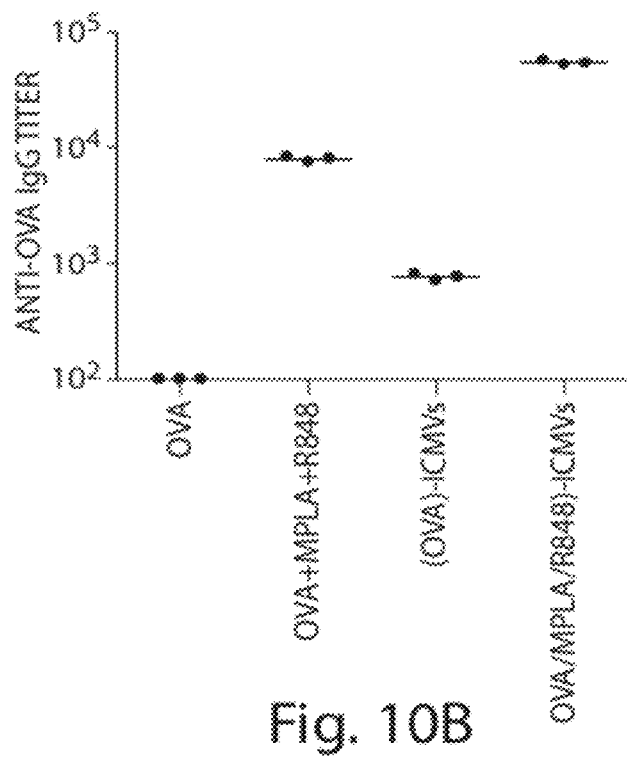

To test the efficacy of particles co-delivering TLRa in combinations with OVA for vaccination in vivo, C57Bl/6 mice were immunized with OVA-loaded ICMVs and compared to the equivalent doses of soluble OVA. Interestingly, compared to the bolus injection of OVA, OVA-loaded ICMVs enhanced expansion of antigen-specific $CD8^+$ T-cells by 17-fold, reaching ~7% among all $CD8^+$ T-cells after boost (FIG. 10). These OVA-loaded particles also elicited the highest frequency of functionally-competent interferon-gamma (IFN-gamma)-producing OVA-specific T-cells. Notably, however, antibody responses against OVA required the presence of TLRa for maximal titers, and OVA-loaded ICMVs co-encapsulated with TLR4 and TLR7 agonists elicited ~10-fold higher anti-OVA antibody titers compared to the same doses of soluble OVA/TLRa (FIG. 10B).

To begin to understand the immune responses that ICMVs can elicit against antigens from clinically-relevant pathogens, we tested immunization with an antigen from an infectious agent. Various doses of ICMVs having the antigen encapsulated therein and also having MPLA incorporated into their bilayers were used to immunize mice. After prime and boost regimen, strong antibody titers were generated against the antigen as detected in sera from day 34, whereas the equivalent doses delivered by soluble antigen and MPLA elicited much weaker antibody titers (data not shown). These results suggest ICMVs as an effective vehicle for delivering antigens for immunizations.

In this study, we developed novel multilamellar lipid particles that exhibit attractive features: Protein encapsulation is greatly enhanced in the ICMVs without the use of organic solvents. These particles exhibit colloidal stability, and the lipid-based particles are fully biodegradable. We demonstrated the versatility of ICMVs as a platform for vaccine delivery. These studies suggest that ICMVs should be broadly useful in a variety of in vivo drug delivery applications.

Example 2

The following Example is a more comprehensive description and reporting of some of the experiments and results described in Example 1.

Currently licensed vaccine adjuvants (e.g., aluminum hydroxide and the oil-in-water emulsion MF59) promote immunity by primarily eliciting humoral immune responses, without stimulating cellular immunity[1,2]. As strong $CD8^+$ T cell (CD8T) responses may be required for vaccines against cancer or intracellular pathogens such as HIV, malaria, and hepatitis C, there is great interest in technologies to promote concerted humoral and cellular immune responses[3,4]. To this end, engineered live vaccine vectors such as non-replicating recombinant viruses have been developed[5-7], which can induce both robust antibody responses and massive expansion of functional antigen-specific $CD8^+$ T-cells in murine models. However, safety concerns with live vectors and anti-vector immunity can complicate live vector vaccine design[7]. Pre-existing vector-specific immune responses have reduced the immunogenicity of live vector-based vaccines in clinical trials[8], and the immune response raised against live vectors following a priming immunization can render booster immunizations using the same vector problematic[7].

In contrast, non-living synthetic vaccines delivering defined antigens can be rationally designed to avoid anti-vector immunity[9]. Such "subunit" vaccines are composed of one or a few selected recombinant proteins or polysaccharides normally present in the structure of the target pathogen. However, subunit vaccines elicit poor or non-existent CD8T responses, due to the low efficiency of cross-presentation (the uptake and processing of extracellular antigen by immune cells for presentation on class I MHC molecules to naive $CD8^+$ T-cells)[10]. To promote cross-presentation, synthetic particles loaded with protein antigens and defined immunostimulatory molecules have been used[11-17], mimicking in a reductionist fashion the cues provided to the immune system during infection by pathogens. Liposomes are particularly attractive materials for this application, due to their low toxicity and immunogenicity, track record of safety in clinical use, ease of preparation, and proven manufacturability at commercial scales[18,19]. Lipid vesicles in the form of unilamellar, multilamellar, or polymerized vesicles have been tested as vaccine delivery materials, with some success[19-23]. Antigens entrapped in lipid vesicles are cross-presented in vivo[19,24,25], and liposomal protein vaccines have been shown to elicit protective T-cell-mediated anti-microbial and anti-tumor immune responses in small-animal models[23,26,27]. However, for diseases such as HIV and cancer, it is currently believed that extremely potent T-cell responses (in concert with humoral immunity) will be required to control the virus/tumors, and therefore, more potent T-cell vaccines are still sought[3,4].

A potential factor influencing the potency of lipid vesicles in vaccine delivery is their limited stability in the presence of serum components. For liposomal cargos that can be processed at high temperature or loaded by diffusion through pre-formed vesicle membranes, enhanced vesicle stability can be achieved by using high-$T_m$ lipids, especially when combined with cholesterol and/or PEGylation[28]. Uni- and multi-lamellar vesicles have also been stabilized by polymerizing reactive headgroups at the surface of bilayers[29], polymerizing reactive groups in phosholipid acyl tails[20,29], or polymerizing hydrophobic monomers adsorbed into the hydrophobic interior of membranes[30]. Common to each of these approaches is the concept of polymerizing components in the plane of the bilayer. However, finding polymerization chemistries that can be carried out in mild conditions compatible with vaccine antigens is challenging[20].

Here we describe a new class of lipid drug carriers, inter-bilayer-crosslinked multilamellar vesicles (ICMVs), formed by stabilizing multilamellar vesicles with short covalent crosslinks linking lipid headgroups across the apposing faces of adjacent tightly-stacked bilayers within the vesicle walls. ICMVs encapsulated and stably retained high levels of proteins, releasing entrapped cargo very slowly when exposed to serum (over 30 days) compared to simple liposomes or multilamellar vesicles (MLVs) of the same lipid composition. However, these vesicles were quickly degraded in the presence of lipases normally found at high levels within intracellular compartments[31]. Using this novel vesicle structure to co-entrap high levels of a model protein antigen (ovalbumin, OVA) and a lipid-like immunostimulatory ligand (monophosphoryl lipid A, MPLA), we carried out immunization studies in mice and found that ICMVs elicited robust antibody titers ~1000-fold greater than simple liposomes and ~10-fold greater than MLVs of identical lipid compositions. Unlike live vectors that are often only effective for a single injection administered to a vector-naïve individual, these synthetic vesicles triggered steadily increasing humoral and CD8+ T-cell responses following repeated administrations, with antigen-specific T-cells expanding to a peak of nearly 30% of the total CD8+ T-cells in blood following a prime and two booster immunizations. These new materials may thus open the door to subunit vaccines that are both safe and highly effective for generating both humoral and cellular immunity.

Materials and Methods

Synthesis of ICMVs. 1.26 µmol of lipids in chloroform (typical lipid composition: DOPC(1,2-Dioleoyl-sn-Glycero-3-Phosphocholine):DOPG(1,2-di-(9Z-octadecenoyl)-sn-glycero-3-phospho-(1'-rac-glycerol)):MPB (1,2-dioleoyl-sn-glycero-3-phosphoethanolamine-N-[4-(p-maleimidophenyl) butyramide)=4:1:5 molar ratio, all lipids from Avanti Polar Lipids, Alabaster, Ala.) were dispensed to glass vials, and the organic solvents were evaporated under vacuum overnight to prepare dried thin lipid films. The lipid films were rehydrated in 10 mM bis-tris propane (BTP) at pH 7.0 with cargo proteins for 1 hr with rigorous vortexing every 10 mM, and then sonicated in alternating power cycles of 6 watts and 3 watts in 30 s intervals for 5 min on ice (Misonix Microson XL probe tip sonicator, Farmingdale, N.Y.). The liposomes formed in this first step were induced to undergo fusion by addition of divalent cations such as $Mg^{2+}$ and $Ca^{2+}$ at a final concentration of 10 mM. The resulting MLVs were incubated with 1.5 mM DTT (maleimide:DTT molar ratio of 2:1) for 1 hr at 37° C. to conjugate opposing bilayers of maleimide-functionalized lipids and form crosslinked ICMVs; the resulting vesicles were recovered by centrifugation at 14,000×g for 4 min, and washed twice with deionized water. For PEGylation, the particles were incubated with 2 kDa PEG-thiol (Laysan Bio, Arab, Ala.) in a 1.5-fold molar excess of PEG-SH to maleimide groups for 1 hr at 37° C. The resulting particles were centrifuged and washed 3× with deionized water. The final products were either stored in PBS at 4° C. or lyophilized in the presence of 3% sucrose as a cryoprotectant and stored at −20° C. For some assays, simple liposomes or Mg-fused MLVs were harvested prior to crosslinking with ultracentrifugation at 115K g using an Optima ultracentrifuge for 6 hrs (Beckman Coulter).

In vitro protein loading and drug release. For encapsulation studies, ovalbumin (OVA, Worthington, Lakewood, N.J.), SIV-gag (Advanced Bioscience Laboratories, Kensington, Md.), and FLT-3L (Peprotech, Rocky Hill, N.J.) were labeled with Alexa-Fluor 555 (Invitrogen, Carlsbad, Calif.) for direct fluorometric quantification of the amount of protein entrapped. OVA was also encapsulated in DRVs and PLGA nanoparticles as described previously[43,44]. In some experiments, ICMVs were loaded with a recombinant vivax malaria protein (VMP) as an irrelevant antigen control[49] (257 amino acid protein, provided by Dr. Anjali Yadava, Walter Reed Army Institute of Research, described in U.S. Patent Application Publication No. US 20090196883A1 published Aug. 6, 2009, the amino acid sequence of which is provided herein as SEQ ID NO:1, and the nucleotide sequence of which is provided herein as SEQ ID NO:2). Capped-thiol OVA was prepared by incubating 1 mg of OVA with 1.5 mM TCEP for 1 hr at RT, followed by incubation with 1.5 mM ethyl-maleimide (Pierce, Rockford, Ill.) at 37° C. for 1 hr. The extent of thiol protection was >95% as assessed with Ellman's assay[50]. Release of OVA labeled with Alexa-Fluor 555 from lipid vesicles was quantified in RPMI media supplemented with 10% fetal calf serum at 37° C. using dialysis membranes with MW cutoff of 100 kDa. At regular intervals, the releasing media were removed for quantification of fluorescence, and an equal volume of fresh media were replaced for continued monitoring of drug release. Residual OVA remaining at the end of the time-course was determined by lipid extraction of vesicles with 1% Triton X-100 treatment and measuring released protein by fluorescence spectrophotometry. OVA release assays were also performed in Hank's buffered saline solution supplemented with 500 ng/ml of phospholipase A (Sigma, St. Louis, Mo.). To examine stability of encapsulated cargo molecules, monoclonal rat IgG encapsulated in ICMVs was retrieved with 1% triton X-100 treatment and analyzed with SDS-PAGE under non-reducing conditions with silver staining (Pierce).

Vaccination Study with ICMVs.

Groups of C57Bl/6 mice (Jackson Laboratories) were immunized s.c. in the tail base with indicated doses of OVA (with or without TLR agonist MPLA). Frequencies of OVA-specific CD8+ T-cells and their phenotypes elicited by immunization were determined by flow cytometry analysis of PBMCs at selected time points following staining with DAPI (to discriminate live/dead cells), anti-CD8 alpha, anti-CD44, anti-CD62L, and SIINFEKL/H-2K$^b$ peptide-MHC tetramers (Becton Dickinson). To assess functionality of primed CD8+ T-cells, PBMCs were stimulated ex vivo with 1 µM OVA-peptide SIINFEKL for 6 hrs with GolgiPlug (Becton Dickinson), fixed, permeabilized, stained with anti-IFN-gamma and CD8 alpha, and analyzed by flow cytometry. Anti-OVA IgG titers, defined as the dilution of sera at which 450 nm OD reading is 0.5, were determined by ELISA analysis of sera from immunized mice. Animals were cared for following NIH, state, and local guidelines.

Statistical Analysis.

Statistical analysis was performed with Jmp 5.1 (SAS Institute Inc, Cary, N.C.). Data sets were analyzed using one- or two-way analysis of variance (ANOVA), followed by Tukey's HSD test for multiple comparisons. p-values less than 0.05 were considered statistically significant. All values are reported as mean±s.e.m.

Results

We introduced covalent crosslinks between functionalized lipid headgroups of adjacent, apposed bilayers within pre-formed MLVs to form ICMVs (FIG. 2A): In a typical synthesis, dried phospholipid films containing DOPC, anionic DOPG, and the anionic maleimide-headgroup lipid MPB in a 4:1:5 molar ratio were hydrated and sonicated to form simple liposomes (step (i)). Divalent cations (e.g., $Mg^{2+}$) were added to the liposomes to induce vesicle fusion and the formation of MLVs as reported previously[32] (step (ii)). To introduce crosslinks between adjacent bilayers in the MLVs, dithiolthrietol (DTT) was then added to the vesicle suspension to act as a membrane-permeable crosslinker, forming a covalent linkage between maleimide headgroups of apposed membranes brought into proximity by the cation salt bridges formed between vesicle layers (step (iii)). PEGylation is a well-known strategy to increase the serum stability and blood circulation half-life of lipid vesicles[18]. Thus as a final step, the vesicles were washed and residual maleimide groups exposed on the external surfaces of the particles were capped with thiol-terminated PEG (step (iv)).

The diameter/polydispersity of the particles will determine the cell types capable of internalizing these particles[33], while the number of bilayers comprising the vesicle walls would be expected to impact the stability of the vesicles and their ability to retain/slowly release cargos in the presence of serum. To evaluate these properties and better understand the process of ICMV formation, we characterized the products at each step of the synthesis: The initial liposomes formed by sonication (step (i)) had hydrodynamic diameters of ~190 nm, and the size increased slightly to ~240 nm following $Mg^{2+}$-mediated vesicle fusion (step (ii)) and subsequent DTT "stapling" of the bilayers (step (iii), Table 2). The resulting ICMVs showed a monomodal, relatively narrow size distribution (comparable to common lipid vesicle or polymer nanoparticle preparations[12,21]), and there was no evidence for gross aggregation of particles during the crosslinking step from dynamic light scattering (DLS) or cryoelectron microscopy (FIGS. 2A, B, and Table 2). Addition of thiol-terminated PEG to DTT-treated vesicles quenched remaining detectable maleimide groups on the surfaces of MLVs and introduced PEG chains on ~2 mol % of the surface-exposed lipids of ICMVs without significantly altering particle diameters (Table 2 and data not shown). PEGylated ICMVs stored at 4° C. or 37° C. in PBS remained stable over 7 days, and they were amenable to lyophilization with 3% sucrose added as an excipient[34], highlighting their compatibility with long-term storage conditions (Table 2 and data not shown). We imaged the initial liposomes, $Mg^{2+}$-fused MLVs, and the final ICMVs by cryoelectron microscopy (FIG. 2A), and saw that crosslinking with DTT led to the formation of vesicles with thick multilamellar walls composed of tightly stacked bilayers resolved as ~4-5 nm electron-dense striations. The median number of bilayers per particle was 4.4 (interquartile range [IQR], 3.3-6.9), and the median particle radius to lipid wall thickness ratio was 3.8 (IQR, 2.4-6.8) (FIGS. 2C, D). Interestingly, the majority of ICMVs had vesicle walls composed of concentric bilayers, although a few examples of ICMVs with surface defects in the form of incomplete external lipid layers could also be found (data not shown). Consistent with the increased lamellarity of the vesicles following cation-mediated fusion and DTT crosslinking observed by electron microscopy imaging, the fraction of lipids exposed on the external surfaces of the vesicles decreased in steps (ii) and (iii) of the synthesis, as measured by a bulk dye-quenching lamellarity assay[35] (Table 2). Chemical evidence for crosslinking between the maleimide-lipids following MT treatment was found in thin-layer chromatography and MALDI-TOF measurements on ICMVs (data not shown). Importantly, both the particle size and individual lamellarity distributions were monomodal, with less than 3% contaminating unilamellar vesicles and no large aggregates, which could skew the functional properties (e.g., protein release) of the particles. The ICMVs have a size that should be avidly taken up by monocytes and dendritic cells[36], and a crosslinked multilamellar wall structure that will stabilize protein entrapment compared to traditional unilamellar or multilamellar liposomes.

Analysis of the conditions required to form stable vesicles provided insight into the mechanisms of ICMV formation. Following interbilayer-crosslinking, ICMVs could be collected by centrifuging at 14,000×g for 4 min ("low-speed conditions"), whereas simple liposomes or MLVs of identical lipid composition required ultracentrifugation to pellet. Using the mass of particles collected by low-speed centrifugation as a surrogate measure of crosslinked vesicle yield, we found that both divalent cation-mediated fusion (FIG. 2A step (ii), either $Mg^{2+}$ or $Ca^{2+}$) and DTT treatment (step (iii)) were required for ICMV formation (Tables 1A, B). Precursor vesicles treated with either $Mg^{2+}$ or DTT alone even at 10× molar excess relative to maleimide groups did not generate significant yields of particles (Tables 1A, B). In addition, at least 25 mol % MPB was required to form ICMVs (Tables 1A, B); the high level of reactive headgroups required for substantial ICMV yield may reflect competition between intra- (between headgroups on the same bilayer) and inter-bilayer crosslink formation. DTT could be replaced with DPDPB, another membrane-permeable dithiol, but not with 2 kDa PEG-dithiol under the conditions used (Tables 1A, B). ICMVs could also be formed using only DOPC and MPB lipids, or using cationic DOTAP in place of DOPG (data not shown). As an alternative method to form ICMVs, maleimide-dithiol crosslinking could be replaced with bio-orthogonal click chemistry, employing alkyne-terminated lipids for vesicle formation and diazides for crosslinking[37,38] (FIG. 12 and data not shown). Thus, interbilayer-crosslinking for the formation of stabilized vesicles is a general strategy that can be adapted to other lipid/crosslinker chemistries. Based on their high synthetic yield and colloidal stability, we chose to focus on PEGylated ICMVs with a lipid composition of DOPC:DOPG:MPB in a 4:1:5 molar ratio for further testing as protein/vaccine delivery vehicles.

To test the suitability of ICMVs for protein delivery, we examined the entrapment of several globular proteins: SIV-gag, an HIV vaccine antigen; FLT-3L, a therapeutic cytokine; and ovalbumin (OVA), a model vaccine antigen. Protein encapsulation was achieved by rehydrating dried lipids with protein solutions in step (i) of the synthesis (FIG. 2A). The amount of encapsulated protein increased at each step of the ICMV preparation (FIG. 4A), which may reflect additional protein entrapment occurring as vesicle fusion occurs in both steps (ii) and (iii). Protein entrapment in ICMVs was not mediated by conjugation of thiols on the cargo proteins with the maleimide-functionalized lipid vesicles, as OVA pre-re-duced with TCEP and treated with ethyl-maleimide to block all thiol groups on the protein was encapsulated in ICMVs at levels similar to unmodified protein (76.1±6.3% vs.

Figure 4B:
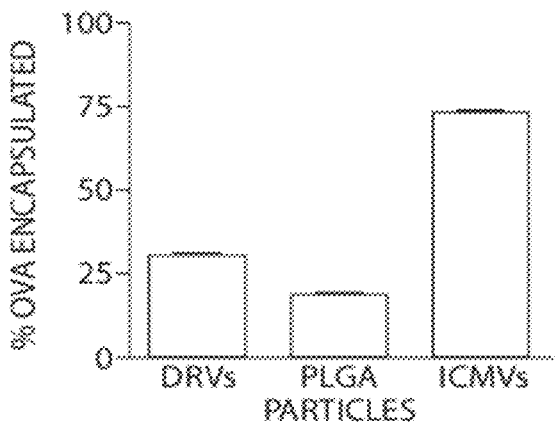
Figure 4C:
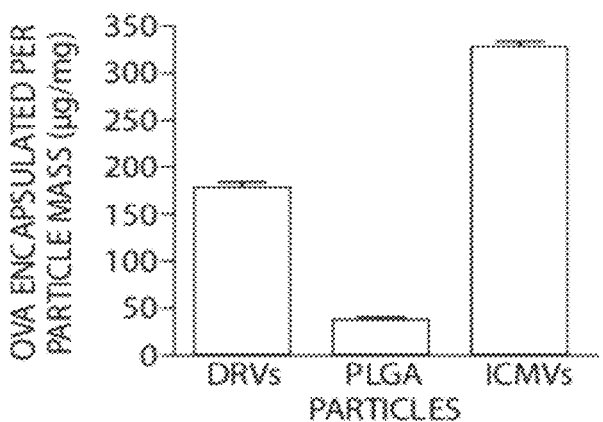

83.3±8.4% for capped-thiol- vs. unmodified OVA; p=0.17). We also confirmed that disulfide linkages in model protein cargos were not reduced by the DTT crosslinker during the vesicle formation process and that ICMV encapsulation did not trigger protein aggregation (data not shown). To directly compare the efficiency and quantity of protein loading achieved with ICMVs to two of the most common types of drug delivery vehicles[39-41], we compared encapsulation of OVA in liposomes, PLGA nanoparticles, and ICMVs: Using a model stable lipid composition comprised of phosphocholine, PEG-lipid, and cholesterol[42], we formed DRVs as one of the most efficient aqueous entrapment approaches for liposomes[43], and prepared OVA-loaded PLGA particles using a double-emulsion solvent-evaporation process[44]. ICMVs exhibited superior encapsulation efficiency (~75%) compared to either DRVs or PLGA particles (2-, and 4-fold increases, respectively; FIG. 4B), and the amount of OVA encapsulated per total particle mass (~325 μg OVA per mg of particles) was increased in ICMVs by 1.8-, and 9-fold compared to DRVs or PLGA particles, respectively (FIG. 4C). Thus, ICMVs appear to be effective for encapsulating a variety of globular proteins, and, at least for the model antigen OVA, ICMVs loaded protein more efficiently than common alternative protein carriers.

Figure 4D:
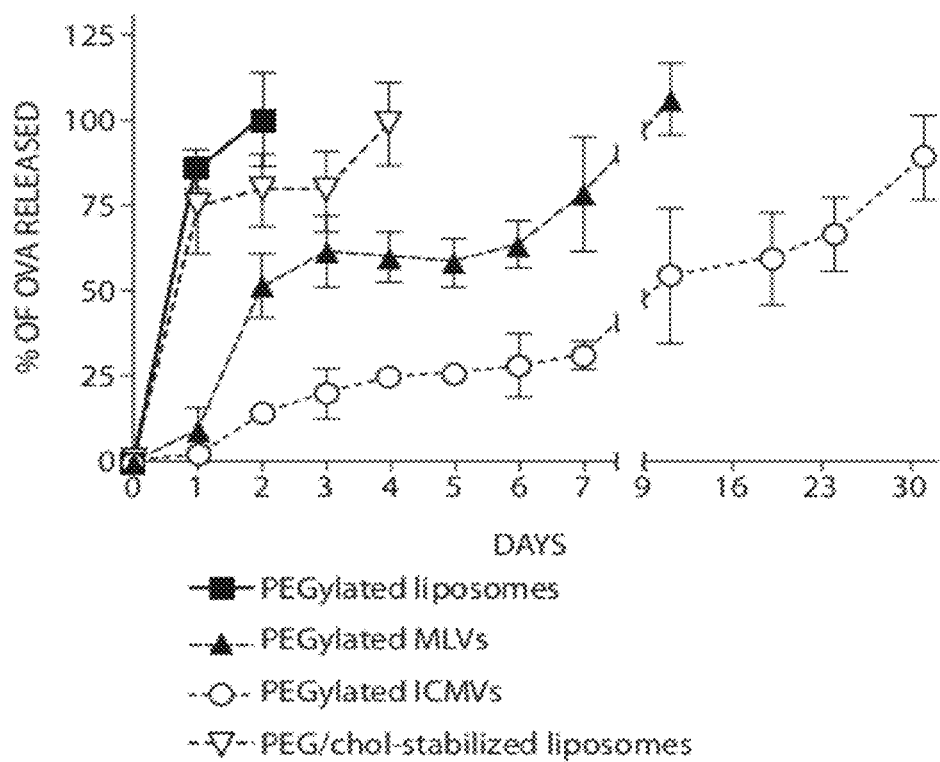
Figure 4E:
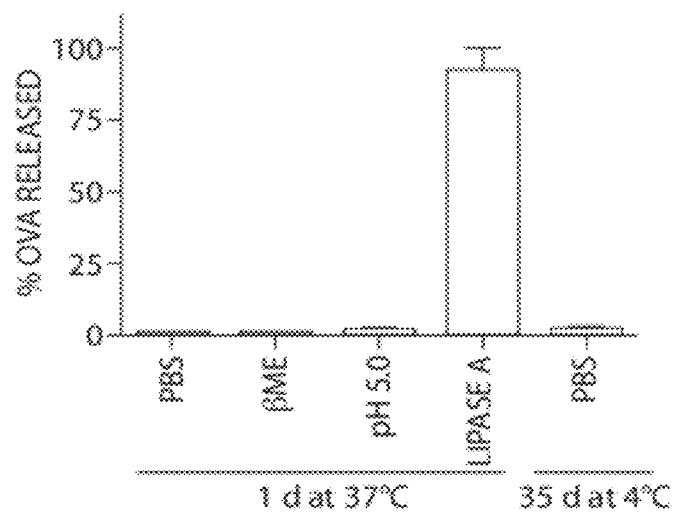

We next determined whether interbilayer crosslinking enabled lipid vesicles retain biodegradability while increasing protein retention in the presence of serum. OVA was loaded into PEGylated liposomes, $Mg^{2+}$-fused MLVs, or ICMVs all with the same lipid composition, and the kinetics of protein release at 37° C. in media containing 10% fetal calf serum were quantified. Unilamellar liposomes quickly released their entire payload of entrapped OVA within ~2 days, while multilamellar $Mg^{2+}$-fused MLVs released ~50% of their entrapped cargo over the same time period (FIG. 4D). However, ICMVs showed a significantly enhanced retention of protein, releasing only ~25% of their cargo by one week, and ~90% after 30 days (FIG. 4D). Notably, ICMVs also released protein significantly more slowly than unilamellar liposomes stabilized by the inclusion of cholesterol[42] (FIG. 4D). The crosslinked vesicles also retained ~95% of their entrapped protein when stored in PBS at 4° C. for over 30 days (FIG. 4E). We also examined protein release from ICMVs in conditions modeling intracellular compartments: vesicles incubated in reducing or acidic conditions for 1 day at 37° C. retained >95% of entrapped OVA, whereas incubation with phospholipase A led to release of >90% OVA and rapid vesicle degradation (FIG. 4E). Thus, ICMVs exhibit enhanced stability in the presence of serum compared to traditional liposomal formulations, but rapidly break down in the presence of enzymes that are present within intracellular endolysosomal compartments[31], providing a mechanism for triggered intracellular release of cargo following internalization by cells. Although some protein degradation within vesicles might be possible upon administration in vivo prior to internalization by cells, critical uptake and processing of antigen will occur in the first few days after immunization in vaccine delivery[45], when such degradation processes should be minimal.

Figure 7A:
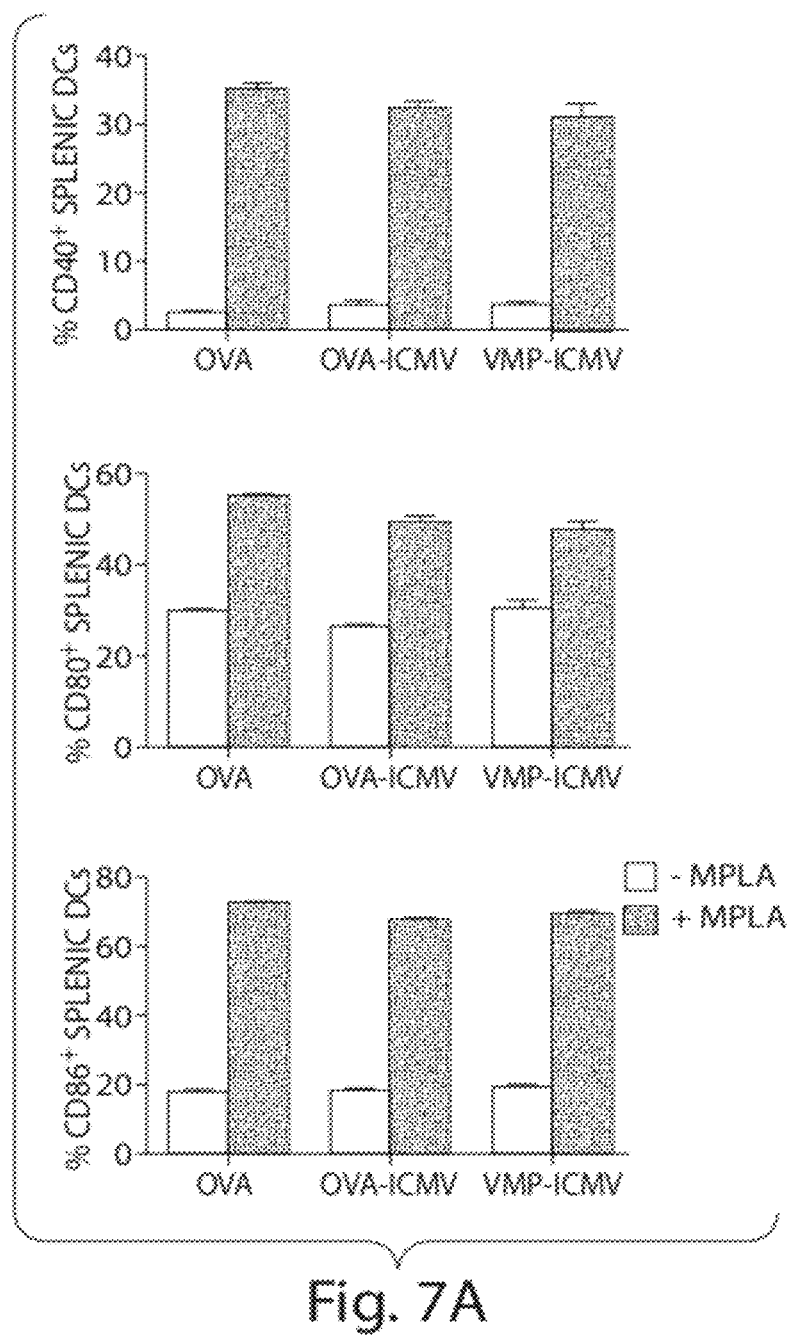
FIGS. 7A-C. In vitro stimulation of immune responses by ICMVs supplemented with the TLR agonist MPLA. (A) Flow cytometry analysis of expression of the cell surface costimulatory markers CD40, CD80, and CD86 on splenic dendritic cells (DCs) after 18 hr incubation with 0.7 μg/mL soluble OVA, equivalent doses of OVA loaded in ICMVs, or ICMVs loaded with an irrelevant protein (vivax malaria protein, VMP), in the presence or absence of 0.1 μg/mL MPLA. (B) Splenic DCs were incubated for 18 hr with 10 μg/mL SINFEKL peptide ($OVA_{257-264}$), 5.0 μg/mL soluble OVA, equivalent doses of OVA loaded in ICMVs, or VMP-loaded ICMVs in the presence or absence of 0.05 μg/mL MPLA, and the extent of cross-presentation of OVA was assessed by flow cytometry analysis of cells stained with the 25-D1.16 mAb that recognizes SIINFEKL complexed with $H-2K^b$. (C) 5-(6)-carboxyfluorescein diacetate succinimidyl diester (CFSE)-labeled OVA-specific naïve OT-I $CD8^+$ T-cells were co-cultured with syngeneic splenic DCs pulsed with soluble 0.7 μg/mL OVA mixed with 0.1 μg/mL MPLA, or equivalent doses of OVA-loaded ICMVs mixed with MPLA. Empty ICMVs without antigen or ICMVs loaded with the irrelevant antigen VMP were included as negative controls. Proliferation of $CD8^+$ T-cells was assessed on day 3 by flow cytometry analysis of the dilution of CFSE in the OT-I $CD8^+$ T-cells; shown are histograms of CFSE fluorescence. Gates on each histogram indicate the percentage of divided cells in each sample. Data represent the mean±s.e.m of at least three experiments with n=3-4.
Figure 7B:
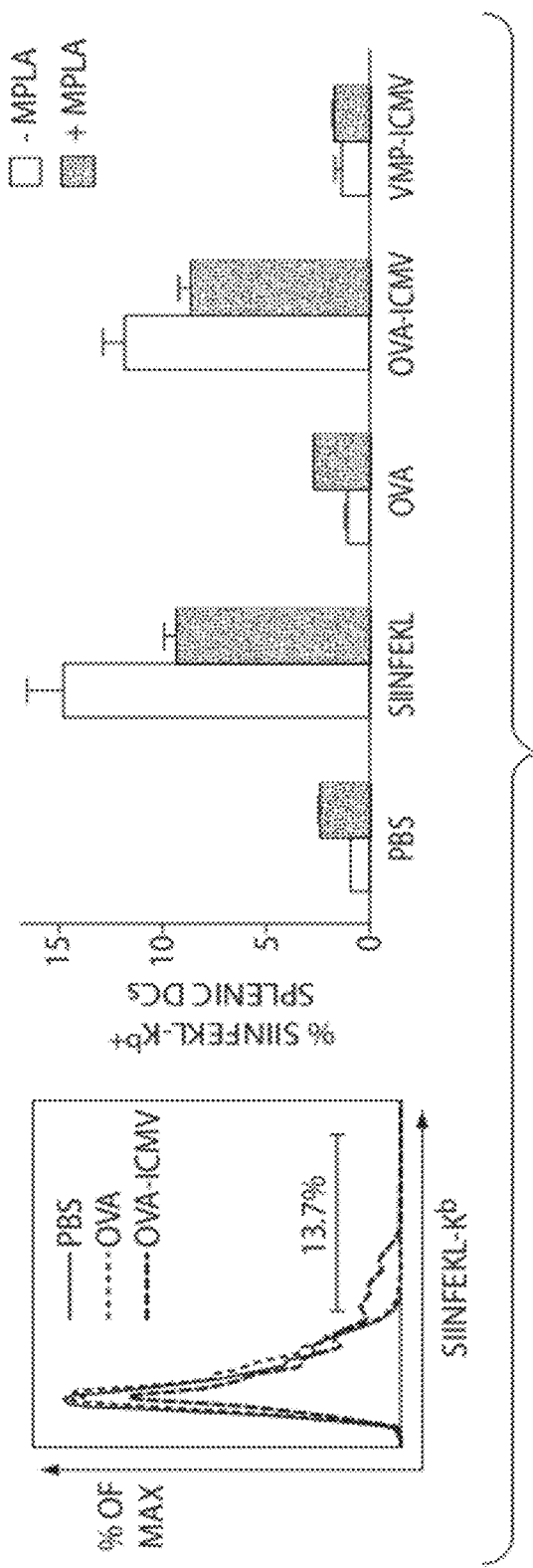
Figure 7C:
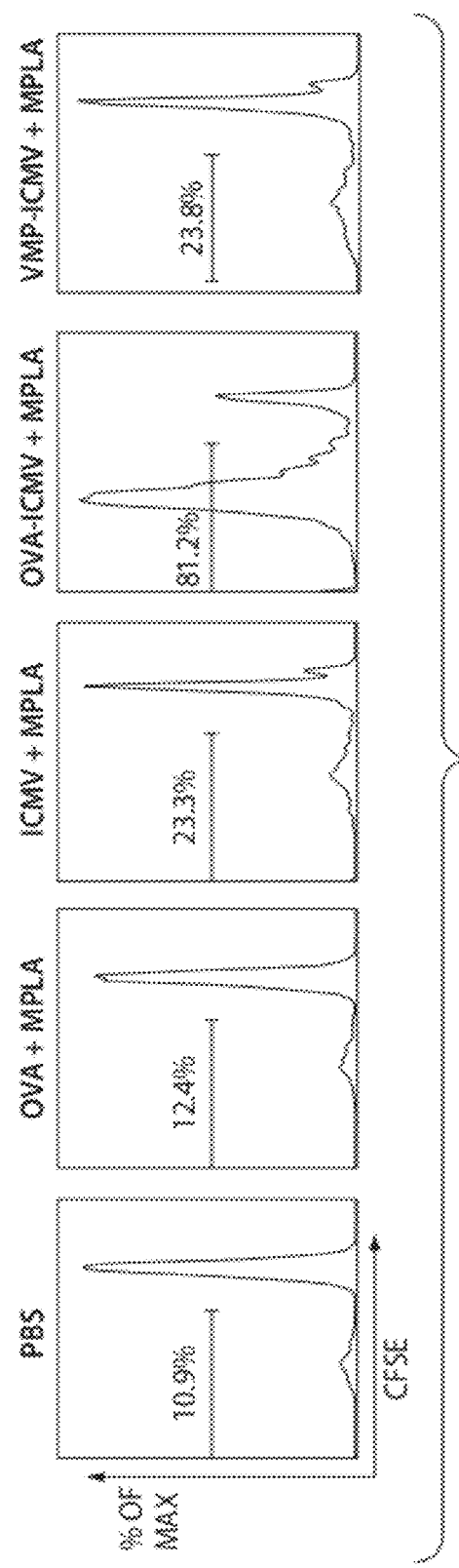

We hypothesized that the unique structure of ICMVs, with efficient retention of encapsulated protein antigens in the extracellular environment but rapid release in endosomes/lysosomes, would provide enhanced vaccine responses. To generate vaccine ICMVs, we prepared vesicles carrying the model antigen OVA (OVA-ICMVs) and mixed these vesicles with the molecular adjuvant monophosphoryl lipid A (MPLA). MPLA is an FDA-approved agonist for Toll-like receptor (TLR) 4 expressed by dendritic cells, B-cells, and innate immune cells, that potently amplifies vaccine responses[1,46]. Antigen-loaded ICMVs mixed with MPLA promoted upregulation of costimulatory molecules on splenic and bone-marrow dendritic cells (DCs) in vitro, compared to DCs pulsed with ICMVs without MPLA (FIG. 7A and data not shown). DCs pulsed with ICMVs cross-presented peptides derived from OVA with greatly enhanced efficiency compared to those pulsed with soluble OVA (with or without added MPLA), as determined by staining DCs with the 25-D1.16 mAb that recognizes the SIINFEKL peptide ($OVA_{257-264}$) complexed with MHC class I H-$2K^b$ molecules (p<0.001, compared to soluble OVA or ICMVs-loaded with irrelevant antigen [vivax malaria protein, VMP], FIG. 7B). Splenic DCs incubated with OVA-ICMVs+MPLA triggered robust proliferation of OVA-specific naïve OT-1 $CD8^+$ T-cells in vitro, as assessed by a carboxyfluorescein succinimidyl ester (CFSE) dilution assay. In contrast, weak T-cell responses were detected when DCs were pulsed with equivalent doses of soluble OVA and MPLA, empty ICMVs, or VMP-ICMVs, indicating the specificity of the T-cell responses elicited by ICMVs (FIG. 7C). These results suggest that addition of MPLA allows equivalent DC activation by ICMVs or soluble OVA, but ICMVs trigger enhanced cross-presentation of the antigen, as expected for particulate antigen delivery.

Figure 9A:
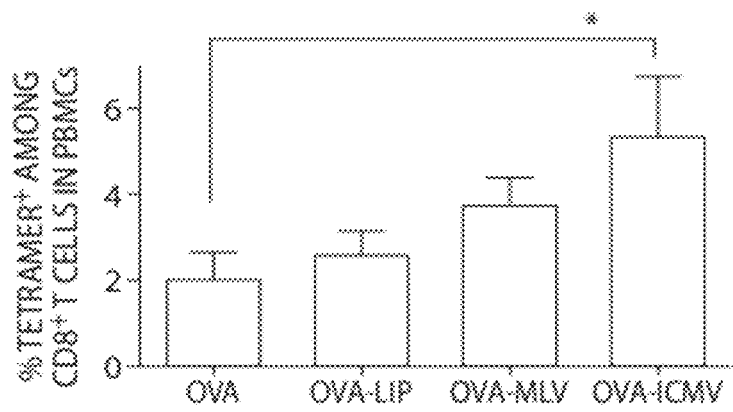
FIGS. 9A-F. In vivo immunization with ICMVs vs. soluble antigen or antigen encapsulated in non-crosslinked vesicles. a, b, C57Bl/6 mice were immunized subcutaneously (s.c.) with a single injection of 10 μg OVA delivered in soluble, liposomal, MLV, or ICMV formulations, each mixed with 0.1 μg of MPLA. (A) The percentage of antigen-specific $CD8^+$ T-cells was determined by flow cytometry analysis of peripheral blood mononuclear cells (PBMCs) 7 days post immunization with fluorescent OVA peptide-MHC tetramers. (B) Sera from the immunized mice were analyzed by ELISA 21 days post immunization for OVA-specific IgG. (C, D) C57Bl/6 mice were injected with 10 μg of fluorophore-conjugated OVA mixed with 0.1 μg of MPLA as a soluble, liposomal, or ICMV formulation, and the draining inguinal lymph node (dLN) cells that internalized OVA were assessed on day 2. (C) Shown are percentages of DCs ($CD11c^+$), macrophages ($F4/80^+$), B cells ($B220^+$), and plasmacytoid DCs ($CD11c^+B220^+$) positive for OVA uptake, and (D) the mean fluorescence intensity (MFI) of $OVA^+$ populations. (E, F) C57Bl/6 mice were injected with 10 μg of OVA mixed with 0.1 μg of MPLA as a soluble, liposomal, or ICMV formulation, and 2 days later, DCs isolated from draining inguinal LNs were analyzed by flow cytometry to assess DC activation and antigen cross-presentation. (E) Overlaid histograms show costimulatory markers (CD40 and CD86) and MHC-II expression in DCs. (F) The left panel shows overlaid histograms of inguinal LN DCs stained for $SINFEKL-K^{b+}$ complexes, and mean MFI levels are shown on the right panel. Data represent mean±s.e.m of 2-3 independent experiments conducted with n=3-4. *, p<0.05 and **, p<0.01, analyzed by one-way ANOVA, followed by Tukey's HSD.
Figure 9B:
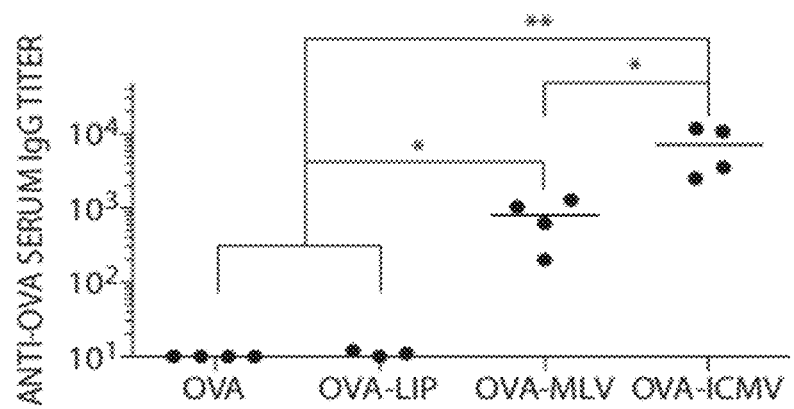
Figure 9C:
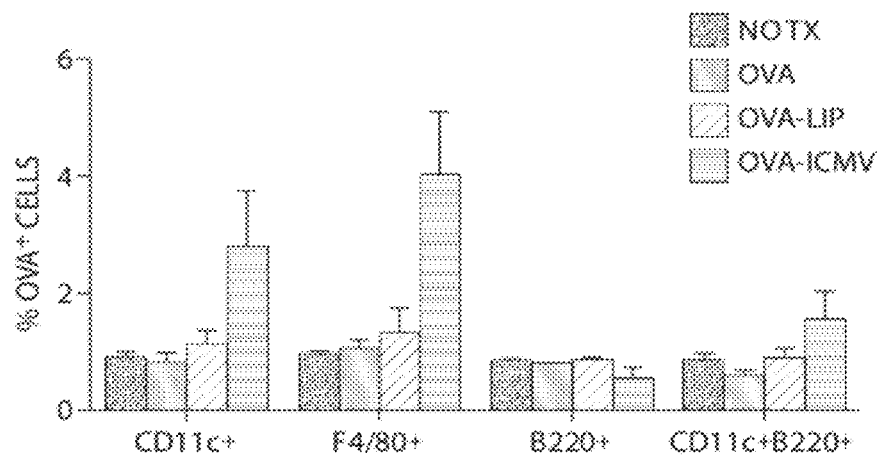
Figure 9D:
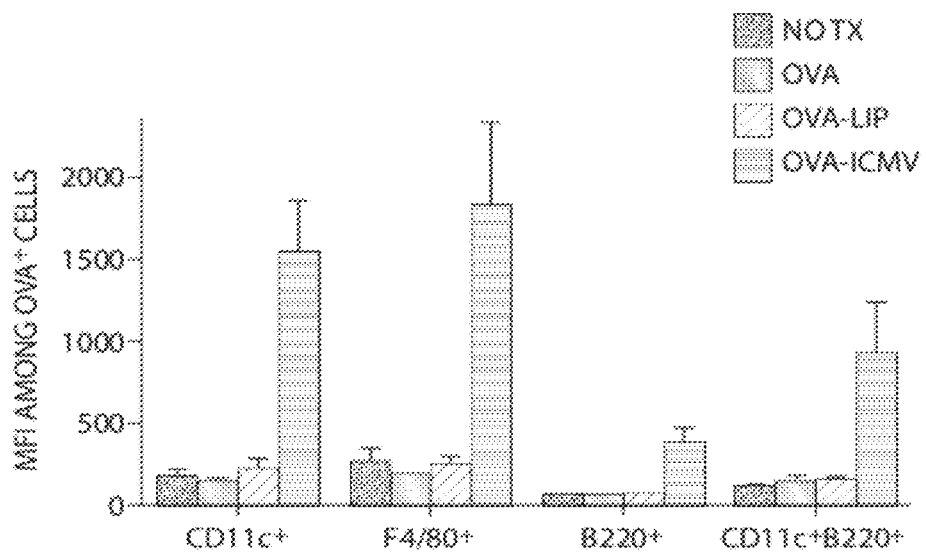
Figure 9E:
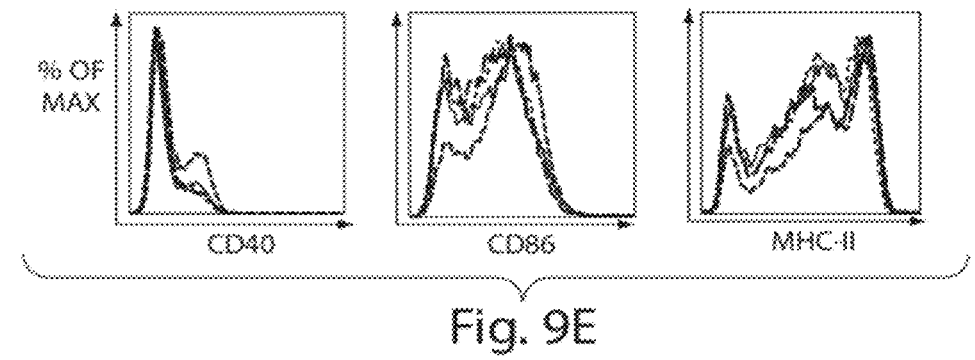
Figure 9F:
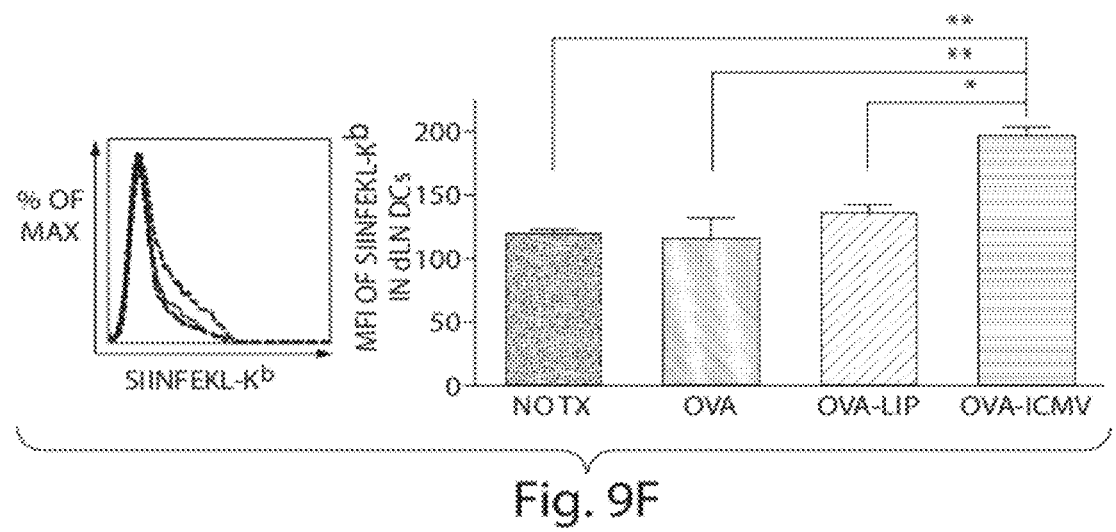

To determine the influence of vesicle structure on the immune response in vivo, we vaccinated C57Bl/6 mice with equivalent doses of OVA, MPLA, and lipids (10 μg, 0.1 μg, and 142 μg, respectively) in the form of PEGylated unilamellar liposomes, MLVs, or ICMVs. Seven days after immunization, we assessed the strength of the endogenous $CD8^+$ T-cell response by analyzing the frequency of OVA peptide-MHC tetramer (antigen-specific) $CD8^+$ T-cells among peripheral blood mononuclear cells (PBMCs) by flow cytometry, and found a trend toward increasing T-cell responses in the order soluble OVA<liposomes<$Mg^{2+}$-fused MLVs<ICMVs (FIG. 9A). At 3 weeks post-immunization, $Mg^{2+}$-fused MLVs elicited ~100-fold greater OVA-specific IgG titers in the sera of the animals compared to soluble OVA or unilamellar liposomes. However, ICMV immunization generated a substantially stronger humoral response, ~1000-fold and ~10-fold greater than the soluble OVA (p<0.01) and non-crosslinked MLV immunizations (p<0.05), respectively (FIG. 9B). Thus, the stabilized structure of ICMVs promoted both T-cell and antibody responses. Enhanced T-cell and antibody responses to immunization with ICMVs compared to other formulations, could be attributed to improved antigen delivery to antigen-presenting cells (APCs), enhanced activation of DCs, enhanced antigen cross-presentation (as seen in vitro), or a combination of these factors. To distinguish between these possibilities, mice were immunized with fluorophore-conjugated OVA mixed with MPLA as a soluble, liposomal, or ICMV formulation, and the draining inguinal lymph node cells that internalized OVA were assessed on day 2. OVA delivered by ICMVs was readily detected in total DCs, macrophages, and plasmacytoid ($CD11c^+B220^+$) DCs in the draining lymph nodes (dLNs), while soluble and liposomal formulations showed fluorescence barely above background (p<0.01, FIGS. 9C, D). Repeating this analysis with unlabeled OVA, we found that administration of OVA-ICMVs with MPLA triggered a minor enhancement of co-stimulatory marker and MHC-II expression among DCs in dLNs compared to soluble or liposomal OVA+MPLA (FIG. 9E and data not shown). However, using the 25-D1.16 antibody to detect OVA peptide presentation, we readily detected OVA peptide-MHC complexes on DCs in the dLNs following ICMV immunization, whereas soluble OVA or liposomal OVA injections did not give staining above the expected background cross-reactivity of 25-D1.16 with self-peptide MHC complexes[47] (FIG. 9F). All together, these results suggest that improved retention of entrapped antigen in the crosslinked multilamellar structures of ICMVs leads to enhanced antigen delivery to APCs, followed by enhanced cross-presentation.

Figure 11A:
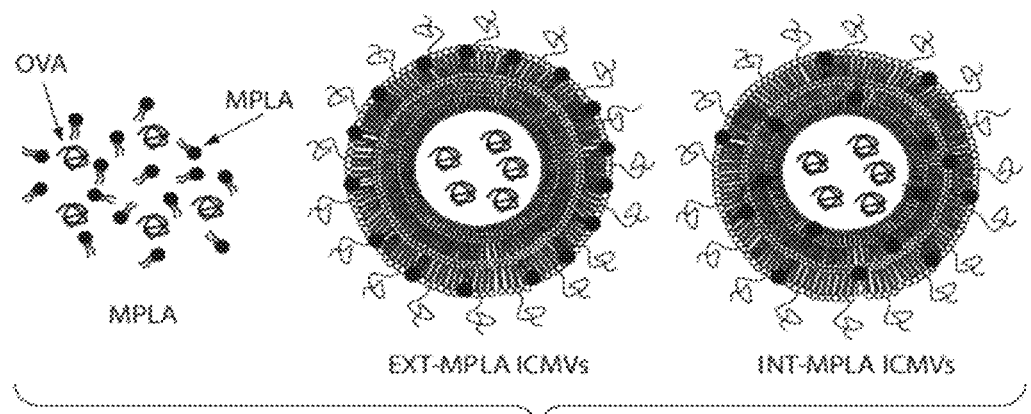
FIG. 11A-E. ICMVs carrying antigen in the aqueous core and MPLA embedded in the vesicle walls elicit potent antibody and $CD8^+$ T-cell responses. (A) Schematic illustration of the vaccine groups: soluble OVA mixed with MPLA (MPLA), OVA-loaded ICMVs with MPLA only on the external surface (ext-MPLA ICMVs), or OVA-loaded ICMVs with MPLA throughout the lipid multilayers (int-MPLA ICMVs). (B-G) C57Bl/6 mice were immunized on days 0, 21, and 35 at tail base s.c. with 10 μg OVA and either 0.1 μg or 1.0 μg of MPLA formulated either as MPLA, ext-MPLA ICMVs, or int-MPLA ICMVs. (B) ELISA analysis of total OVA-specific IgG in sera. (C) Frequency of OVA-specific T-cells in peripheral blood assessed over time via flow cytometry analysis of $tetramer^+CD8^+$ T-cells for vaccinations with 10 μg OVA and 0.1 μg MPLA. Response to vaccinations with soluble OVA+1 μg MPLA is (MPLA 10×) also shown for comparison. Shown are representative flow cytometry scatter plots from individual mice at day 41 and mean tetramer values from groups of mice vs. time. (D) Analysis of T-cell effector/effector memory/central memory phenotypes in peripheral blood by CD44/CD62L staining on $tetramer^+$ cells from peripheral blood on day 41. Shown are representative cytometry plots from individual mice and mean percentages of $tet^+CD44^+CD62L^+$ cells among $CD8^+$ T-cells at day 41. (E) Functionality of antigen-specific $CD8^+$ T-cells was assayed on day 49 with intracellular IFN-γ staining after ex vivo restimulation of PBMCs with OVA peptide in vitro. Representative flow cytometry histograms of $IFN-γ^+CD8^+$ T-cells from individual mice and mean results from groups are shown. Data represent the mean±s.e.m of two independent experiments conducted with n=3. c, *, p<0.05 compared to sol OVA+MPLA and #, p<0.05 compared to ext-MPLA ICMVs. (D, E)*, p<0.05 and **, p<0.01, analyzed by two-way ANOVA, followed by Tukey's HSD.
Figure 11B:
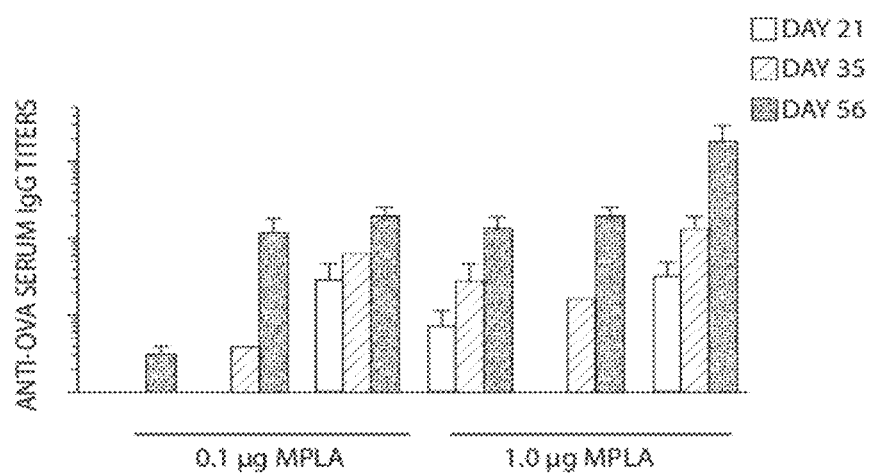

The multilamellar structure of ICMVs offers the opportunity to sequester not only protein antigen (in the aqueous core) but also lipophilic molecules (in the vesicle walls). We thus tested whether embedding MPLA throughout the walls of the ICMVs would impact the immune response in vivo, by allowing better retention of MPLA together with antigen in the vesicles. The TLR agonist was incorporated throughout the vesicle layers by co-dissolving MPLA with the other lipids in the first step of the synthesis (int-MPLA ICMVs), and we compared these vesicles to ICMVs carrying the same amount of MPLA incorporated only on the vesicle surfaces via a post-insertion approach (ext-MPLA ICMVs, FIG. 11A and data not shown). Mice were immunized s.c. with OVA (10 μg) and MPLA (0.1 μg or 1.0 μg) in ICMVs or soluble form, and boosted on day 21 and day 35 with the same formulations. As shown in FIG. 11B, immunizations using the low dose of MPLA led to a barely, detectable antibody response against soluble OVA even following two boosts, while both int-MPLA and ext-MPLA ICMVs elicited strong anti-OVA serum IgG titers by day 56. An IgG response to soluble OVA could be obtained using 10-fold more MPLA, but int-MPLA ICMVs with 1.0 μg MPLA elicited higher titers than soluble protein (~13-fold greater on day 56). On the other hand, we did not observe any significant level of antibodies directed against lipid components of ICMVs throughout these immunization studies (data not shown).

Figure 11C:
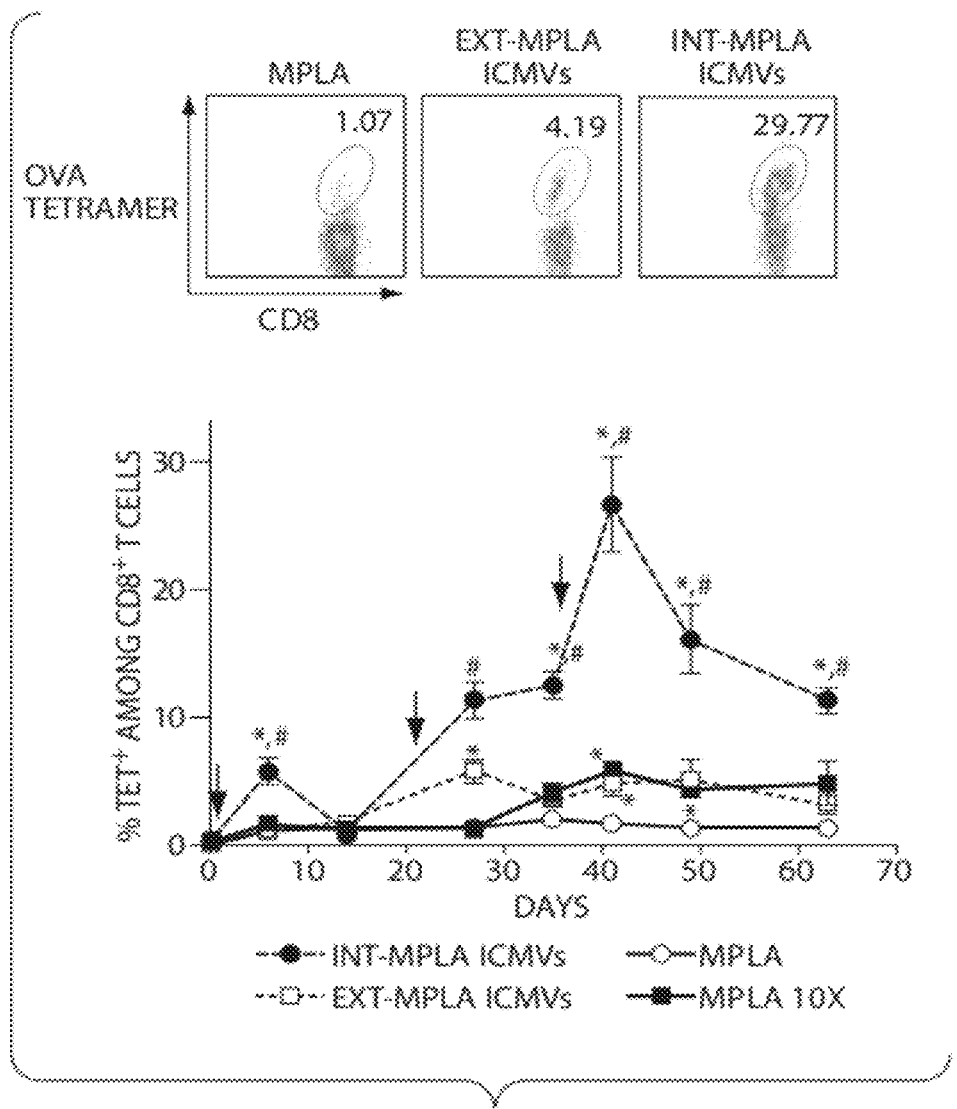
Figure 11D:
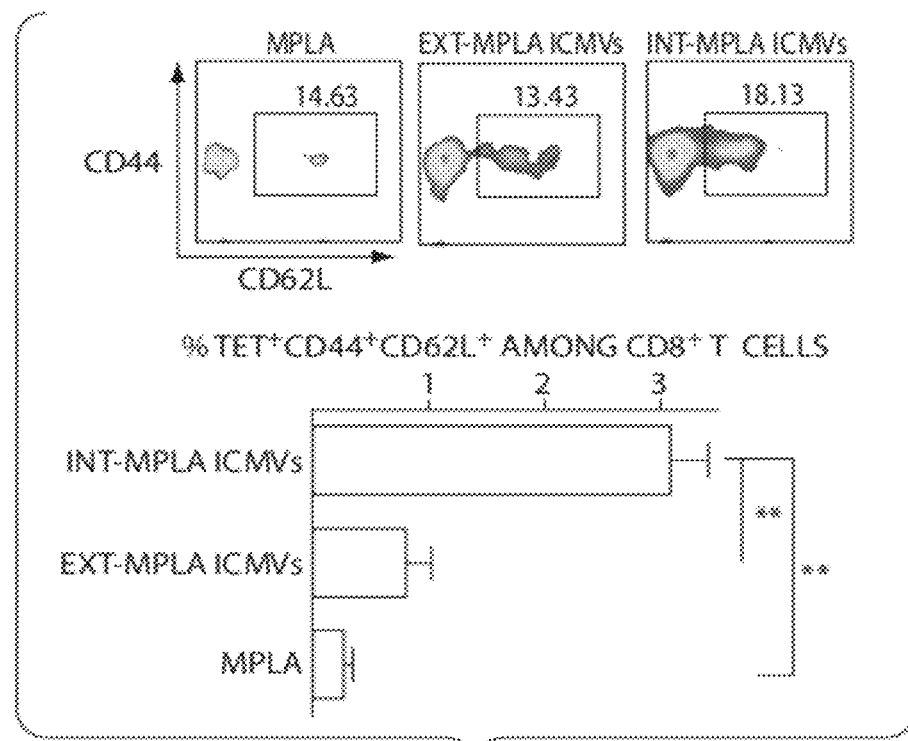
Figure 11E:
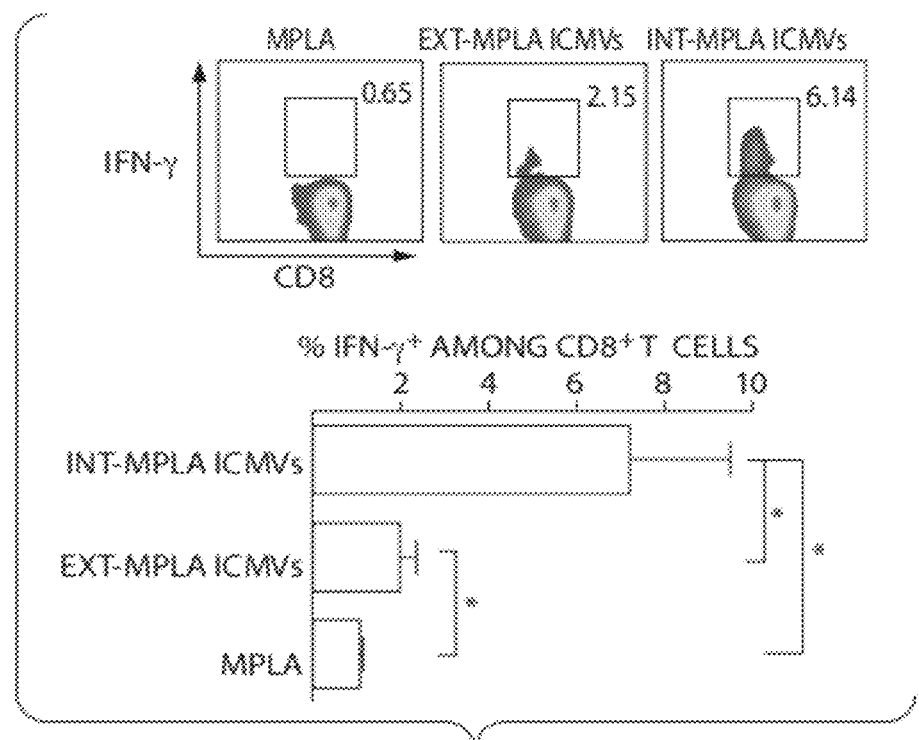

Embedding MPLA in the multilayers of ICMVs had a more striking effect on the CD8$^+$ T-cell response to vaccination. Soluble OVA mixed with 0.1 μg MPLA elicited barely detectable antigen-specific T-cell expansion as assessed by tetramer staining on PBMCs; ext-MPLA ICMV delivery led to a 2.5-fold increased tetramer T-cell population by d41 (FIG. 11C, $p<0.05$). Adding 10-fold more MPLA allowed soluble OVA immunizations to eventually reach T-cell responses equivalent to ext-MPLA ICMVs following boosting. By contrast, immunization with int-MPLA ICMVs elicited dramatically stronger CD8$^+$ T-cell responses that continued to expand following each boost, achieving a peak 28% tetramer$^+$ T-cells in the CD8$^+$ T-cell population by day 41 (5-fold greater than ext-MPLA ICMVs ($p<0.05$) and 14-fold greater than soluble OVA+MPLA ($p<0.01$) FIG. 11C). Notably, int-MPLA ICMVs elicited overall a significantly higher frequency of tetramer$^+$CD44$^+$CD62L$^+$ cells ($p<0.01$, FIG. 11D), a phenotype for central memory T-cells known to confer long-lived protection against pathogens and tumors[48]. Antigen specific T-cells elicited by int-MPLA ICMVs persisted even after one month after the final boosting, with ~11% tetramer$^+$ T-cells among CD8$^+$ T-cells (3-fold and 8-fold greater than ext-MPLA ICMVs and soluble OVA+ MPLA, respectively, $p<0.05$ for both, FIG. 11C). To test the functionality of T-cells expanded by these immunizations, we assessed the ability of CD8$^+$ T-cells from peripheral blood to produce interferon-γ (IFN-γ) upon restimulation ex vivo on day 49. Mice immunized with int-MPLA ICMVs had much higher levels of IFN-γ-competent T-cells than mice receiving ext-MPLA ICMVs or soluble OVA-immunizations ($p<0.05$, FIG. 11E). To our knowledge, in terms of the degree of antigen-specific T-cell expansion, persistence of memory cells, and IFN-γ functionality, this is one of the strongest endogenous T-cell responses ever reported for a protein vaccine, comparable to strong live vectors such as recombinant viruses[5,6]. Notably, this is achieved via "homologous" boosting, repeated immunization with the same particle formulation, a strategy that cannot be used with many live vectors due to immune responses raised against the pathogen-based delivery vector itself[7].

These studies demonstrate the synthesis of a new class of submicron particle reagents based on crosslinked multilamellar lipid vesicles, which combine a number of attractive features for biomedical applications; the particle synthesis does not require exposure of protein cargos to organic solvents, the lipid basis of the particles makes them inherently biodegradable to metabolizable byproducts, the phospholipid shell enables modular entrapment of both lipophilic and hydrophilic cargos, proteins are encapsulated at very high levels per mass of particles, and protein release from the particles can be sustained over very long durations. These results suggest ICMVs may be a very effective vehicle for delivering biomacromolecules, and in particular, for vaccine applications. The ability to achieve such strong combined T-cell and antibody responses using a synthetic particle vaccine could open up new possibilities for vaccination in the setting of infectious disease and cancer.

Example 3

In this Example, we studied the immune response elicited by nanoparticles composed of ICMV carrying recombinant VMP both entrapped in the aqueous core and anchored to the lipid bilayer surfaces. Immunization with these particles and MPLA promoted high-titer, high-avidity antibody responses against VMP, lasting more than 1 year in mice at 10-fold lower doses than conventional adjuvants. Compared to soluble VMP mixed with MPLA, VMP-ICMVs promoted broader humoral responses, targeting multiple epitopes of the protein and a more balanced Th1/Th2 cytokine profile from antigen-specific T-cells. We also examined components of the B-cell response and found that ICMVs promoted robust germinal center (GC) formation at low doses of antigen where no GC induction occurred with soluble protein immunization, and that GCs nucleated near depots of ICMVs accumulating in the draining lymph nodes over time. In parallel, ICMV vaccination enhanced the expansion of antigen-specific follicular helper T-cells, compared to vaccinations with soluble VMP or alum. Thus, ICMV vaccine provide a strategy to enhance the durability, breadth, and potency of humoral immunity by enhancing key elements of the B-cell response.
Materials and Methods.

Synthesis of ICMVs Loaded with VMP.

VMP was prepared as previously described (Yadava et al. 2007 Infect Immun 75:1177-1185; Bell et al. 2009 Vaccine 27:1448-1453). Synthesis of ICMVs was performed as follows: Briefly, dried films of 1.26 μmol of lipids (DOPC: DOPG:MPB (1,2-dioleoyl-sn-glycero-3-phosphoethanolamine-N-[4-(p-maleimidophenyl) butyramide) at 4:1:5 mol ratio (Avanti Polar Lipids, Alabaster, Ala.)) were rehydrated in 20 mM bis-tris propane at pH 7.0 with 50 μg VMP or ovalbumin (Worthington, Lakewood, N.J.) for 1 hr with vortexing every 10 min, and sonicated in alternating power cycles of 6 watts and 3 watts in 30 s intervals for 5 min on ice (Misonix Microson XL probe tip sonicator, Farmingdale, N.Y.). DTT and Ca2+ were then sequentially added at final concentrations of 3 mM and 40 mM, respectively, and incubated for 1 hr at 37° C. to form ICMVs. The particles were recovered by centrifugation, washed twice, and incubated with 10 mg/ml 2 kDa PEG-thiol (Laysan Bio, Arab, Ala.) for 30 min at 37° C. For some experiments, capped-thiol VMP (ctVMP) was prepared by incubating 0.5 mg VMP with 3.6 mM TCEP for 2 hr at 25° C., followed by incubation with 40 mM ethyl-maleimide (Pierce, Rockford, Ill.) at 37° C. for 2 hr. The extent of thiol protection was measured to be >98% by Ellman's assay.

Immunizations.

Animals were cared for following NIH, state, and local guidelines. Groups of 6-10-wk old female C57Bl/6 mice (Jackson Laboratories, Bar Harbor, Me.) were immunized s.c. at the tail base with VMP-ICMVs and indicated doses of MPLA (Sigma-Aldrich, St. Louis, Mo.) in 100 μL PBS on day 0 and 21. Control immunizations with soluble VMP were performed using MPLA, Montanide ISA-50 V2 (Seppic, N.J.), or alum (Imject alum, Pierce, Rockford, Ill.) at an adjuvant:protein solution vol. ratio of 1:1 following the manufacturer's instructions.

Characterization of Anti-VMP Humoral Responses.

Sera were analyzed for IgG, IgG1, and IgG2c antibodies by ELISA using VMP-coated plates (Bell et al. 2009 Vaccine 27:1448-1453). Anti-VMP IgG titers were defined as the lowest serum dilution at which the ELISA OD reading was ≥0.5. Avidity measurements were performed by incubating plates with 6 M urea for 10 min at 20° C. to remove weakly bound IgG prior to addition of detection Ab. The avidity index was defined as (IgG titer with 6 M urea/IgG titer without urea)×100. For epitope analysis, strepavidin-coated plates (Pierce) were incubated with 50 μg/ml peptide fragments derived from VMP; Type I repeat (GDRAAGQPAGDRADGQPA; SEQ ID NO:3), AGDRx5 (AGDRAGDRAGDRAGDRAGDR; SEQ ID NO:4), Region I (NPRENKLKQP; SEQ ID NO:5), Region II (EWTPCSVTCGVGVRVRRR; SEQ ID NO:6), C-terminus (PNEKSVKEYLDK; SEQ ID NO:7), or a scrambled control (KPLDVEKNSEY; SEQ ID NO:8), each with an N-terminal biotin-GSSSG spacer. Splenocytes isolated 7 d after boost vaccinations were restimulated ex vivo with either PBS or VMP-ICMV at 2 μg/ml, and on d2, cytokine levels in the culture supernatants were measured by flow cytometry (Cytometric Bead Array, BD).

Germinal Center and Follicular Helper T Cell Analysis.

Mice were immunized s.c. with 5 μg of MPLA and 100 μg of OVA-alexa fluor 555 in either soluble or ICMV formulations (lipids labeled with DiD). At serial time-points, dLNs were isolated, flash-frozen, cryo-sectioned, and examined by confocal microscopy. To identify cell types associated with particles, dLNs were isolated on d 1 or 4, stained with anti-CD11b, anti-CD11c, anti-CD169, anti-CD205, and F4/80, and analyzed by flow cytometry. To assess GC formation, dLNs were isolated on d14 from mice immunized with 1 μg of unlabeled soluble VMP or VMP-ICMVs (both with 0.1 μg MPLA), stained with anti-B220, anti-IgD, anti-GL-7 (BD), peanut agglutinin (Vectorlabs, Burlingame, Calif.), and analyzed by flow cytometry or confocal microscopy. To monitor antigen-specific CD4+ T-cells, 1050VA-specific CD4+ T cells from OT-II (CD45.2+) mice were adoptively transferred i.v. into recipient congenic CD45.1+ mice. After 1 d, recipient mice were immunized s.c. with 10 μg of OVA in either soluble or ICMV formulations, both with 1 μg MPLA. A second comparison group of mice were immunized s.c. with 100 μg OVA in alum. The frequencies of OVA-specific CD4+ T cells and their phenotypes in spleens and dLNs were determined by flow cytometry analysis, following staining with DAPI, anti-CD4, anti-CD45.2, anti-PD-1, and anti-CXCR5 (BD).

Statistical Analysis.

Data sets were analyzed using one- or two-way analysis of variance (ANOVA), followed by Tukey's HSD test for multiple comparisons with Prism 5.0 (GraphPad Software, San Diego, Calif.). p-values less than 0.05 were considered statistically significant. All values are reported as mean±s.e.m.

Results

Design of ICMV Combining Membrane Display and Encapsulation of Soluble Antigen.

The synthesis of antigen-loaded ICMVs proceeds in 3 steps: formation of anionic maleimide (MAL)-functionalized vesicles by hydration of lipid films in the presence of antigen, fusion of vesicles via divalent cations, and finally "stapling" of the vesicles by addition of membrane-permeable dithiols that crosslink lipid headgroups bilayer-to-bilayer. To determine whether the effectiveness of ICMVs could be further enhanced, we exploited the MAL groups in ICMV as sites for both crosslinking of the bilayers and for conjugation to free cysteines of VMP. We thus formed ICMVs comprising VMP which contains cysteines at its N- and C-termini. In a typical synthesis, a total of 45±8.2 μg of VMP was incorporated in ICMVs per mg of lipids with 50±9.1% loading efficiency. PEGylated VMP-loaded ICMVs (VMP-ICMVs) had hydrodynamic diameters of 180±14 nm and a relatively narrow size distribution with polydispersity index of 0.29±0.021.

To assess whether VMP was linked to the membranes of ICMV, we probed for surface-accessible VMP using antibodies (Abs) against the C-terminal his-tag of the VMP protein. Such Ab bound to VMP-ICMVs, but not to OVA-ICMVs or VMP-ICMVs treated with trypsin to digest surface-bound protein. Blockade of MAL-mediated coupling by capping the free thiols of VMP with ethyl maleimide before particle synthesis (ctVMP-ICMVs) did not affect protein loading efficiency significantly (44±8.5%, p=0.45), but eliminated Ab binding, suggesting that VMP display on the ICMV surfaces was due to conjugation with MAL lipid headgroups rather than by surface adsorption. In agreement with these bulk measurements, confocal micrographs of fluorescently-tagged VMP-ICMVs showed lipid colocalization with Ab staining, which was absent for OVA-ICMVs, trypsin-treated VMP-ICMVs, or ctVMP-ICMVs.

To test the impact of membrane conjugation on the immunogenicity of ICMVs, mice were immunized with VMP-ICMVs, where antigen was both membrane-conjugated and encapsulated, or with ctVMP-CMVs, where antigen was only encapsulated in a soluble state in the particle interior. Mice in each group were primed and then boosted on d 21 with a total of 1 μg VMP and 0.1 μg MPLA. Measurement of resulting serum VMP-specific IgG titers showed that membrane display of the antigen increased the potency of ICMV vaccination, as homologous VMP-ICMV immunization elicited IgG titers ~9-fold greater than homologous ctVMP-ICMV immunization (p<0.05). Heterologous immunizations with VMP-ICMVs and ctVMP-ICMVs revealed that vaccination with antigen bound on ICMV surfaces during the prime rather than boost was more critical to elicit high IgG titers.

VMP-ICMV Vaccination Induces Durable Antibody Responses at 10-Fold Lower Doses of Antigen than Soluble Protein or Traditional Adjuvants.

Figure 13A:
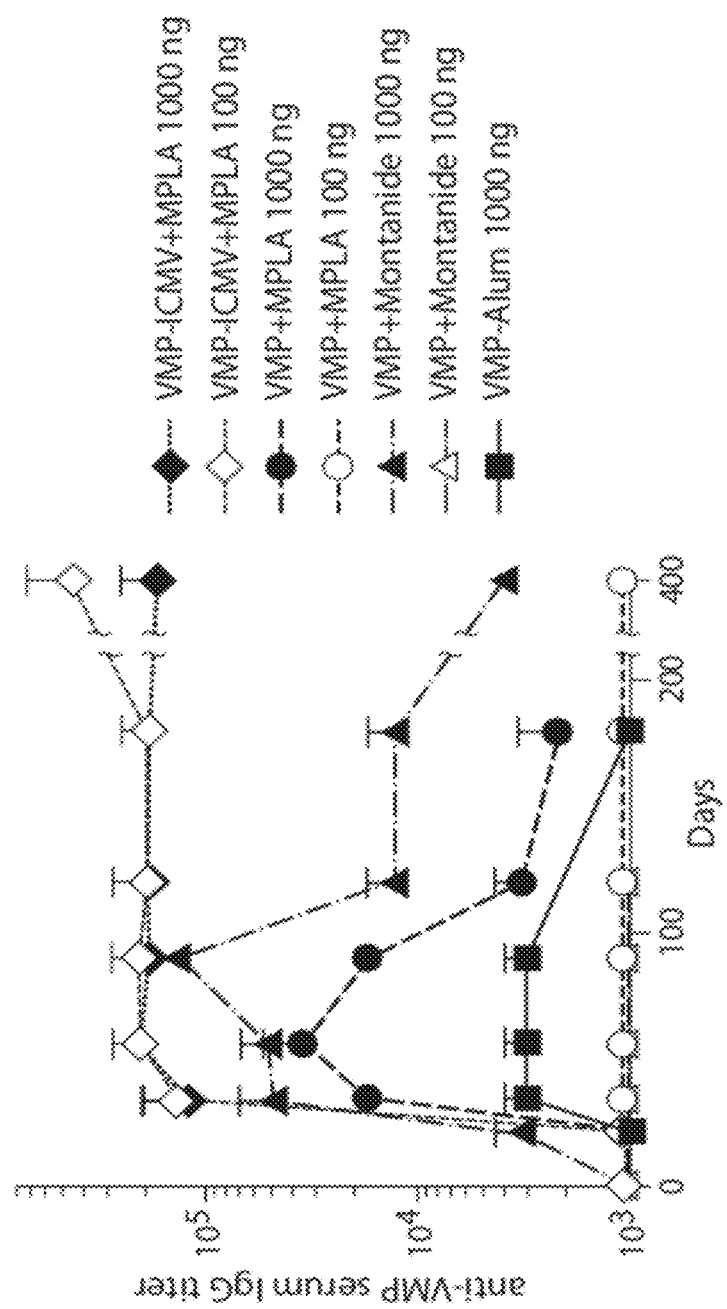
FIGS. 13A-E. VMP-ICMV vaccines elicit robust, durable antibody titers with significantly reduced antigen/adjuvant doses. C57Bl/6 mice were immunized s.c. on d 0 and d 21 with the indicated doses of VMP in ICMVs mixed with 25 μg MPLA, or as soluble proteins mixed with either 25 μg MPLA, Montanide ISA-50, or alum. (A) Anti-VMP IgG sera titers were assessed over time by ELISA. Anti-VMP IgG sera were further characterized on d 90 for (B) IgG$_1$ and (C) IgG$_{2c}$ titers (n.d., not detected). (D) Splenocytes isolated 7 d after priming and boosting with 1 µg VMP and 0.1 µg MPLA were stimulated with PBS (white bars) or 2 µg/ml VMP-ICMVs (black bars) ex vivo, and the cell media were analyzed on d 2 for the concentrations of cytokines. (E) Mice were immunized with titrated amounts of MPLA mixed with 1 µg of VMP in either soluble or ICMV formulations. Shown are anti-VMP IgG sera titers measured by ELISA on d 50. Data represent the mean±s.e.m of two independent experiments with n=3-4 per group. *, p<0.05, analyzed by one-way or two-way ANOVA, followed by Tukey's HSD.
Figure 13B:
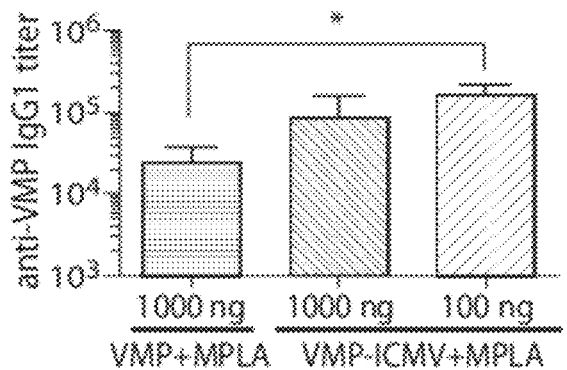
Figure 13C:
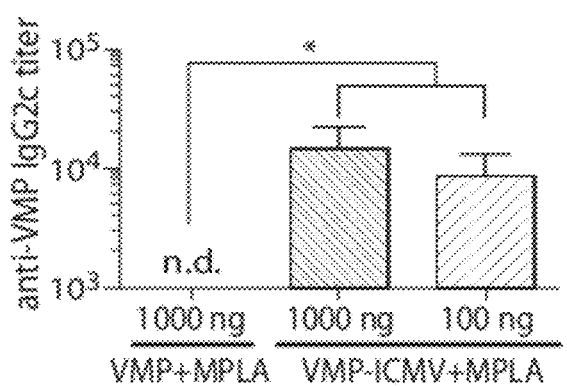
Figure 13D:
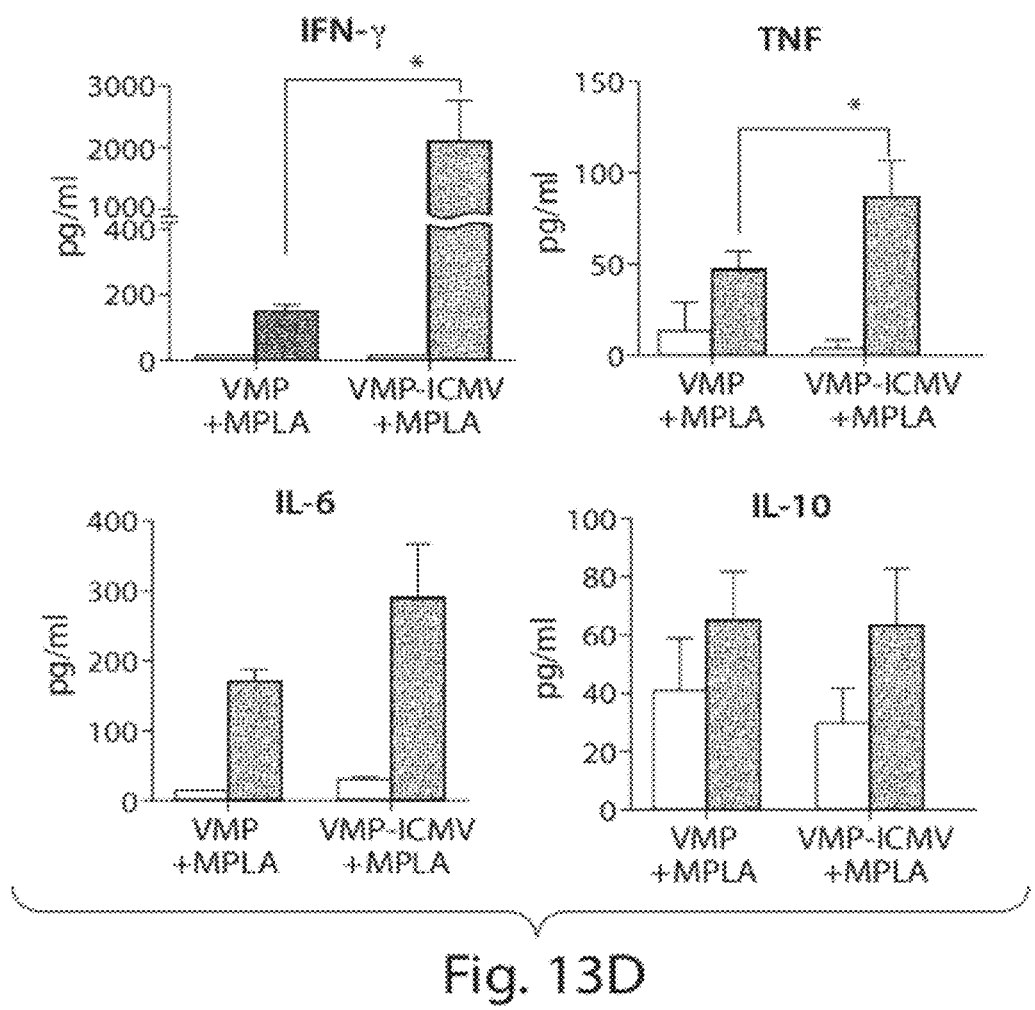

Immunization of C57Bl/6 mice with VMP-ICMVs mixed with MPLA as a molecular adjuvant elicited durable, high titers of serum anti-VMP IgG, sustained for more than one year following a prime and boost with as little as 100 ng of the malaria antigen (FIG. 13A). By contrast, vaccines composed of soluble VMP mixed with MPLA or adjuvanted with Montanide or alum required at least 10-fold more protein to elicit a response, and exhibited waning titers over time (FIG. 13A). VMP-ICMV+MPLA vaccination induced antigen-specific IgG1 and IgG2c isotype responses, while soluble protein+ MPLA elicited only Th2-skewed IgG1 antibodies (FIG. 13B, C). Priming of a more balanced Th1/Th2 antibody response correlated with the enhanced production of IFN-γ and TNF-α by splenocytes from ICMV-immunized mice, compared to soluble protein vaccination (FIG. 13D). VMP-ICMVs incubated with sera from naïve, VMP-ICMV-, or OVA-ICMV-immunized mice had detectable binding only to VMP-ICMV sera, indicating minimal cross-reactivity of elicited IgG to non-protein components of ICMVs, i.e. maleimide, lipids or PEG. Notably, VMP-ICMVs reconstituted in saline from lyophilized powders maintained their original particle diameter and size distribution (diameter of 200 nm±11, polydispersity index of 0.23±0.05), and elicited similar humoral responses, suggesting that freeze-dried materials could be used to enhance the storage life of ICMV vaccines.

Enhanced Immunogenicity of ICMV Formulated Antigen Enables Dose Sparing of Adjuvant.

Figure 13E:
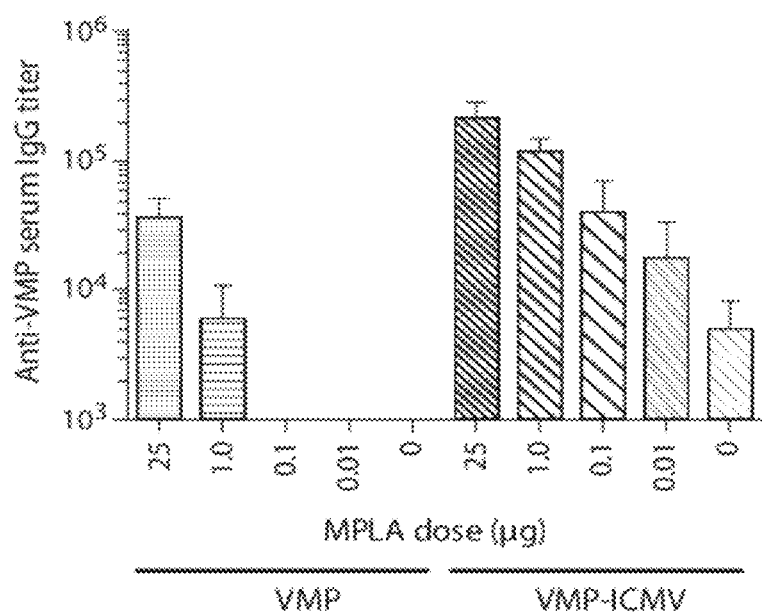

Strategies to reduce the dose of potent immunostimulatory adjuvants such as MPLA or other TLR agonists are attractive, to lower the risk of reactogenicity or other side effects that could hamper the safety of vaccine candidates. To determine whether the enhanced immunogenicity of ICMVs would permit dose sparing of an adjuvant such as MPLA, we titrated down the dose of MPLA with a fixed dose of VMP antigen (1 µg) in soluble or ICMV form. Strikingly, the peak IgG response was comparable for 25 µg or 1 µg MPLA given with VMP-ICMVs, and MPLA doses as low as 100 ng elicited IgG titers comparable to a 250-fold greater dose of MPLA given with soluble protein (FIG. 13E).

ICMV Delivery Increases the Breadth and Avidity of the Humoral Responses.

Figure 14A:
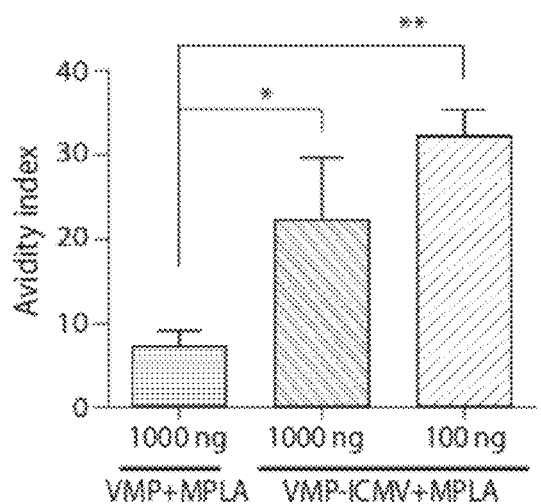
FIGS. 14A-B. VMP-ICMV immunization elicits antibodies with high avidity and broader specificity than soluble protein vaccination. C57Bl/6 mice were immunized with VMP-ICMVs or soluble VMP (25 µg MPLA with 0.1 or 1 µg protein) as in FIG. 13 and avidity and specificity of sera were analyzed on d 90. (A) Avidity index of sera from immunized mice binding to whole VMP protein. (B) Anti-VMP IgG antibodies elicited with VMP-ICMVs+MPLA (blue) or VMP+MPLA (red) were further analyzed for binding to fragments of VMP, including the Type I insert, AGDRx5, Region I, Region II, C-terminus, or a scrambled peptide negative control. Data represent the mean±s.e.m of 2 independent experiments conducted with n=3. *, p<0.05 and **, p<0.01, analyzed by one-way ANOVA, followed by Tukey's HSD.
Figure 14B:
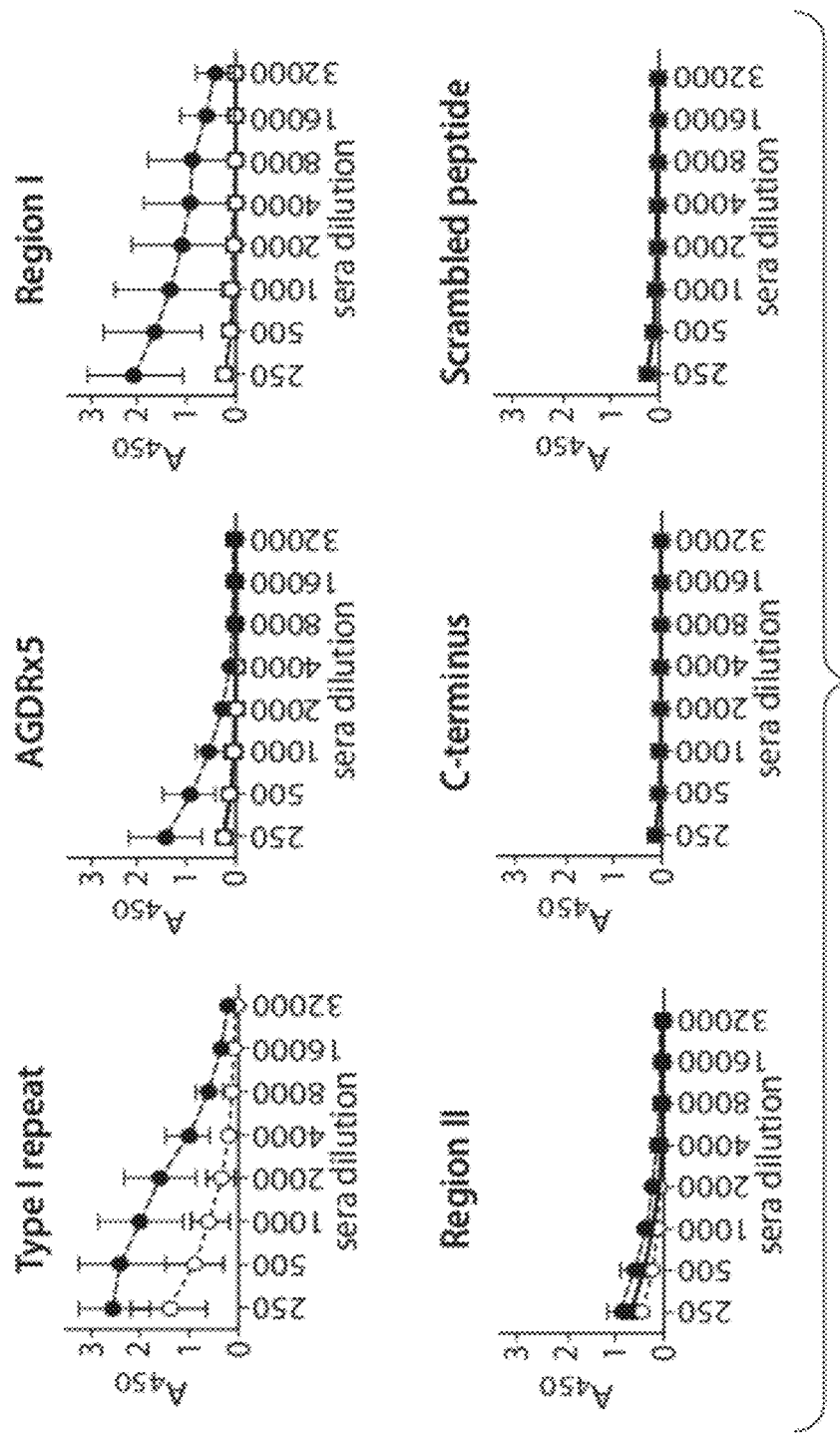

To evaluate the quality of the antibody response raised against VMP, we assessed the avidity and epitope specificity of sera from immunized animals. ICMV vaccinations elicited IgG responses with up to 4.3-fold higher avidity than soluble protein immunization (VMP-ICMV vs. VMP at 1 µg, $p<0.05$) (FIG. 14A). Sera from mice immunized with VMP-ICMVs bound the Type I repeat sequence with significantly higher titers, and explicitly recognized the AGDR motif, while sera from soluble protein immunizations did not recognize this fragment (FIG. 14B). ICMV vaccination also generated antibodies capable of recognizing the Region I domain, which may inhibit sporozoite invasion into hepatocytes by blocking receptor-ligand interactions during parasite entry (Ancsin et al., 2004, J. Biol. Chem. 279:21824-21832). In contrast, the C-terminal fragment of VMP and the Region II domain, which share sequence homology to endogenous thrombospondin (Bilsborough et al., 1997, Acta Trop 65:59-80), were not recognized by antibodies elicited with either vaccine, suggesting lack of activation of self-reactive B cells. Taken together, these results suggest that ICMV vaccination generates antibody responses that are more durable and have higher avidity than those elicited by traditional adjuvants even using 10-fold less antigen, and elicit broader humoral responses with the capacity to recognize the sporozoite domains thought to be critical in protective immunity against infection.

Enhanced Antigen Delivery and Germinal Center Formation Triggered by ICMVs.

Durable and high-affinity humoral responses elicited by ICMVs suggest that ICMV-based vaccines may effectively stimulate formation of GCs, where activated B-cells proliferate, undergo immunoglobulin isotype-switching and somatic hypermutation, and eventually form memory B-cells that can rapidly differentiate into plasma cells on re-exposure to antigen (McHeyzer-Williams et al., 2005, Annu. Rev. Immunol. 23:487-513; Nutt et al., 2011, Nat Immunol. 131:472-477). To investigate GC induction and its anatomic relationship with ICMV delivery to dLNs, we immunized mice with fluorophore-conjugated OVA (soluble or encapsulated in fluorescent ICMVs) and MPLA, and carried out histological analyses of dLNs at serial time-points. Soluble OVA was detected in the dLNs within 4 hrs, but was rapidly cleared within 24 hrs. In contrast, OVA-loaded ICMVs were detected at the subcapsular sinus (SCS) of dLNs by 24 hrs, with continued accumulation over the next 2 weeks, depositing a large amount of antigen beneath the SCS. Flow cytometry and histological analysis of OVA+ cells 1 or 4 days post ICMV injection showed that the major APC population acquiring the ICMV particles were LN-resident macrophages, although OVA+ CD11b+CD11c+ DCs were also detected, suggesting that both free draining and cell-mediated transport of ICMV particles to the dLN contributed at both time points.

OVA-ICMV immunizations elicited prominent GC formation, and notably, in the majority of cases, GCs were nucleated within 100 µm of ICMV-draining sites in dLNs. Immunization with VMP-ICMVs also induced GCs; compared with soluble VMP+MPLA immunizations, ICMVs induced a significantly enhanced frequency and 8-fold increase in the absolute number of isotype class-switched GC B cells (B220+IgDlowGL-7+PNA+) in dLNs by d 14 ($p<0.05$). Histological analysis revealed 2-5 GCs per dLN in mice immunized with 100 ng VMP-ICMV+MPLA, in contrast to their complete absence in the VMP+MPLA immunization groups. Notably, as observed with OVA, VMP-ICMVs promoted GCs in close proximity to the particle-draining sites, with ~75% of GCs observed directly adjacent to ICMV deposits.

ICMV Vaccination Enhances the Generation of Antigen-Specific Tfh Cells.

Strong humoral immune responses, characterized by GC formation and long-lived plasma and memory B cells, are dependent on help provided by CD4+ Tfh cells (Breitfeld et al. 2000, J Exp Med 192:1545-1552; Deenick et al. 2010 Immunity 33:241-253). To determine whether ICMVs amplify the humoral response in part by enhanced CD4+ T-cell differentiation, we turned to a model system to trace antigen-specific T helper responses: TCR-transgenic CD45.2+ OT-II CD4+ T-cells recognizing OVA peptides were adoptively transferred into CD45.1+ recipient mice that were subsequently immunized with 1 µg MPLA mixed with 10 µg soluble OVA or OVA-ICMVs. As an additional comparison, mice were also immunized with the traditional adjuvant alum and a 10-fold greater dose of OVA (100 µg). Eight days post priming, soluble protein immunization induced ~6.3-fold expansion of OT-II CD4+ T-cells in spleens compared to mice treated with PBS after adoptive transfer; in contrast, OVA-ICMV vaccination induced a ~21-fold expansion of the transferred cells compared with PBS controls ($p<0.05$). Alum also induced robust expansion of OVA-specific T-cells (~23-fold increase compared to PBS, $p<0.05$). Notably, OVA-ICMV vaccination promoted differentiation of OT-II CD4+ T-cells toward Tfh phenotypes (CXCR5+PD-1+), leading to a substantially increased frequency of antigen-specific Tfh cells compared to the other immunization regimens. Taken together, these results suggest that the enhanced humoral responses elicited by ICMVs compared to soluble vaccines or other traditional adjuvants are a product of enhanced GC formation and increased expansion/differentiation of antigen-specific CD4+ T cells toward Tfh phenotypes.

VMP Amino Acid Sequence (SEQ ID NO: 1)

THCGHNVDLS KAINLNGVNF NNVDASSLGA AHVGQSASRG RGLGENPDDE EGDAKKKKDG

KKAEPKNPRE NKLKQPGDRA DGQAAGNGAG GQPAGDRAAG QPAGDRAAGQ PAGDGAAGQP

AGDRADGQPA GDRADGQPAG DRAAGQAAGN GAGGQAAANG AGNQPGGGNA ANKKAEDAGG

NAGGNAGGQG QNNEGANAPN EKSVKEYLDK VRATVGTEWT PCSVTCGVGV RVRRRVNAAN

KKPEDLTLND LETDVCT

VMP Nucleotide Sequence (SEQ ID NO: 2)

acacattgcg gacataatgt agatttatct aaagctataa atttaaatgg tgtaaacttc aataacgtag acgctagttc actcggggct gcgcacgtag gtcagtctgc tagcaggggg cgcggtctcg gggaaaaccc agacgacgaa gaaggtgatg ctaaaaagaa aaaggacggt aaaaagcgg aaccaaaaaa tccaaggaa aataaattaa aacagcccgg ggatcgcgcg gatggtcaag cggcgggtaa tggggcgggg ggtcaaccag cggggatcg cgcggctggt cagccagcg gggatcgcgc ggctggtcag ccagcgggg atggtgcggc tggccaacca gcggggatc gcgcggatgg tcagccagcg ggggatcgcg cggatggtca accagccggt gatcgcgcg ctggccaagc ggccggtaat ggggcgggg gtcaagcggc cgcgaacgga gcggggaacc agccaggcgg cggtaacgct gcgaataaaa aagcggaaga tgcgggtggt aacgcgggcg gtaatgcggg cggccaaggt cagaacaacg aaggggctaa tgcaccaaac gaaaaatctg tcaaagaata tctcgataaa gtccgcgcta cagtagggac agaatggacg ccatgctctg taacatgtgg tgtcggggta cgcgtgcgcc gccgtgtcaa tgcggctaac aaaaaaccag aagatctcac gttaaatgat ctcgaaacgg atgtctgcac a

REFERENCES

1. Guy, B. The perfect mix: recent progress in adjuvant research. *Nat Rev Microbiol* 5, 505-517 (2007).
2. Perrie, Y., Mohammed, A. R., Kirby, D. J., McNeil, S. E. & Bramwell, V. W. Vaccine adjuvant systems: enhancing the efficacy of sub-unit protein antigens. *Int J Pharm* 364, 272-280 (2008).
3. Reed, S. G., Bertholet, S., Coler, R. N. & Friede, M. New horizons in adjuvants for vaccine development. *Trends Immunol* 30, 23-32 (2009).
4. Walker, B. D. & Burton, D. R. Toward an AIDS vaccine. *Science* 320, 760-764 (2008).
5. Haglund, K., et al. Robust recall and long-term memory T-cell responses induced by prime-boost regimens with heterologous live viral vectors expressing human immunodeficiency virus type 1 Gag and Env proteins. *J Virol* 76, 7506-7517 (2002).
6. Flatz, L., et al. Development of replication-defective lymphocytic choriomeningitis virus vectors for the induction of potent CD8+ T cell immunity. *Nat Med* 16, 339-345 (2010).
7. Brave, A., Ljungberg, K., Wahren, B. & Liu, M. A. Vaccine delivery methods using viral vectors. *Mol Pharm* 4, 18-32 (2007).
8. Priddy, F. H., et al. Safety and immunogenicity of a replication-incompetent adenovirus type 5 HIV-1 Glade B gag/pol/nef vaccine in healthy adults. *Clin Infect Dis* 46, 1769-1781 (2008).
9. Hubbell, J. A., Thomas, S. N. & Swartz, M. A. Materials engineering for immunomodulation. *Nature* 462, 449-460 (2009).
10. Heath, W. R. & Carbone, F. R. Cross-presentation in viral immunity and self-tolerance. *Nat Rev Immunol* 1, 126-134 (2001).
11. Kwon, Y. J., James, E., Shastri, N. & Frechet, J. M. In vivo targeting of dendritic cells for activation of cellular immunity using vaccine carriers based on pH-responsive microparticles. *Proc Natl Acad Sci USA* 102, 18264-18268 (2005).
12. Hamdy, S., et al. Enhanced antigen-specific primary CD4+ and CD8+ responses by codelivery of ovalbumin and toll-like receptor ligand monophosphoryl lipid A in poly(D,L-lactic-co-glycolic acid) nanoparticles. *J Biomed Mater Res A* 81, 652-662 (2007).
13. Heit, A., Schmitz, F., Haas, T., Busch, D. H. & Wagner, H. Antigen co-encapsulated with adjuvants efficiently drive protective T cell immunity. *Eur J Immunol* 37, 2063-2074 (2007).
14. Schlosser, E., et al. TLR ligands and antigen need to be coencapsulated into the same biodegradable microsphere for the generation of potent cytotoxic T lymphocyte responses. *Vaccine* 26, 1626-1637 (2008).
15. Heffernan, M. J., Kasturi, S. P., Yang, S. C., Pulendran, B. & Murthy, N. The stimulation of CD8+ T cells by dendritic cells pulsed with polyketal microparticles containing ion-paired protein antigen and poly(inosinic acid)-poly(cytidylic acid). *Biomaterials* 30, 910-918 (2009).
16. Demento, S. L., et al. Inflammasome-activating nanoparticles as modular systems for optimizing vaccine efficacy. *Vaccine* 27, 3013-3021 (2009).
17. Reddy, S. T., et al. Exploiting lymphatic transport and complement activation in nanoparticle vaccines. *Nat Biotechnol* 25, 1159-1164 (2007).

18. Torchilin, V. P. Recent advances with liposomes as pharmaceutical carriers. *Nat Rev Drug Discov* 4, 145-160 (2005).
19. Gregoriadis, G., Gursel, I., Gursel, M. & McCormack, B. Liposomes as immunological adjuvants and vaccine carriers. *Journal of Controlled Release* 41, 49-56 (1996).
20. Jeong, J. M., Chung, Y. C. & Hwang, J. H. Enhanced adjuvantic property of polymerized liposome as compared to a phospholipid liposome. *J Biotechnol* 94, 255-263 (2002).
21. Vangala, A., et al. Comparison of vesicle based antigen delivery systems for delivery of hepatitis B surface antigen. *J Control Release* 119, 102-110 (2007).
22. Steers, N. J., Peachman, K. K., McClain, S., Alving, C. R. & Rao, M. Liposome-encapsulated HIV-1 Gag p24 containing lipid A induces effector CD4+ T-cells, memory CD8+ T-cells, and pro-inflammatory cytokines. *Vaccine* 27, 6939-6949 (2009).
23. Bhowmick, S., Mazumdar, T., Sinha, R. & A11, N. Comparison of liposome based antigen delivery systems for protection against *Leishmania donovani*. *J Control Release* 141, 199-207 (2010).
24. Reddy, R., Thou, F., Nair, S., Huang, L. & Rouse, B. T. In vivo cytotoxic T lymphocyte induction with soluble proteins administered in liposomes. *J Immunol* 148, 1585-1589 (1992).
25. Collins, D. S., Findlay, K. & Harding, C. V. Processing of exogenous liposome-encapsulated antigens in vivo generates class I MHC-restricted T cell responses. *J Immunol* 148, 3336-3341 (1992).
26. Wakita, D., et al. An indispensable role of type-1 IFNs for inducing CTL-mediated complete eradication of established tumor tissue by CpG-liposome co-encapsulated with model tumor antigen. *Int Immunol* 18, 425-434 (2006).
27. Popescu, M. C., et al. A novel proteoliposomal vaccine elicits potent antitumor immunity in mice. *Blood* 109, 5407-5410 (2007).
28. Allen, T. M., Mumbengegwi, D. R. & Charrois, G. J. Anti-CD19-targeted liposomal doxorubicin improves the therapeutic efficacy in murine B-cell lymphoma and ameliorates the toxicity of liposomes with varying drug release rates. *Clin Cancer Res* 11, 3567-3573 (2005).
29. Cashion, M. P. & Long, T. E. Biomimetic Design and Performance of Polymerizable Lipids. *Accounts of Chemical Research* 42, 1016-1025 (2009).
30. Hotz, J. & Meier, W. Vesicle-templated polymer hollow spheres. *Langmuir* 14, 1031-1036 (1998).
31. Mahadevan, S. & Tappel, A. L. Lysosomal lipases of rat liver and kidney. *J Biol Chem* 243, 2849-2854 (1968).
32. Papahadjopoulos, D., Nir, S. & Duzgunes, N. Molecular mechanisms of calcium-induced membrane fusion. *J Bioenerg Biomembr* 22, 157-179 (1990).
33. Zauner, W., Farrow, N. A. & Haines, A. M. In vitro uptake of polystyrene microspheres: effect of particle size, cell line and cell density. *J Control Release* 71, 39-51 (2001).
34. Mohammed, A. R., Bramwell, V. W., Coombes, A. G. & Perrie, Y. Lyophilisation and sterilisation of liposomal vaccines to produce stable and sterile products. *Methods* 40, 30-38 (2006).
35. Girard, P., et al. A new method for the reconstitution of membrane proteins into giant unilamellar vesicles. *Biophys J* 87, 419-429 (2004).
36. Lutsiak, M. E., Robinson, D. R., Coester, C., Kwon, G. S. & Samuel, J. Analysis of poly(D,L-lactic-co-glycolic acid) nanosphere uptake by human dendritic cells and macrophages in vitro. *Pharm Res* 19, 1480-1487 (2002).
37. Huisgen, R. Cycloadditions—definition classification and characterization. *Angewandte Chemie-International Edition* 7, 321-& (1968).
38. Wang, Q., et al. Bioconjugation by copper(I)-catalyzed azide-alkyne [3+2] cycloaddition. *J Am Chem Soc* 125, 3192-3193 (2003).
39. Allen, T. M. & Cullis, P. R. Drug delivery systems: entering the mainstream. *Science* 303, 1818-1822 (2004).
40. Mundargi, R. C., Babu, V. R., Rangaswamy, V., Patel, P. & Aminabhavi, T. M. Nano/micro technologies for delivering macromolecular therapeutics using poly(D,L-lactide-co-glycolide) and its derivatives. *J Control Release* 125, 193-209 (2008).
41. Vasir, J. K. & Labhasetwar, V. Biodegradable nanoparticles for cytosolic delivery of therapeutics. *Adv Drug Deliv Rev* 59, 718-728 (2007).
42. Gabizon, A., et al. Prolonged circulation time and enhanced accumulation in malignant exudates of doxorubicin encapsulated in polyethylene-glycol coated liposomes. *Cancer Res* 54, 987-992 (1994).
43. Kirby, C. & Gregoriadis, G. Dehydration-rehydration vesicles—a simple method for high-yield drug entrapment in liposomes. *Bio-Technology* 2, 979-984 (1984).
44. Bershteyn, A., et al. Polymer-supported lipid shells, onions, and flowers. *Soft Matter* 4, 1787-1791 (2008).
45. McKee, A. S., Munks, M. W. & Marrack, P. How do adjuvants work? Important considerations for new generation adjuvants. *Immunity* 27, 687-690 (2007).
46. Mata-Haro, V., et al. The vaccine adjuvant monophosphoryl lipid A as a TRW-biased agonist of TLR4. *Science* 316, 1628-1632 (2007).
47. Porgador, A., Yewdell, J. W., Deng, Y., Bennink, J. R. & Germain, R. N. Localization, quantitation, and in situ detection of specific peptide-MHC class I complexes using a monoclonal antibody. *Immunity* 6, 715-726 (1997).
48. Sallusto, F., Geginat, J. & Lanzavecchia, A. Central memory and effector memory T cell subsets: function, generation, and maintenance. *Annu Rev Immunol* 22, 745-763 (2004).
49. Yadava, A., et al. A novel chimeric *Plasmodium vivax* circumsporozoite protein induces biologically functional antibodies that recognize both VK210 and VK247 sporozoites. *Infect Immun* 75, 1177-1185 (2007).
50. Ellman, G. L. Tissue sulfhydryl groups. *Arch Biochem Biophys* 82, 70-77 (1959).

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A multilamellar lipid vesicle comprising a terminal-cysteine-bearing antigen, and having covalent crosslinks between lipid bilayers, wherein at least two lipid bilayers in the multilamellar lipid vesicle are covalently crosslinked to each other through headgroups that react with covalent crosslinkers to form the covalent crosslinks between lipid bilayers.

2. The multilamellar lipid vesicle of claim 1, wherein the antigen is a cysteine-modified antigen.

3. The multilamellar lipid vesicle of claim 1, wherein the vesicle comprises phosphocholine.

4. The multilamellar lipid vesicle of claim 1, wherein the vesicle comprises phosphoglycerol.

5. The multilamellar lipid vesicle of claim 1, wherein the vesicle comprises a maleimide functionalized lipid.

6. The multilamellar lipid vesicle of claim 1, wherein the antigen is or comprises a whole protein antigen.

7. The multilamellar lipid vesicle of claim 1, wherein the antigen is or comprises a fragment of a whole protein antigen.

8. The multilamellar lipid vesicle of claim 1, wherein the vesicle further comprises an adjuvant.

9. The multilamellar lipid vesicle of claim 1, wherein the antigen is present on the surface of the vesicles.

10. The multilamellar lipid vesicle of claim 1, wherein the antigen is encapsulated between lipid bilayers and/or is present in the core of the vesicle.

11. The multilamellar lipid vesicle of claim 1, wherein the vesicle is surface-conjugated to polyethylene glycol (PEG).

12. A composition comprising multilamellar lipid vesicles of claim 1.

13. A composition comprising multilamellar lipid vesicles of claim 1 and a pharmaceutically acceptable carrier.

14. A composition comprising multilamellar lipid vesicles of claim 1 and an adjuvant.

15. A composition comprising multilamellar lipid vesicles of claim 1, wherein the vesicles are lyophilized.

16. A multilamellar lipid vesicle comprising a terminal-cysteine-bearing antigen that is encapsulated between lipid bilayers and/or is present in the core of the vesicle, and having covalent crosslinks between lipid bilayers, wherein at least two lipid bilayers in the multilamellar lipid vesicle are covalently crosslinked to each other through headgroups that react with covalent crosslinkers to form the covalent crosslinks between lipid bilayers.

* * * * *